United States Patent
Corsello et al.

(10) Patent No.: US 11,633,415 B2
(45) Date of Patent: Apr. 25, 2023

(54) COMPOUNDS AND METHODS USEFUL FOR TREATING OR PREVENTING CANCERS

(71) Applicants: THE BROAD INSTITUTE, INC., Cambridge, MA (US); DANA-FARBER CANCER INSTITUTE, INC., Boston, MA (US)

(72) Inventors: Steven M. Corsello, Boston, MA (US); Todd R. Golub, Cambridge, MA (US); Eric Stefan, Cambridge, MA (US); Robert Hilgraf, Cambridge, MA (US)

(73) Assignees: THE BROAD INSTITUTE, INC., Cambridge, MA (US); DANA-FARBER CANCER INSTITUTE, INC., Boston, MA (US)

( * ) Notice: Subject to any disclaimer, the term of this patent is extended or adjusted under 35 U.S.C. 154(b) by 223 days.

(21) Appl. No.: 16/498,897

(22) PCT Filed: Mar. 30, 2018

(86) PCT No.: PCT/US2018/025530
§ 371 (c)(1),
(2) Date: Sep. 27, 2019

(87) PCT Pub. No.: WO2018/183936
PCT Pub. Date: Oct. 4, 2018

(65) Prior Publication Data
US 2022/0096513 A1    Mar. 31, 2022

Related U.S. Application Data

(60) Provisional application No. 62/479,946, filed on Mar. 31, 2017.

(51) Int. Cl.
*A61K 31/7064* (2006.01)
*A61K 31/4439* (2006.01)
*A61K 31/498* (2006.01)

(52) U.S. Cl.
CPC ...... *A61K 31/7064* (2013.01); *A61K 31/4439* (2013.01); *A61K 31/498* (2013.01)

(58) Field of Classification Search
CPC ............ A61K 31/7064; A61K 31/4439; A61K 31/498
See application file for complete search history.

(56) References Cited

U.S. PATENT DOCUMENTS

| 4,866,175 A  * | 9/1989 | Issidorides ........... C07D 241/52 548/309.7 |
| 5,599,812 A | 2/1997 | Rault et al. |
| 8,642,584 B2 | 2/2014 | Aftab et al. |
| 2009/0163545 A1* | 6/2009 | Goldfarb ................ A61K 31/13 514/688 |

FOREIGN PATENT DOCUMENTS

WO    WO-2011028947 A2 *    3/2011    ........... C07D 401/12

OTHER PUBLICATIONS

Ramachandran et al. Med Chem Res (2014) 23:2445-2455 (Year: 2014).*
Storr et al. Nature Reviews Cancer 11.5 (2011): 364-374 (Year: 2011).*
Wang et al. Bioorganic & Medicinal Chemistry Letters 23 (2013) 1253-1256. (Year: 2013).*
Thomas, V. and Balthasar, J. The AAPS Journal, vol. 18, No. 4, Jul. 2016, 923-932. (Year: 2016).*
El Newahie et al. Arch. Pharm. Chem. Life Sci. 2016, 349, 309-326. (Year: 2016).*
Small, D. Semin Hematol. Jul. 2008 ; 45(3 Suppl 2): S17-S21. (Year: 2008).*
Reichert, Janice M., and Julia B. Wenger. "Development trends for new cancer therapeutics and vaccines." Drug discovery today 13.1-2 (2008): 30-37. (Year: 2008).*
Pubchem AID 430, "Fluorescent HTS Cytotoxicity/Cell viability assay (HPDE-C7 cells)", Create Date: Jun. 14, 2006 (Jun. 14, 2006) Date Accessed: Jul. 24, 2018 (Jul. 24, 2018); p. 3, para 2-3.
Pubchem CID 662451, "KXTPLPWPHBUPDZ-UHFFFAOYSA-N", Create Date: Jun. 29, 2005 (Jun. 29, 2005) Date Accessed: Jul. 24, 2018 (Jul. 24, 2018); p. 4 compound listed.
International Search Report and Written Opinion for corresponding PCT Patent Application No. PCT/US18/25530, dated Aug. 6, 2018 (18 pages).

* cited by examiner

*Primary Examiner* — Mina Haghighatian
*Assistant Examiner* — Janice Y Silverman
(74) *Attorney, Agent, or Firm* — Melissa Hunter-Ensor; Scott Goncher; Greenberg Traurig, LLP

(57) ABSTRACT

The present invention includes CSNK1A1 inhibitors that are useful in treating or preventing a cancer in a subject. In certain embodiments, the cancer comprises a hematological cancer, such as but not limited to acute myeloid leukemia (AML) and/or MDS (myelodysplastic syndrome, including 5q-MDS). In other embodiments, the cancer comprises colon cancer.

15 Claims, 4 Drawing Sheets

Specification includes a Sequence Listing.

Compound 1

Compound 1

COMPOUNDS AND METHODS USEFUL FOR TREATING OR PREVENTING CANCERS

CROSS REFERENCE TO RELATED APPLICATIONS

The present application is the U.S. national phase application, pursuant to 35 U.S.C. § 371, of PCT International Application Ser. No.: PCT/US2018/025530, filed Mar. 30, 2018, designating the United States and published in English, which claims priority to U.S. Provisional Application Ser. No. 62/479,946, filed Mar. 31, 2017, the contents of which are hereby incorporated by reference in their entirety.

STATEMENT OF RIGHTS TO INVENTIONS MADE UNDER FEDERALLY SPONSORED RESEARCH

This invention was made with government support under grant No. 3U54HG006093-03 awarded by NIH/NHGRI. The government has certain rights in the invention.

SEQUENCE LISTING

The instant application contains a Sequence Listing which has been submitted electronically in ASCII format and is hereby incorporated by reference in its entirety. Said ASCII copy, created on Sep. 24, 2020, is named 167741_016402_US_SL.txt and is 779 bytes in size.

BACKGROUND OF THE INVENTION

The myelodysplastic syndromes (also known as MDS or myelodysplasia) are a group of hematological medical conditions characterized by ineffective production ("dysplasia") of blood cells. The MDS are disorders of the hematopoietic stem cells in the bone marrow, with afflicted patients displaying disorderly and ineffective hematopoiesis. The number and quality of blood-forming cells decline irreversibly over time, further impairing blood production. MDS patients often develop severe anemia and require blood transfusions. In some cases, patients develop cytopenias (low blood counts) caused by progressive bone marrow failure.

MDS include the following exemplary diseases: Refractory cytopenia with unilineage dysplasia (refractory anemia, refractory neutropenia, and refractory thrombocytopenia); Refractory anemia with ring sideroblasts (RARS), and Refractory anemia with ring sideroblasts-thrombocytosis (RARS-t); Refractory cytopenia with multilineage dysplasia (RCMD); Refractory anemias with excess blasts I and II; 5q-syndrome (typically seen in older women with normal or high platelet counts and isolated deletions of the long arm of chromosome 5 in bone marrow cells); Myelodysplasia unclassifiable; and Refractory cytopenia of childhood.

MDS signs and symptoms are nonspecific and generally related to the blood cytopenias: anemia (low red blood cell count or reduced hemoglobin); neutropenia (low neutrophil count); and thrombocytopenia (low platelet count). However, many individuals are asymptomatic, and blood abnormalities are identified as a part of a routine blood count exam.

Leukemia is a group of cancers that usually begin in the bone marrow and result in high numbers of abnormal white blood cells, which are not fully developed and are called blasts or leukemia cells. Symptoms may include bleeding and bruising problems, feeling tired, fever, and an increased risk of infections, all of which relate to the lack of normal white blood cells. The exact cause of leukemia is unknown, with many kinds of leukemia being associated with inherited and environmental factors. There are four main types of leukemia: acute lymphoblastic leukemia (ALL), acute myeloid leukemia (AML), chronic lymphocytic leukemia (CLL) and chronic myeloid leukemia (CML).

Treatment of leukemias may involve a combination of chemotherapy, radiation therapy, targeted therapy, and bone marrow transplant, in addition to supportive care and palliative care as needed. Treatment success depends on the type of leukemia and the age of the person, with an average five-year survival rate of 57% in the U.S. Leukemia is the most common type of cancer in children, with three quarters of leukemia cases in children being ALL. On the other hand, AML and CLL are most common in adults.

There is a need in the art to identify compounds that can be used to treat or prevent a cancer, such as but not limited to leukemia (including ALL, AML, CLL and CML), myelodysplastic syndrome (MDS, including 5q-MDS) and/or colon cancer, in a subject in need thereof.

SUMMARY OF THE INVENTION

As described below, the present invention generally provides compounds that can be used to treat or prevent certain types of cancer in a subject in need thereof. In certain embodiments, the compounds contemplated within the invention are selective inhibitors of casein kinase 1 (CSNK1). In other embodiments, the compounds contemplated within the invention inhibit at least one kinase selected from the group consisting of casein kinase 1 alpha 1 (CSNK1A1), casein kinase 1 delta (CSNK1D) and casein kinase 1 epsilon (CSNK1E).

The invention provides a method of treating or preventing a cancer in a subject in need thereof. In certain embodiments, the cancer comprises a hematological cancer, such as but not limited to MDS and/or AML. In other embodiments, the cancer comprises colon cancer. In some embodiments, the invention provides a method of treating a cancer in a subject in need thereof.

In various embodiments of any of the above aspects or any other aspects of the invention delineated herein, the method comprises administering to the subject in need thereof a therapeutically effective amount of at least one compound, or salt or N-oxide thereof, selected from the group consisting of: a compound of formula (I):

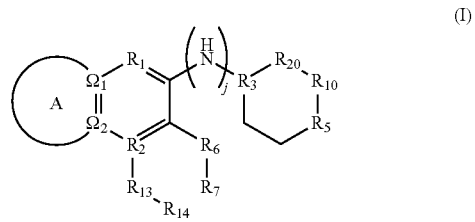

wherein:
"j" is 0 or 1;
$R_1$ is selected from the group consisting of N, C—H, C—F and C—OH, where at least one of $R_1$ and $R_2$ is N;
$R_2$ is selected from the group consisting of N (i.e. $R_{13}$ is absent), C—H (i.e. $R_{13}$ is absent), C—F (i.e. $R_{13}$ is absent), C—OH (i.e. $R_{13}$ is absent), and C,
$R_3$ is selected from the group consisting of N, CH, CF and COH;

$R_5$ is selected from the group consisting of N(H), N($C_1$-$C_6$ alkyl), C(H)—$NH_2$, C(H)—NH($C_1$-$C_6$ alkyl), C(H)—($C_1$-$C_6$ alkyl)-$NH_2$, C(H)—C(=O)—$NH_2$, and C(H)—N($C_1$-$C_6$ alkyl)($C_1$-$C_6$ alkyl);

one of $R_6$ or $R_7$ is absent (i.e., it is a bond) and the other of $R_6$ or $R_{13}$ is selected from the group consisting of —C(H)(CN)—, —C(H)(C≡CH)—, —$CH_2$—, —C(H)($CH_3$)—, —C($CH_3$)(CN)—, —N(CN)—, and —NH—; where $R_7$ is hydrogen when $R_6$ is absent, and where $R_{14}$ is hydrogen when $R_{13}$ is absent;

$R_7$ and $R_{14}$ are independently selected from the group consisting of —C(=O)O$R_8$, —C(=O)N($R_9$)$R_8$, —C(=O)N(H)$R_8$, —NHC(=O)$R_8$, —C(=O)C($R_9$)=C($R_9$)($R_9$), $N^1$—$R_8$-1H-imidazol-2-yl, —$CH_2$O$R_8$, and 2-$R_8$-1,3,5-oxadiazol-5-yl;

$R_{10}$ and $R_{20}$ are independently selected from the group consisting of C(H)($R_{12}$), C($R_{12}$)($R_{12}$), and C(=O);

each occurrence of $R_8$ is independently selected from the group consisting of H, $C_1$-$C_6$ alkyl, aryl, $C_3$-$C_8$ cycloalkyl, $C_3$-$C_8$ cycloalkyl-($C_1$-$C_3$)alkyl, $C_3$-$C_8$ heterocycloalkyl-($C_1$-$C_3$)alkyl, aryl-($C_1$-$C_3$)alkyl, ($C_1$-$C_6$) hydroxyalkyl, imidazol-2-yl optionally substituted with methyl, and oxadiazol-5-yl optionally substituted with methyl or benzyl;

each occurrence of $R_9$ is independently selected from the group consisting of H, $C_1$-$C_6$ alkyl, aryl, and halogen;

each occurrence of $R_{12}$ is independently selected from the group consisting of H, $C_1$-$C_6$ alkyl, aryl, ($C_1$-$C_6$) hydroxyalkyl, $C_3$-$C_8$ cycloalkyl-($C_1$-$C_3$)alkyl, —C(=O)O—($C_1$-$C_6$) alkyl;

moiety "A" is selected from the group consisting of:

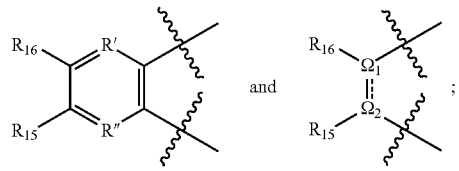

wherein R' and R" are independently selected from the group consisting of N, C—H, C—F, and C—$R_{17}$;

$\Omega_1$ and $\Omega_2$ are independently selected at each occurrence from C, CH, and N and the dashed ("----") bond is a double bond or single bond;

$R_{15}$, $R_{16}$, and $R_{17}$ are independently selected at each occurrence from hydrogen, aryl, halo, amino and nitro; and each alkyl, aryl, arylalkyl, heterocycloalkylalkyl, cycloalkylalkyl, and/or cycloalkyl group is independently optionally substituted with at least one selected from the group consisting of $C_1$-$C_6$ alkyl, halo, hydroxy, alkoxy, amino, monoalkylamino, dialkylamino, aminocarbonyl, acylamino, carboxy, alkoxycarbonyl, sulfanyl, sulfinyl, sulfonyl, and sulfonamide; and, each aryl and/or aryl($C_1$-$C_3$)alkyl group is independently optionally substituted with at least one selected from the group consisting of $C_1$-$C_6$ alkyl, $C_2$-$C_6$ alkenyl, $C_2$-$C_6$ alkynyl, aryl, heterocyclyl, heteroaryl, halo, haloalkyl (including trifluoromethyl), —SR, —S(=O)($C_1$-$C_6$ alkyl), —S(=O)$_2$($C_1$-$C_6$ alkyl), —S(=O)$_2$NRR, —OH, —OR, —C(=O)R, —O—C(=O)R, —C(=O)OR, —OC(=O)O($C_1$-$C_6$ alkyl), —NRR, —C(=O)NRR, —N(R)C(=O)R, —C(=NR)NRR, —P(=O)(OR)$_2$, cyano and nitro; wherein each R is independently selected from the group consisting of H, alkyl, heteroalkyl, cycloalkyl, aryl, heterocyclyl, and heteroaryl.

In certain embodiments, the compound of formula (I) is the compound of formula (Ib), or a salt or N-oxide thereof:

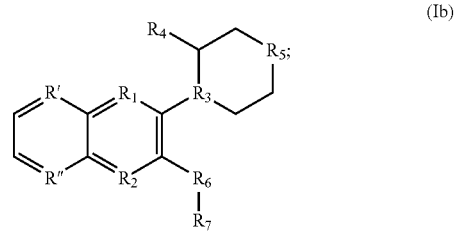

wherein $R_4$ is selected from the group consisting of H, CN and $CH_3$.

In certain embodiments, the compound of formula (I) is the compound of formula (Ic), or a salt or N-oxide thereof:

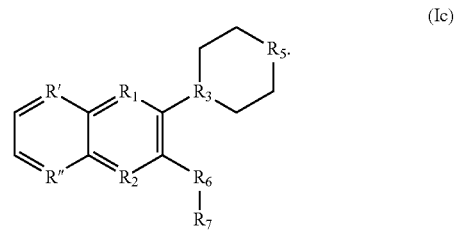

In certain embodiments, the compound of formula (I) is the compound of formula (Id), or a salt or N-oxide thereof:

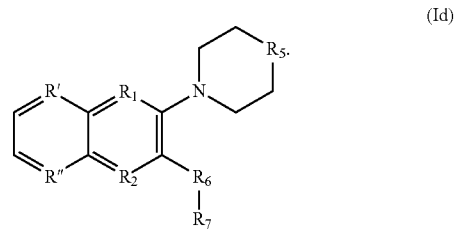

In certain embodiments, the compound of formula (I) is the compound of formula (Id), or a salt or N-oxide thereof, wherein $R_5$ is NH or N($C_1$-$C_6$ alkyl).

In certain embodiments, the compound of formula (I) is the compound of formula (Ie), or a salt or N-oxide thereof:

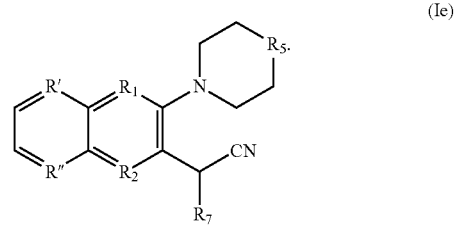

In certain embodiments, the compound of formula (I) is the compound of formula (Ie), or a salt or N-oxide thereof, wherein $R_7$ is selected from the group consisting of —C(=O)O$R_8$, —C(=O)N($R_9$)$R_8$, and —C(=O)C($R_9$)=C($R_9$)$_2$.

In certain embodiments, R' and R" are both CH.

In certain embodiments, $R_1$ and $R_2$ are both N.

In certain embodiments, $R_1$ is N and $R_2$ is C—H. In other embodiments, $R_1$ is N and $R_2$ is C—F. In yet other embodiments, $R_1$ is N and $R_2$ is C—OH.

In certain embodiments, $R_2$ is N and $R_1$ is C—H. In other embodiments, $R_2$ is N and $R_1$ is C—F. In yet other embodiments, $R_2$ is N and $R_1$ is C—OH.

In some embodiments, the compound has the structure of formula (If), or a salt or N-oxide thereof:

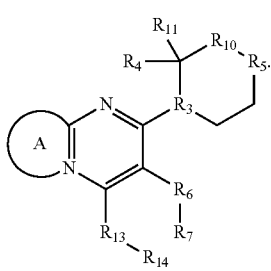

(If)

wherein $R_4$ and $R_{11}$ are independently selected from the group consisting of H, CN and $CH_3$.

In some embodiments, the compound has the structure of formula (Ig), or a salt or N-oxide thereof:

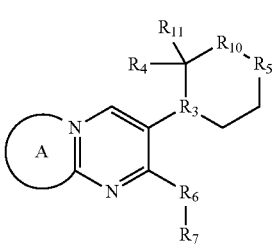

(Ig)

wherein $R_4$ and $R_{11}$ are independently selected from the group consisting of H, CN and $CH_3$.

In some embodiments, the compound has the structure of formula (Ih), or a salt or N-oxide thereof:

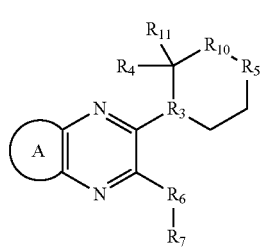

(Ih)

wherein $R_4$ and $R_{11}$ are independently selected from the group consisting of H, CN and $CH_3$.

In some embodiments, the compound has the structure of formula (Ii), or a salt or N-oxide thereof:

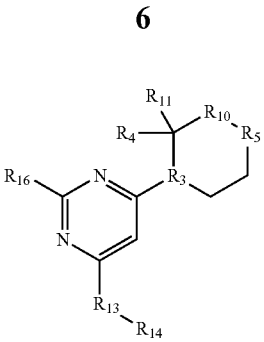

(Ii)

wherein $R_4$ and $R_{11}$ are independently selected from the group consisting of H, CN and $CH_3$.

In some embodiments, the compound has the structure of formula (Ij), or a salt or N-oxide thereof:

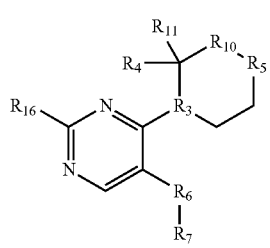

(Ij)

wherein $R_4$ and $R_{11}$ are independently selected from the group consisting of H, CN and $CH_3$.

In some embodiments, the compound has the structure of formula (Ik), or a salt or N-oxide thereof:

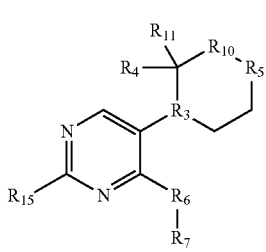

(Ik)

wherein $R_4$ and $R_{11}$ are independently selected from the group consisting of H, CN and $CH_3$.

In some embodiments, the compound has the structure of formula (Il), or a salt or N-oxide thereof:

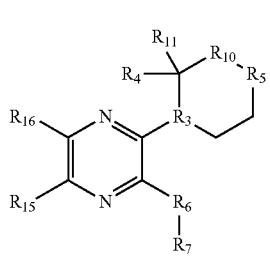

(Il)

wherein $R_4$ and $R_{11}$ are independently selected from the group consisting of H, CN and $CH_3$.

In some embodiments, the compound has the structure of formula (Im) or (In), or a salt or N-oxide thereof:

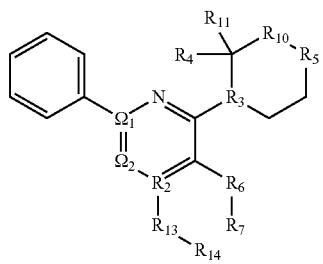

(Im)

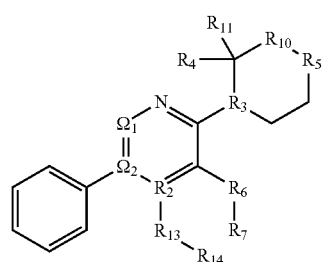

(In)

wherein $R_4$ and $R_{11}$ are independently selected from the group consisting of H, CN and $CH_3$. In some embodiments, the phenyl group attached to $\Omega_1$ or $\Omega_2$ in formulas (Im) or (In), respectively is substituted one or more times (e.g., one, two, three, four, five, etc.) with halogen (e.g., fluoro, chloro, etc.), nitro, alkyl, or hydroxy.

In various embodiments of any of the above aspects or any other aspects of the invention delineated herein, the compound of formula (I), or a salt or N-oxide thereof, is selected from the group consisting of:

cyclohexyl 2-cyano-2-(3-(4-ethylpiperazin-1-yl)quinoxalin-2-yl)acetate (compound 1)

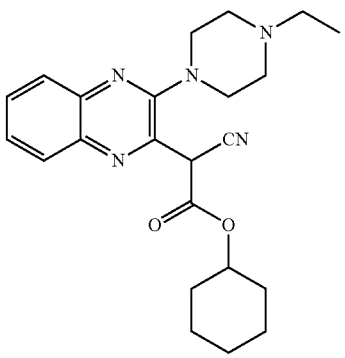

benzyl 2-cyano-2-(3-(4-methylpiperazin-1-yl)quinoxalin-2-yl)acetate (compound 2)

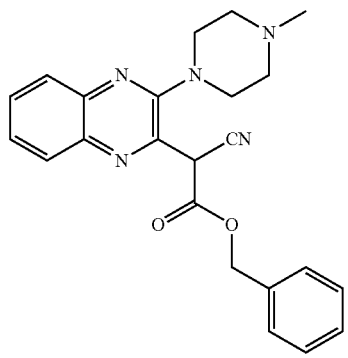

2-ethylbutyl 2-cyano-2-(3-(4-ethylpiperazin-1-yl)quinoxalin-2-yl)acetate (compound 3)

;

cyclohexyl 2-cyano-2-(3-(4-methylpiperazin-1-yl)quinoxalin-2-yl)acetate (compound 4)

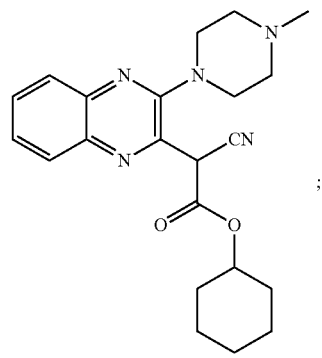 [SMILES: CN1CCN(c2nc3ccccc3nc2C(C#N)C(=O)OC2CCCCC2)CC1]

;

isopropyl 2-cyano-2-(3-(4-methylpiperazin-1-yl)quinoxa-lin-2-yl)acetate (compound 5)

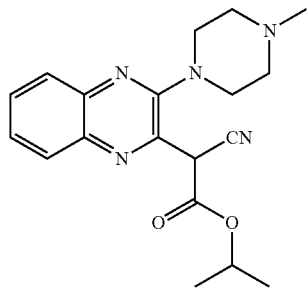

N-benzyl-2-cyano-2-(3-(4-methylpiperazin-1-yl)quinoxa-lin-2-yl)acetamide

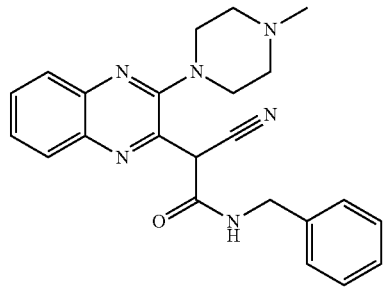

benzyl 2-(3-(4-methylpiperazin-1-yl)quinoxalin-2-yl)but-3-ynoate

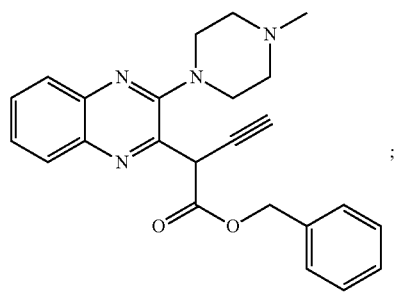 [SMILES: C#CC(C(=O)OCc1ccccc1)c1nc2ccccc2nc1N1CCN(C)CC1]

1-phenylethyl 2-cyano-2-(3-(4-methylpiperazin-1-yl)qui-noxalin-2-yl)acetate

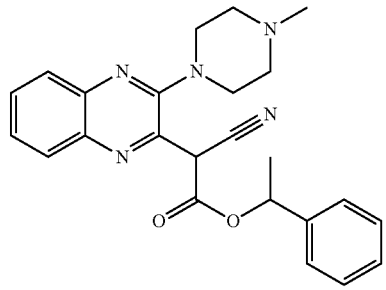

benzyl 2-(3-(4-methylpiperazin-1-yl)quinoxalin-2-yl)propanoate

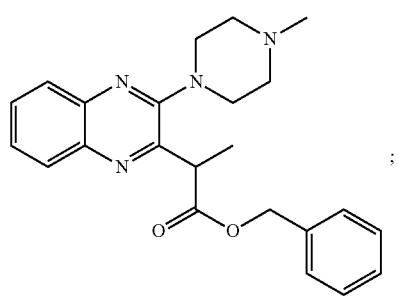 [SMILES: CC(C(=O)OCc1ccccc1)c1nc2ccccc2nc1N1CCN(C)CC1]

2-phenylpropan-2-yl 2-cyano-2-(3-(4-methylpiperazin-1-yl)quinoxalin-2-yl)acetate

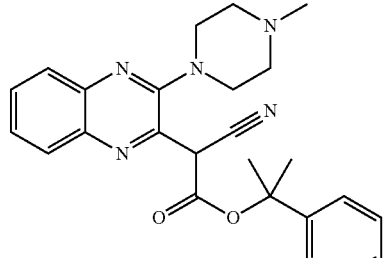

benzyl 2-cyano-2-(3-(4-methylpiperazin-1-yl)quinoxalin-2-yl)propanoate

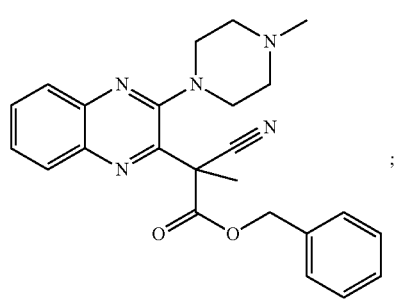 [SMILES: CN1CCN(c2nc3ccccc3nc2C(C)(C#N)C(=O)OCc2ccccc2)CC1]

3-hydroxy-2-(3-(4-methylpiperazin-1-yl)quinoxalin-2-yl)propanenitrile

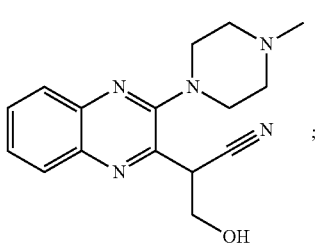 [SMILES: CN1CCN(c2nc3ccccc3nc2C(C#N)CO)CC1]

| 11 | 12 |
|---|---|
| 3-methoxy-2-(3-(4-methylpiperazin-1-yl)quinoxalin-2-yl)propanenitrile | 1-(3-(4-methylpiperazin-1-yl)quinoxalin-2-yl)but-3-en-2-one |

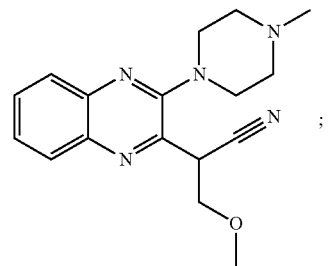 [SMILES: COCC(C#N)c1nc2ccccc2nc1N1CCN(C)CC1]

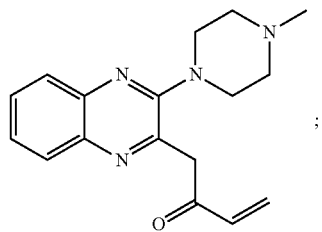

3-(benzyloxy)-2-(3-(4-methylpiperazin-1-yl)quinoxalin-2-yl)propanenitrile

N-(3-(4-methylpiperazin-1-yl)quinoxalin-2-yl)acrylamide

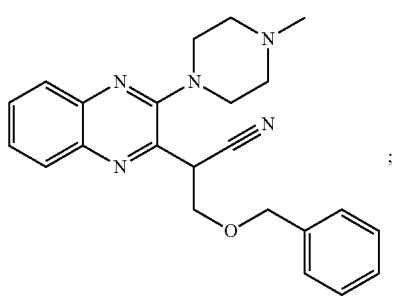 [SMILES: CN1CCN(c2nc3ccccc3nc2C(C#N)COCc2ccccc2)CC1]

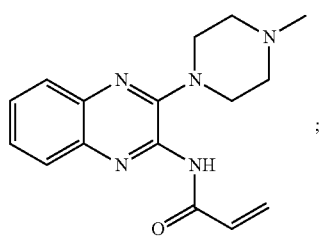

N-(cyano(3-(4-methylpiperazin-1-yl)quinoxalin-2-yl)methyl)-2-phenylacetamide benzyl 2-(3-(2-cyano-4-methylpiperazin-1-yl)quinoxalin-2-yl)acetate

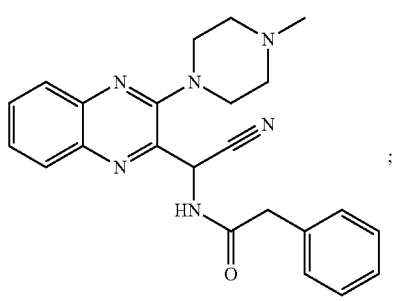 [SMILES: CN1CCN(c2nc3ccccc3nc2C(C#N)NC(=O)Cc2ccccc2)CC1]

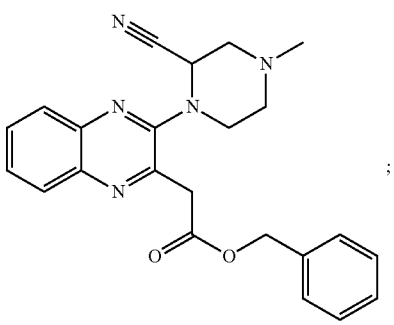

benzyl N-cyano(3-(4-methylpiperazin-1-yl)quinoxalin-2-yl)carbamate benzyl 2-cyano-2-(3-(2,4-dimethylpiperazin-1-yl)quinoxalin-2-yl)acetate

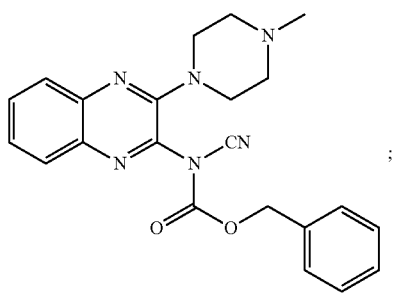 [SMILES: CN1CCN(c2nc3ccccc3nc2N(C#N)C(=O)OCc2ccccc2)CC1]

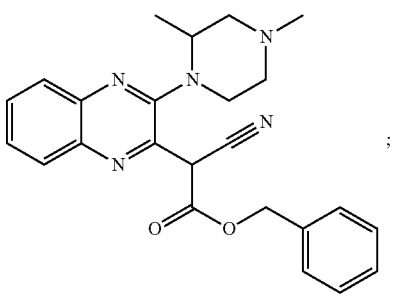 [SMILES: CC1CN(C)CCN1c1nc2ccccc2nc1C(C#N)C(=O)OCc1ccccc1]

benzyl 2-cyano-2-(3-(1-methylpiperidin-4-yl)quinoxalin-2-yl)acetate

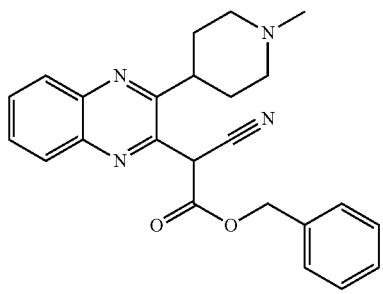

benzyl 2-(3-(4-aminopiperidin-1-yl)quinoxalin-2-yl)-2-cyanoacetate

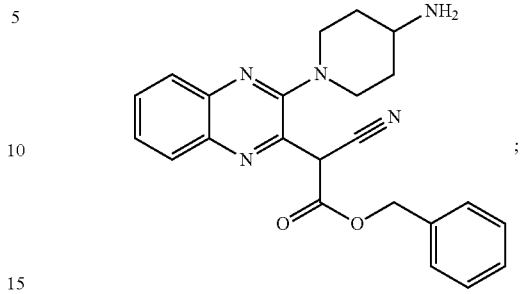

benzyl 2-cyano-2-(3-(4-fluoro-1-methylpiperidin-4-yl)quinoxalin-2-yl)acetate

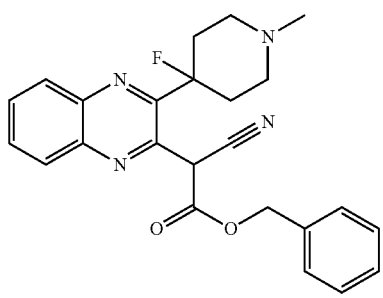

benzyl 2-cyano-2-(3-(4-(methylamino)piperidin-1-yl)quinoxalin-2-yl)acetate

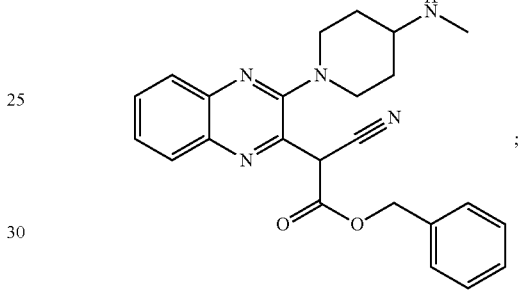

benzyl 2-cyano-2-(3-(4-hydroxy-1-methylpiperidin-4-yl)quinoxalin-2-yl)acetate

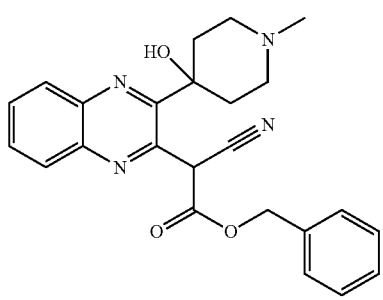

benzyl 2-cyano-2-(3-(4-(dimethylamino)piperidin-1-yl)quinoxalin-2-yl)acetate

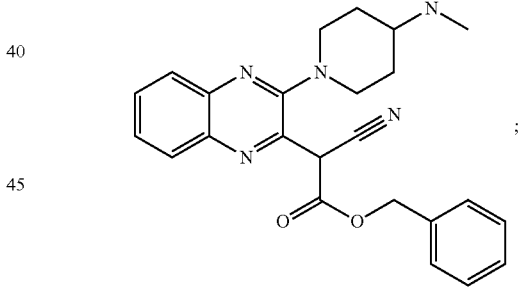

N-(cyano(3-(4-methylpiperazin-1-yl)quinoxalin-2-yl)methyl)acetamide

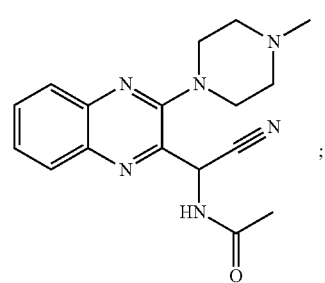 [SMILES: CC(=O)NC(C#N)c1nc2ccccc2nc1N1CCN(C)CC1]

2-(1-benzyl-1H-imidazol-2-yl)-2-(3-(4-methylpiperazin-1-yl)quinoxalin-2-yl)acetonitrile

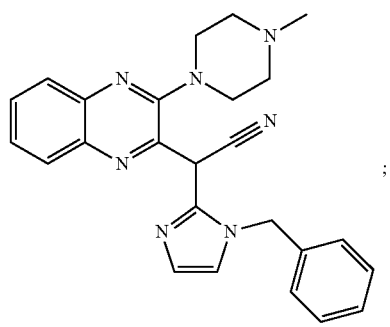 [SMILES: CN1CCN(c2nc3ccccc3nc2C(C#N)c2nccn2Cc2ccccc2)CC1]

2-(1-methyl-1H-imidazol-2-yl)-2-(3-(4-methylpiperazin-1-yl)quinoxalin-2-yl)acetonitrile

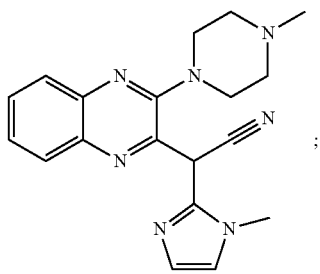 [SMILES: CN1CCN(c2nc3ccccc3nc2C(C#N)c2nccn2C)CC1]

2-(5-benzyl-1,3,4-oxadiazol-2-yl)-2-(3-(4-methylpiperazin-1-yl)quinoxalin-2-yl)acetonitrile

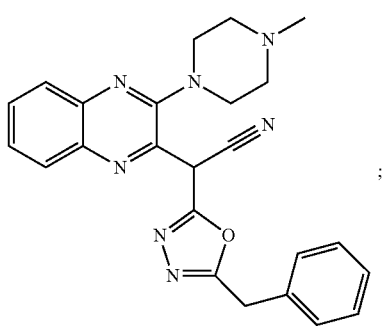 [SMILES: CN1CCN(c2nc3ccccc3nc2C(C#N)c2nnc(Cc3ccccc3)o2)CC1]

2-(5-methyl-1,3,4-oxadiazol-2-yl)-2-(3-(4-methylpiperazin-1-yl)quinoxalin-2-yl)acetonitrile

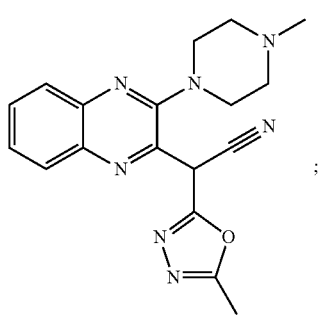 [SMILES: Cc1nnc(C(C#N)c2nc3ccccc3nc2N2CCN(C)CC2)o1]

benzyl 2-cyano-2-(3-(4-methylpiperazin-1-yl)quinolin-2-yl)acetate

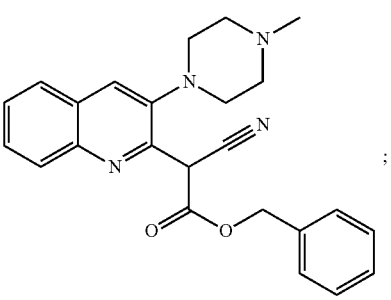 [SMILES: CN1CCN(c2cc3ccccc3nc2C(C#N)C(=O)OCc2ccccc2)CC1]

benzyl 2-cyano-2-(2-(4-methylpiperazin-1-yl)quinolin-3-yl)acetate

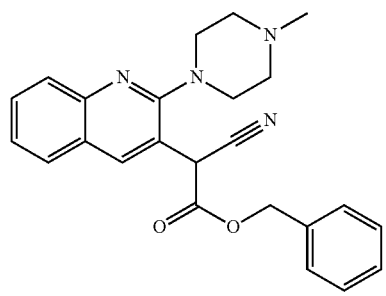

benzyl 2-cyano-2-(2-(4-methylpiperazin-1-yl)-1,5-naphthyridin-3-yl)acetate

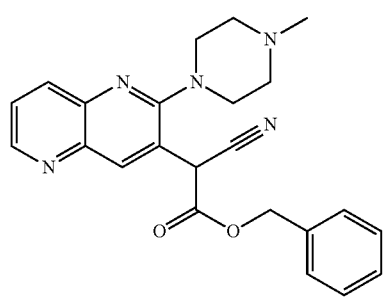

benzyl 2-cyano-2-(3-(4-methylpiperazin-1-yl)-1,5-naphthyridin-2-yl)acetate

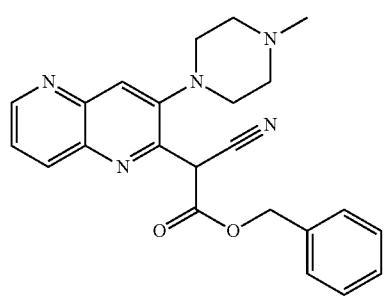

benzyl 2-cyano-2-(2-(4-methylpiperazin-1-yl)-4-oxo-1,4-dihydroquinolin-3-yl)acetate

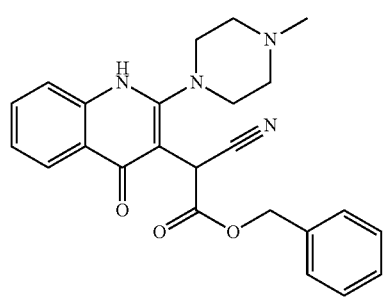

benzyl 2-cyano-2-(3-(4-methylpiperazin-1-yl)-4-oxo-1,4-dihydroquinolin-2-yl)acetate

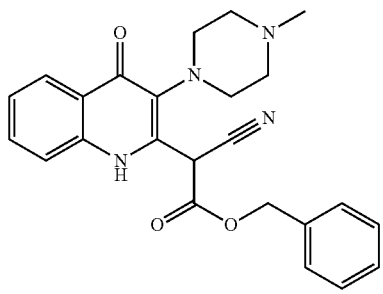

benzyl 2-cyano-2-(5,6-dimethyl-3-(4-methylpiperazin-1-yl)pyrazin-2-yl)acetate

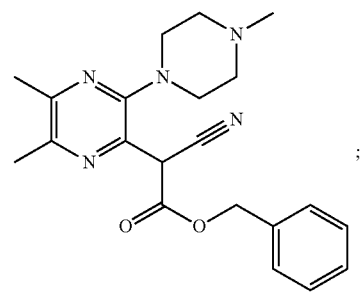 [SMILES: Cc1nc(C(C#N)C(=O)OCc2ccccc2)c(N2CCN(C)CC2)nc1C]

benzyl 2-cyano-2-(3-(4-methylpiperazin-1-yl)pyrazin-2-yl)acetate

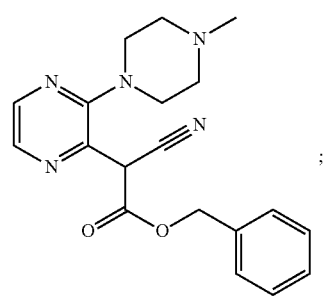 [SMILES: CN1CCN(c2nccnc2C(C#N)C(=O)OCc2ccccc2)CC1]

benzyl 2-cyano-2-(4-fluoro-3-(4-methylpiperazin-1-yl)quinolin-2-yl)acetate

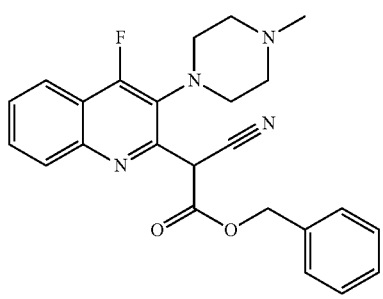

benzyl 2-cyano-2-(4-fluoro-2-(4-methylpiperazin-1-yl)quinolin-3-yl)acetate

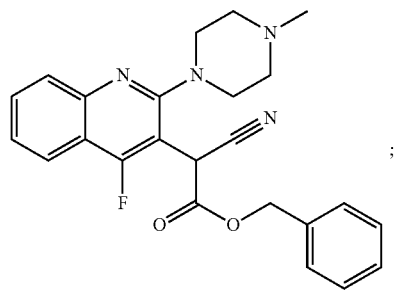 [SMILES: CN1CCN(c2nc3ccccc3c(F)c2C(C#N)C(=O)OCc2ccccc2)CC1]

4-fluorobenzyl 2-cyano-2-(3-(4-(methylpiperazin-1-yl)quinoxalin-2-yl)acetate

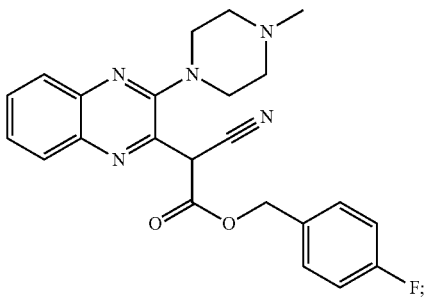 [SMILES: CN1CCN(c2nc3ccccc3nc2C(C#N)C(=O)OCc2ccc(F)cc2)CC1]

2-ethylbutyl 2-cyano-2-(3-(4-(methylpiperazin-1-yl)quinoxalin-2-yl)acetate

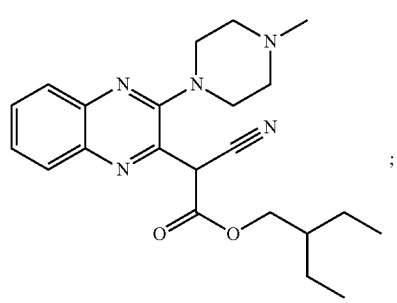 [SMILES: CCC(CC)COC(=O)C(C#N)c1nc2ccccc2nc1N1CCN(C)CC1]

2-ethylbutyl 2-cyano-2-(3-(4-(piperazin-1-yl)quinoxalin-2-yl)acetate

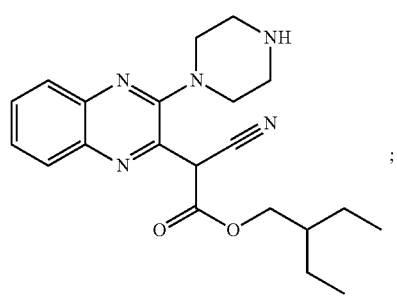 [SMILES: CCC(CC)COC(=O)C(C#N)c1nc2ccccc2nc1N1CCNCC1]

2,2 dimethyl propyl 2-cyano-2-(3-(4-(piperazin-1-yl)qui-
noxalin-2-yl)acetate

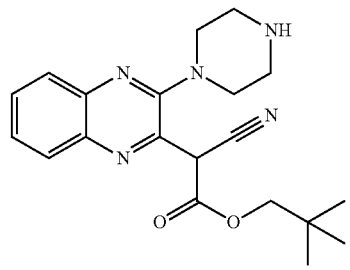

2,2 dimethyl propyl 2-cyano-2-(3-(4-(methylpiperazin-1-yl)
quinoxalin-2-yl)acetate

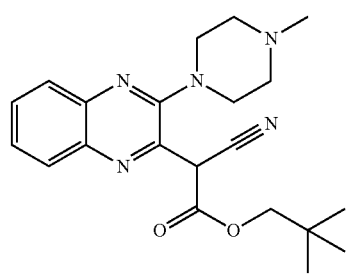

2-fluorobenzyl 2-cyano-2-(3-(4-(piperazin-1-yl)quinoxalin-
2-yl)acetate

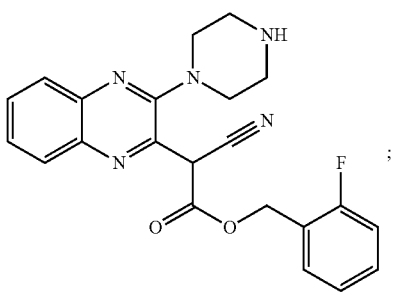 [SMILES: N#CC(C(=O)OCc1ccccc1F)c1nc2ccccc2nc1N1CCNCC1]

3-fluorobenzyl 2-cyano-2-(3-(4-(piperazin-1-yl)quinoxalin-
2-yl)acetate

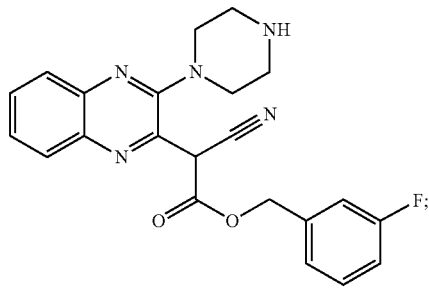 [SMILES: N#CC(C(=O)OCc1cccc(F)c1)c1nc2ccccc2nc1N1CCNCC1]

4-fluorobenzyl 2-cyano-2-(3-(4-(piperazin-1-yl)quinoxalin-
2-yl)acetate

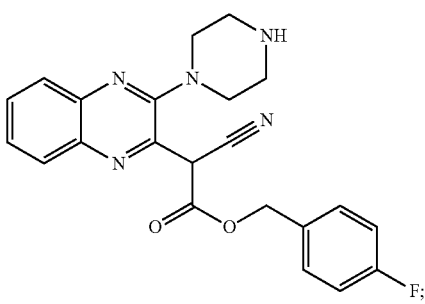 [SMILES: N#CC(C(=O)OCc1ccc(F)cc1)c1nc2ccccc2nc1N1CCNCC1]

3-aminobenzyl 2-cyano-2-(3-(4-(piperazin-1-yl)quinoxalin-
2-yl)acetate

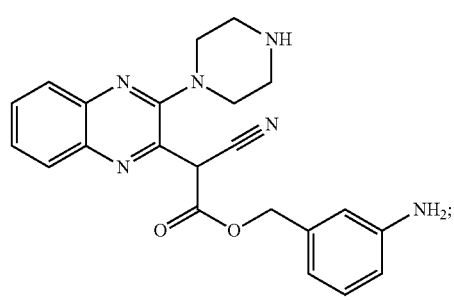 [SMILES: N#CC(C(=O)OCc1cccc(N)c1)c1nc2ccccc2nc1N1CCNCC1]

2-ethylbutyl 2-cyano-2-(3-(4-(amino)piperidin-1-yl)qui-
noxalin-2-yl)acetate

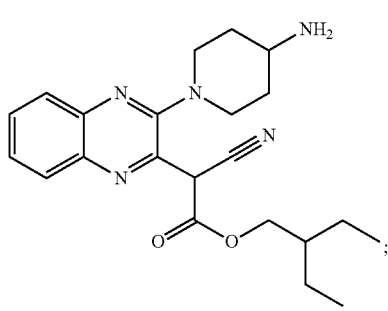 [SMILES: CCC(CC)COC(=O)C(C#N)c1nc2ccccc2nc1N1CCC(N)CC1]

and
2-ethylbutyl 2-cyano-2-(3-(4-(aminomethyl)piperidin-1-yl)
quinoxalin-2-yl)acetate

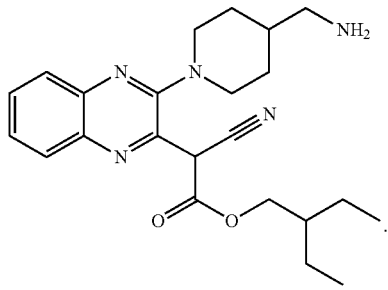 [SMILES: CCC(CC)COC(=O)C(C#N)c1nc2ccccc2nc1N1CCC(CN)CC1]

In some embodiments, the compound has the structure of:
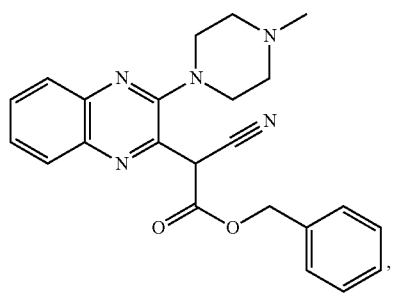
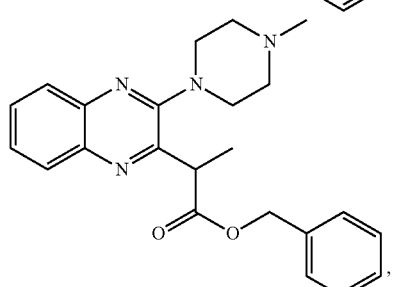
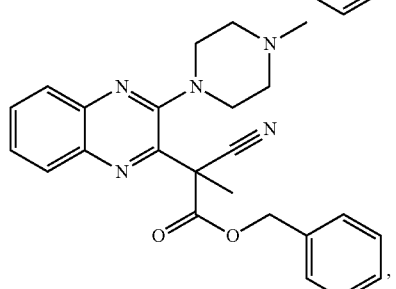
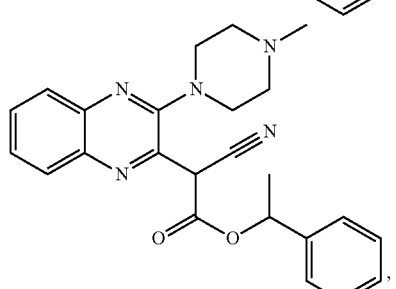
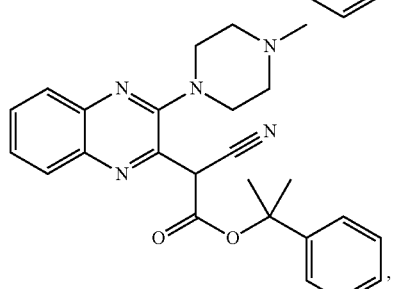
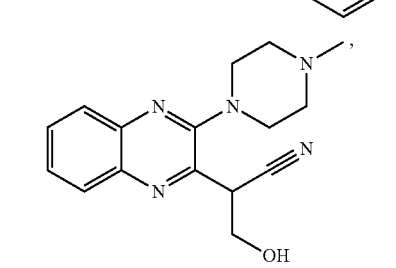
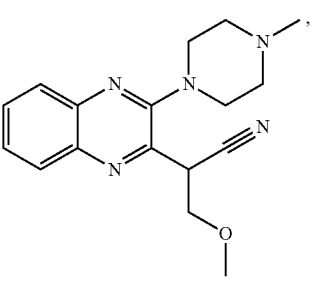
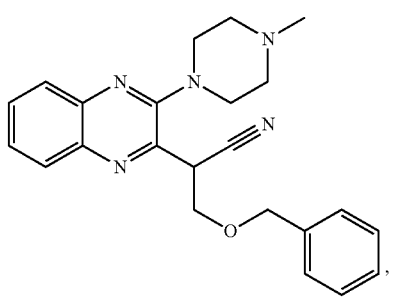
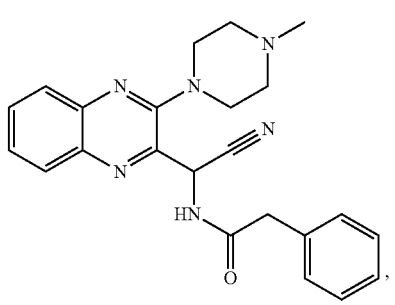
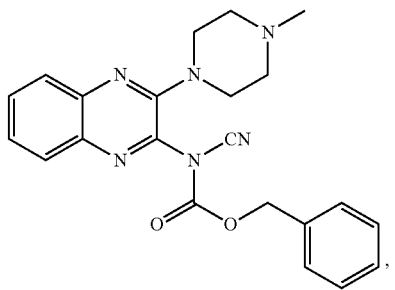
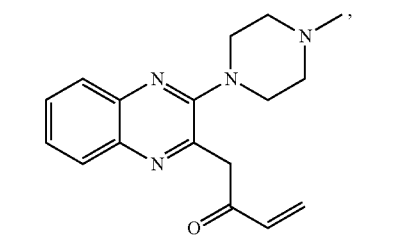
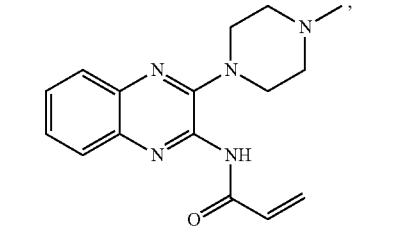

23
-continued
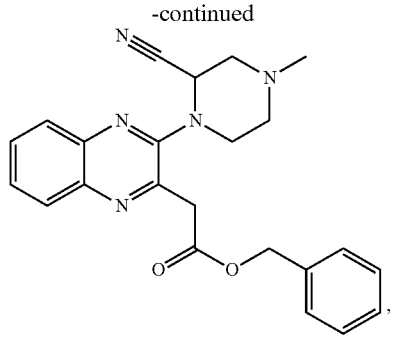
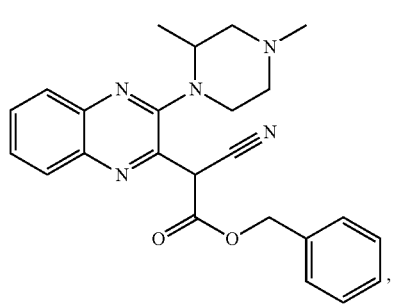
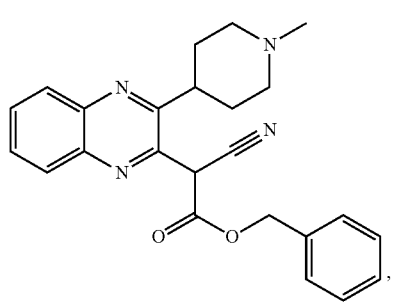
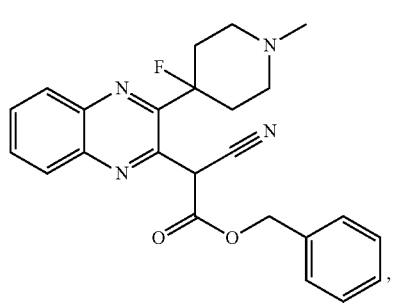
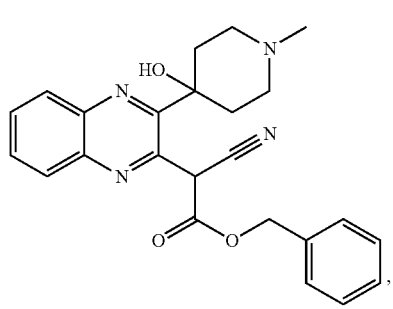
24
-continued
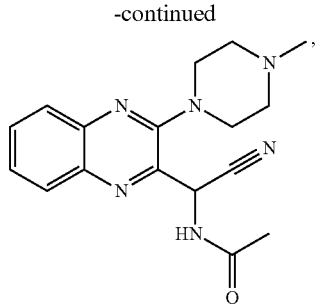
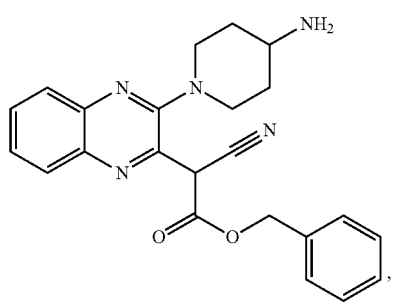
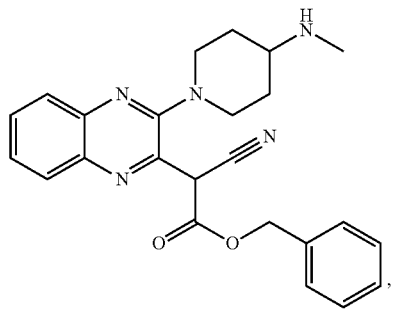
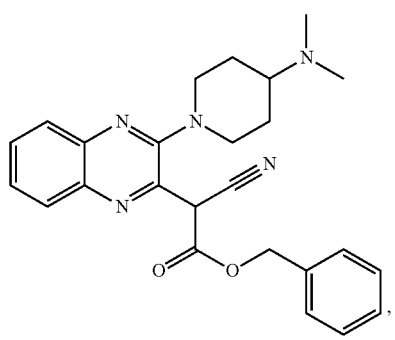
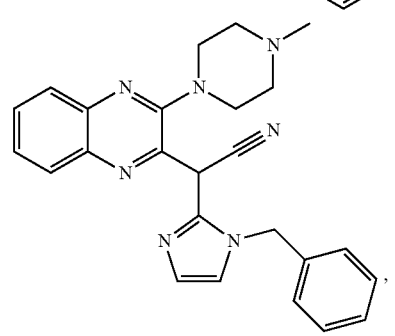

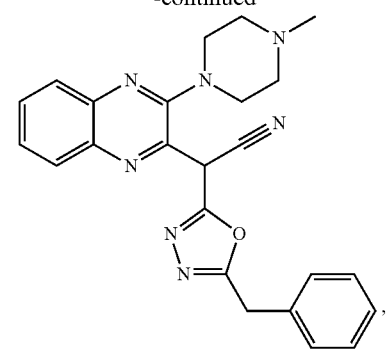
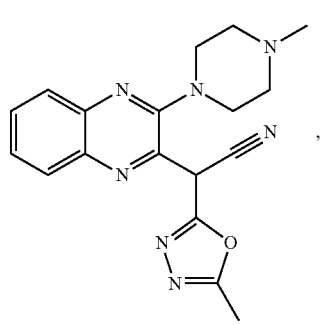
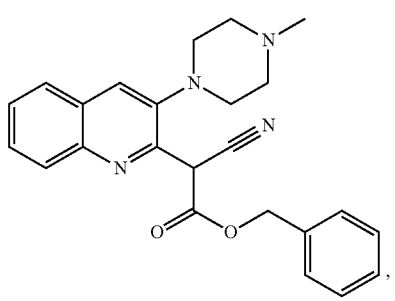
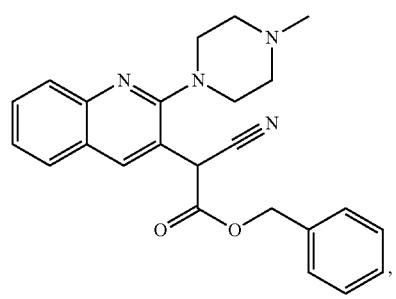
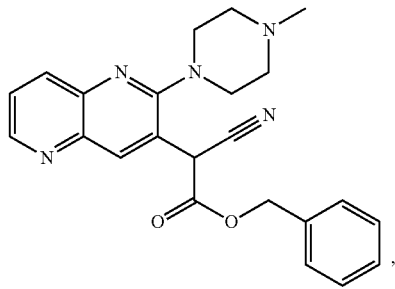
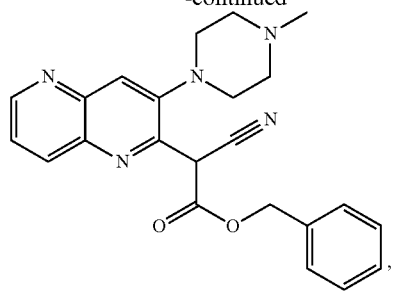
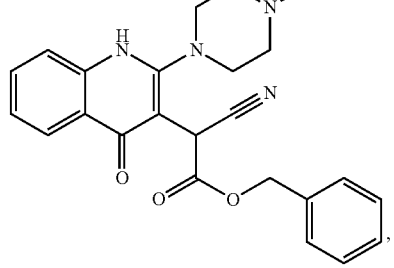
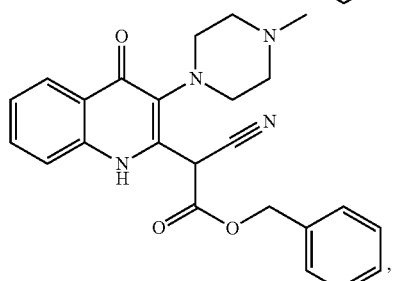
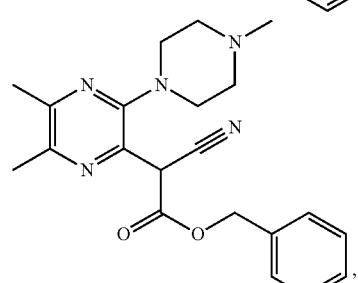
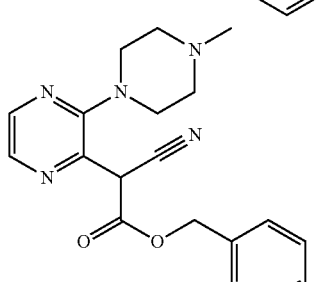
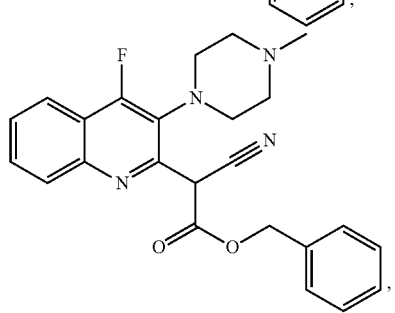

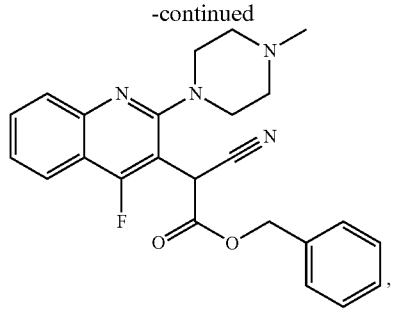
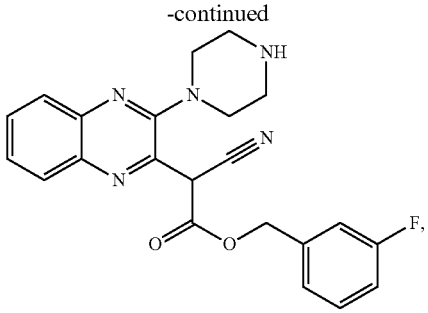
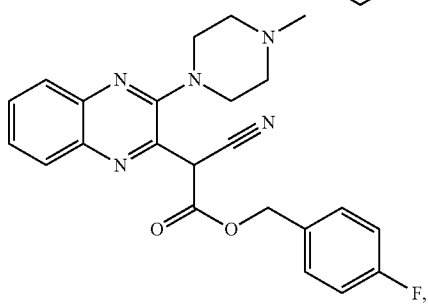
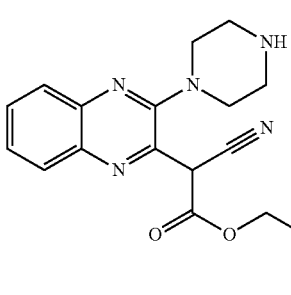
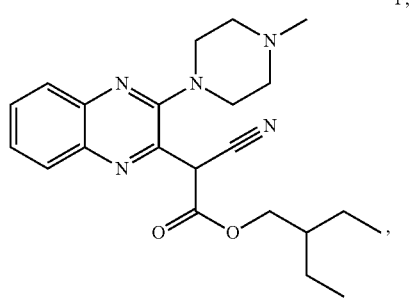
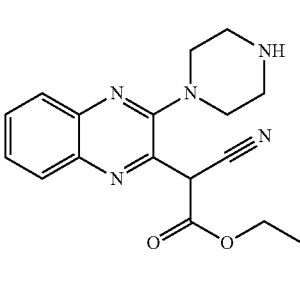
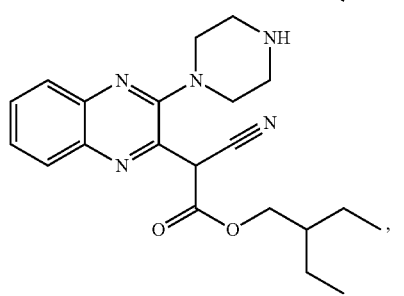
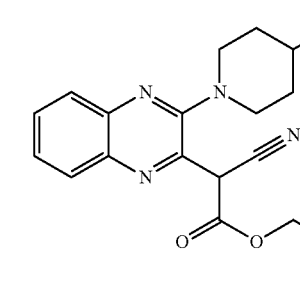
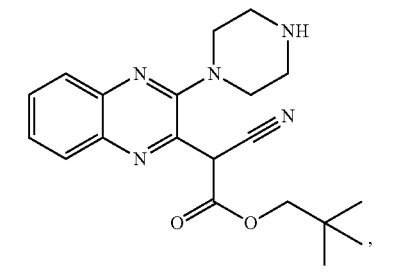
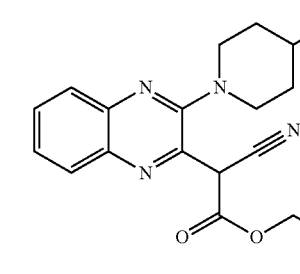
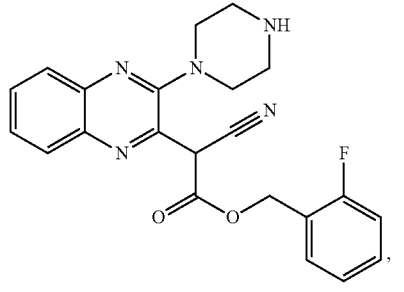
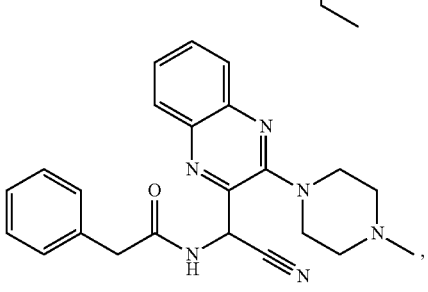

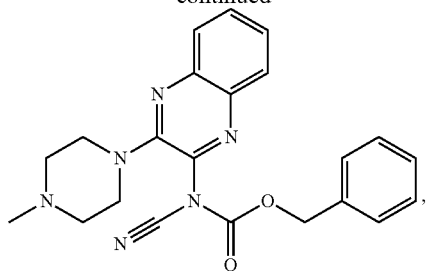
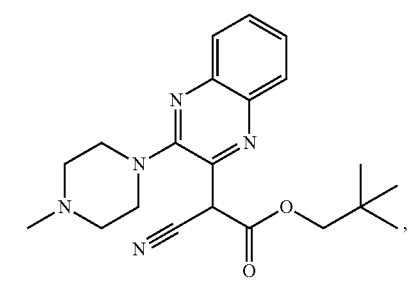
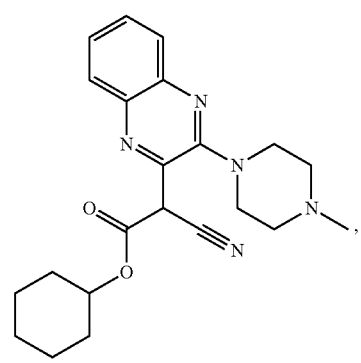
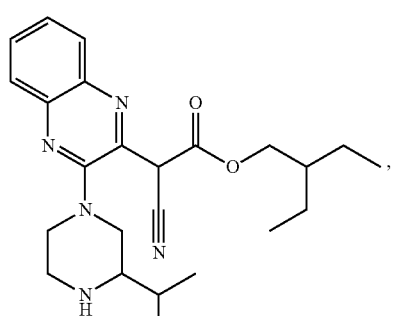
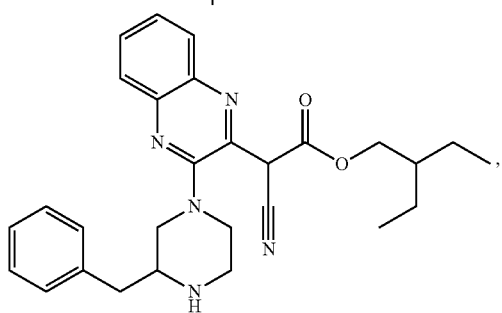
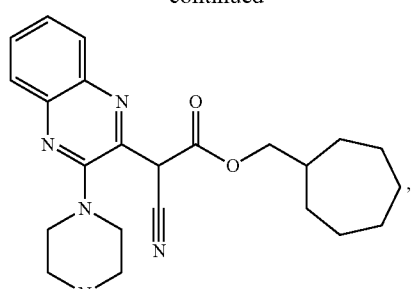
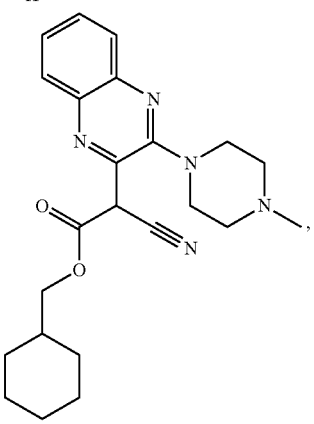
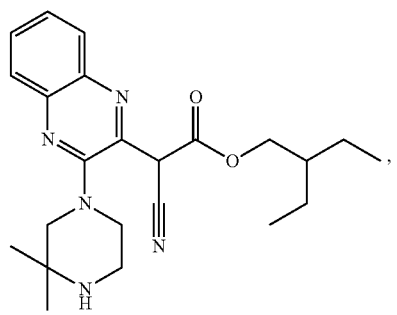
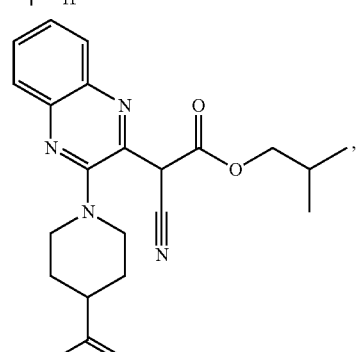
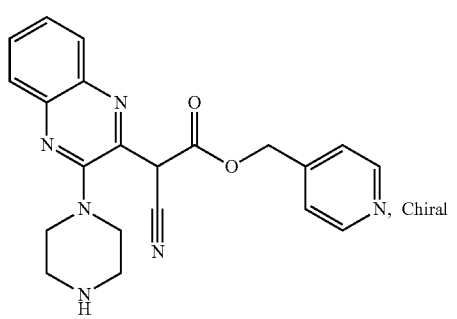

-continued
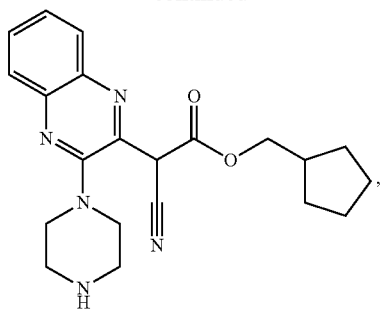
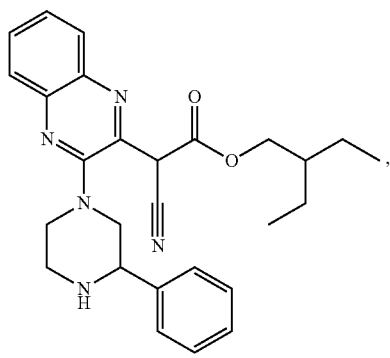
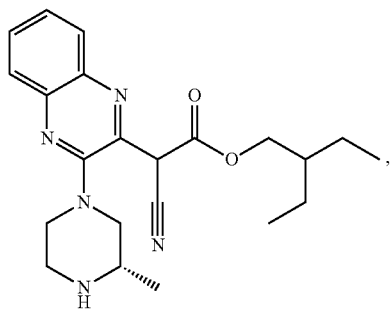
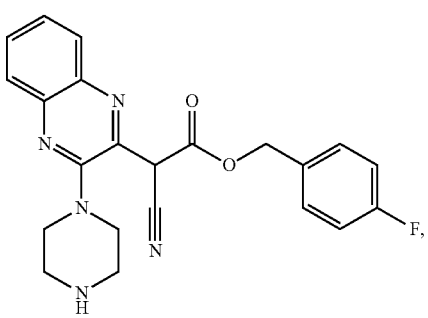
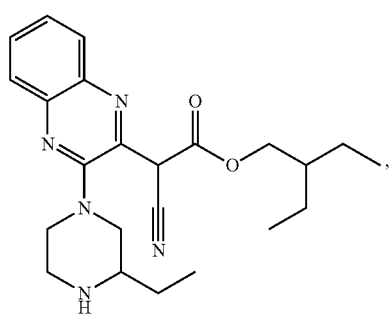
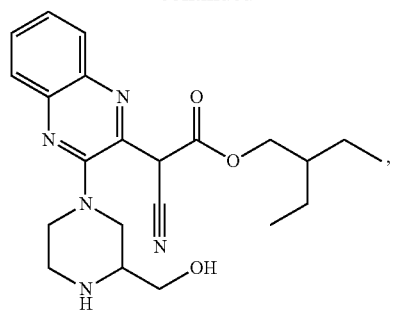
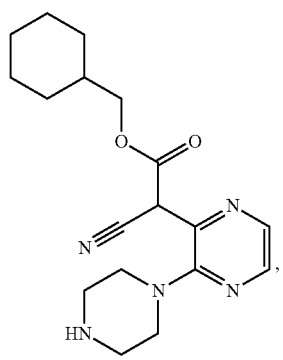
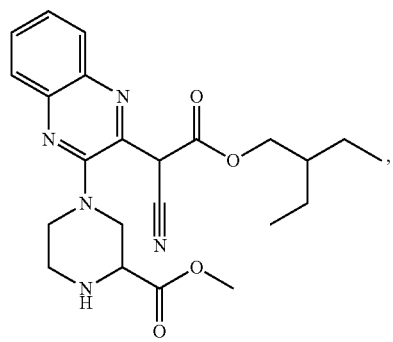
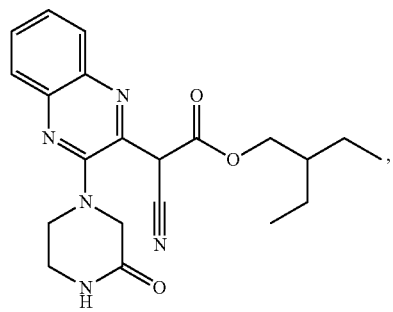
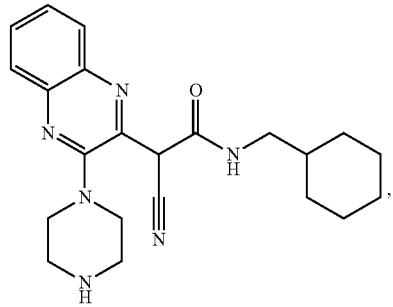

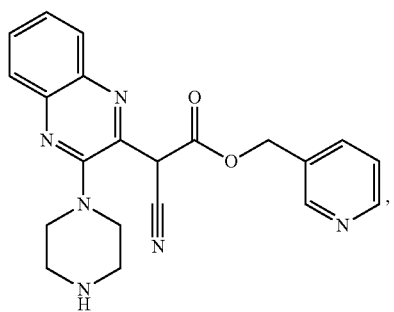
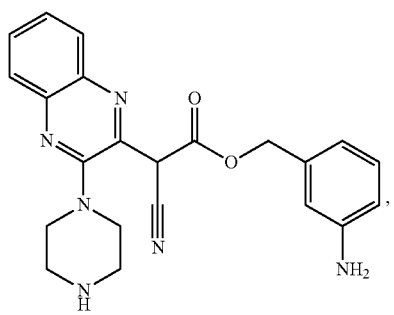
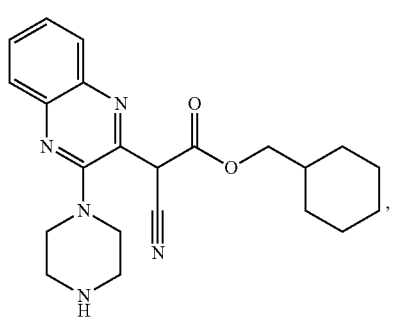
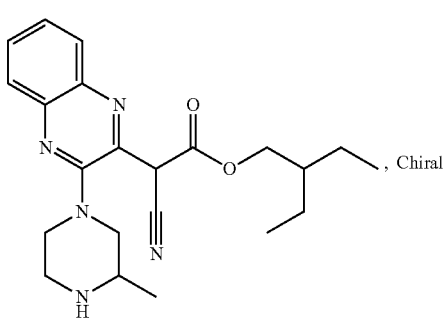
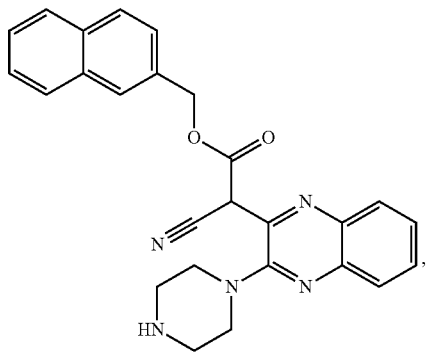
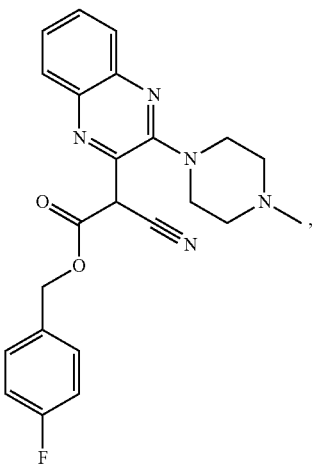
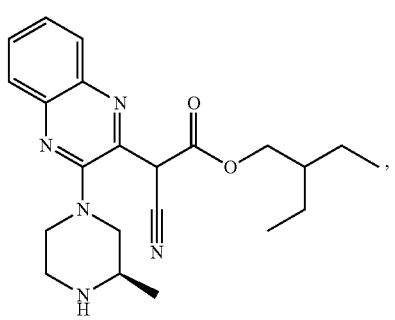
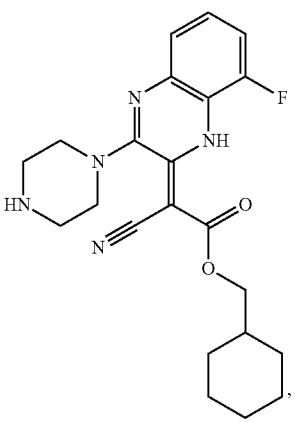
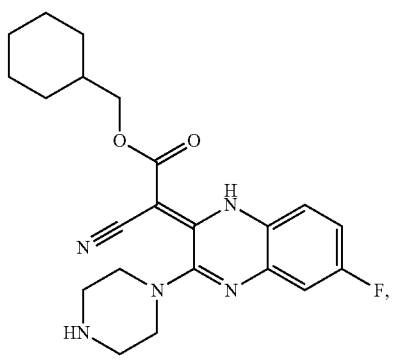

-continued
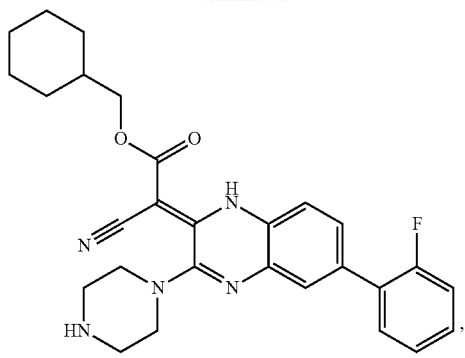
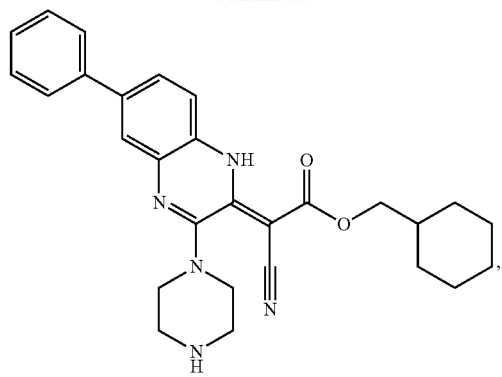
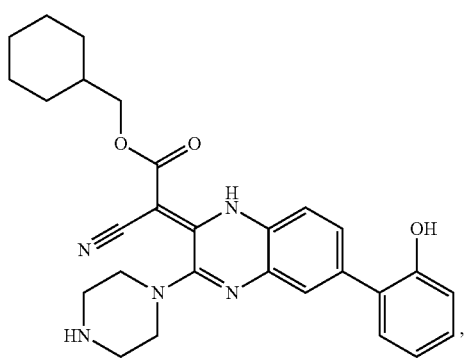
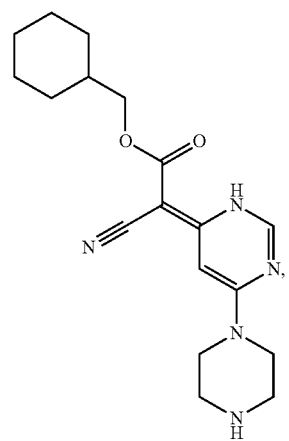
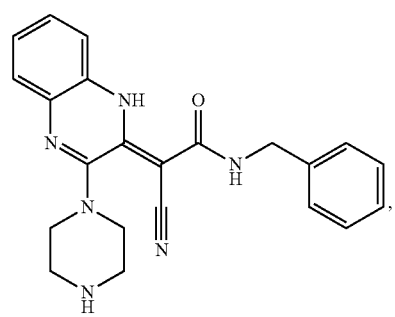
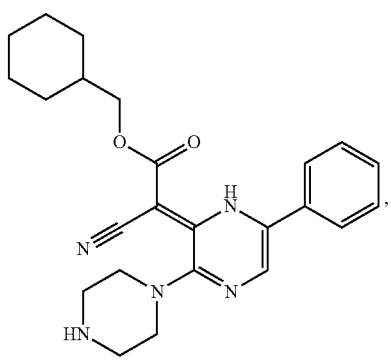
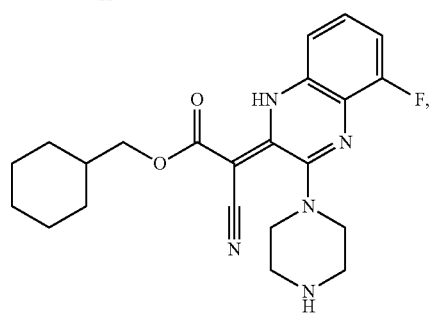
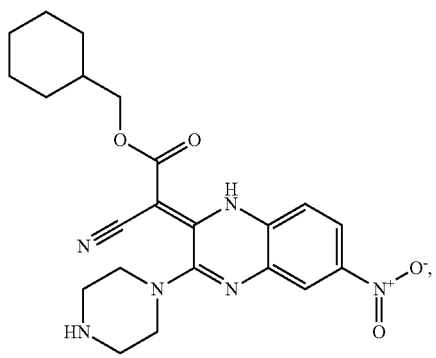
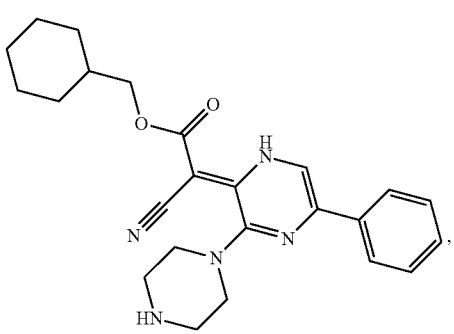

-continued

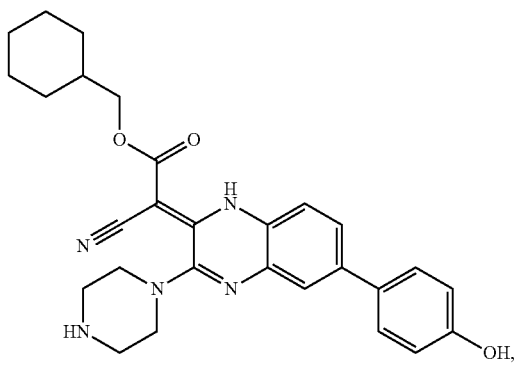

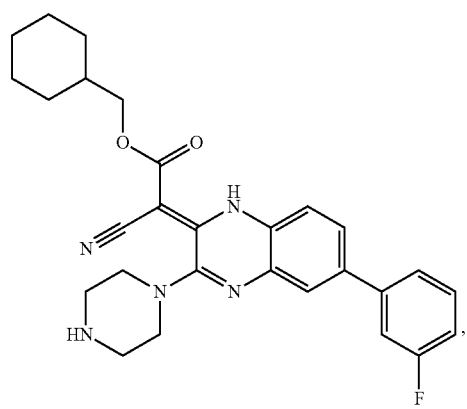

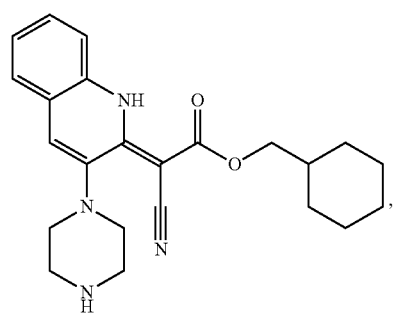

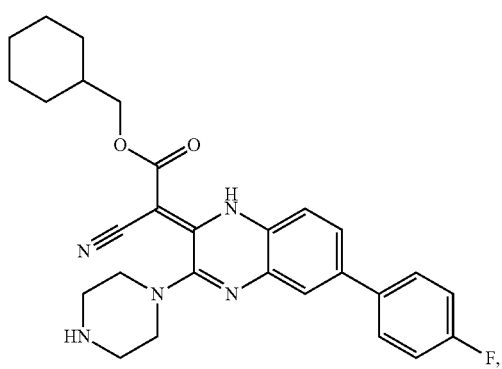

-continued

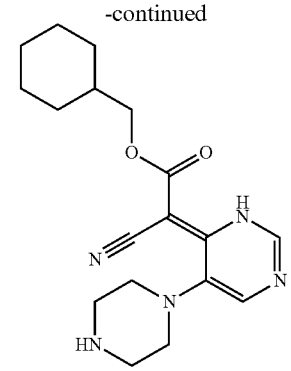

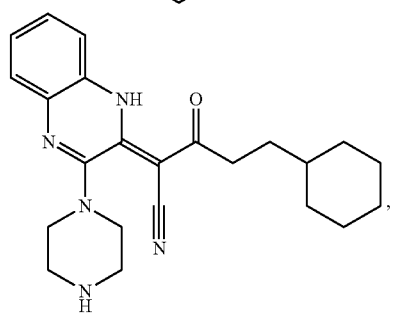

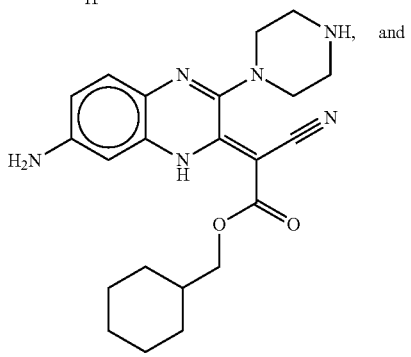

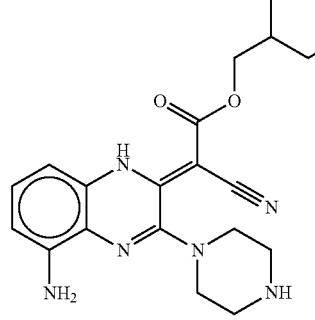

It will be understood that in the event of any inconsistency between a chemical name and formula, both compounds with the indicated chemical name and compounds with the indicated chemical structure will be considered as embraced by the invention.

In certain embodiments, the at least one compound is formulated in a pharmaceutical composition. In other embodiments, the compound is administered to the subject by at least one route selected from oral, rectal, mucosal, transmucosal, topical, and intravenous, intradermal, intramuscular, subcutaneous, intracutaneous, intrauterine, epidural and intracerebroventricular injections.

In various embodiments of any of the above aspects or any other aspects of the invention delineated herein, the hematological cancer is characterized by overexpression, hyperactivation and/or uncontrolled activation of a casein kinase 1, including any of its family members. In certain embodiments, the cancer comprises a hematological cancer, such as acute myeloid leukemia (AML) and/or myelodysplastic syndrome (MDS, including 5q-MDS).

In various embodiments of any of the above aspects or any other aspects of the invention delineated herein, the subject is further administered at least one additional agent useful for treating or preventing a cancer. In certain embodiments, the agent comprises lenalidomide, azacitidine, decitabine, erythropoietin, daunorubicin, idarubicin, cytarabine, mitoxantrone, etoposide, gilteritinib, ATRA (all-trans retinoic acid), or arsenic trioxide. In some embodiments, the agent comprises colorectal chemotherapy. Additional colorectal agents include fluorouracil, capecitabine, irinotecan, oxaliplatin, cetuximab, panitumumab, bevacizumab, trifluridine/tipiracil, and regorafenib. In other embodiments, the compound and the agent are coformulated. In yet other embodiments, the subject is a mammal. In yet other embodiments, the mammal is human. In yet other embodiments, the subject is not responsive to one or more anti cancer agents.

The invention provides compounds with anticancer activity, compositions comprising the same, and methods of treating or preventing certain types of cancer. Compositions and articles defined by the invention were isolated or otherwise synthesized in connection with the non-limiting examples provided below. Other features and advantages of the invention will be apparent from the description and from the claims.

BRIEF DESCRIPTION OF THE DRAWINGS

The following description of embodiments of the invention can be illustrated with the appended drawings. It should be understood, however, that the invention is not limited to the precise arrangements and instrumentalities of the embodiments shown in the drawings.

DETAILED DESCRIPTION OF THE INVENTION

The present invention relates to compounds that can be used to treat certain types of cancer, such as hematological cancers and colon cancer. In certain embodiments, the compounds contemplated within the invention inhibit a casein kinase 1, such as but not limited to casein kinase 1 alpha 1 (CSNK1A1). The present invention further comprises compositions comprising one or more of the compounds contemplated within the invention, and methods of treating or preventing certain types of cancers using the compounds of the invention.

As disclosed herein, CSNK1A1 is an enzyme that plays a role in the development of MDS, AML and colon cancer. For example, administration of CSNK1A1 shRNA to a MLL-AF9 mouse model leads to decreased Rps6 phosphorylation, increased p53 activity, and increased myeloid differentiation. Initial studies of this enzyme target have largely relied on genetic modulation, given a lack of highly selective small molecule inhibitors of the kinase. Unfortunately, the known inhibitors of this kinase suffer from poor drug-like properties. 5-iodotubercidin (5-Iodo-7-β-D-ribofuranosyl-7H-pyrrolo[2,3-d]pyrimidin-4-amine) has poor selectivity, with an $IC_{50}$ of 290 nM against CSNK1A1, but similar inhibitory activity against mitogen-activated protein kinase (ERK2) ($K_i$=525 nM), adenosine kinase (ADK) ($K_i$=30 nM), protein kinase A (PKA) and insulin receptor kinase ($IC_{50}$ ranging from 0.4-28 μM). D4476 (4-[4-(2,3-Dihydro-1,4-benzodioxin-6-yl)-5-(2-pyridinyl)-1H-imidazol-2-yl]benzamide) has an $IC_{50}$ of 320 nM against CSNK1A1, but poor cellular activity. PF4800567 (3-(3-chloro-phenoxymethyl)-1-(tetrahydro-pyran-4-yl)-1H-pyrazolo[3,4-d]pyrimidin-4-ylamine) has an $IC_{50}$ of 860 nM against CSNK1A1, but poor potency.

Figure 1:
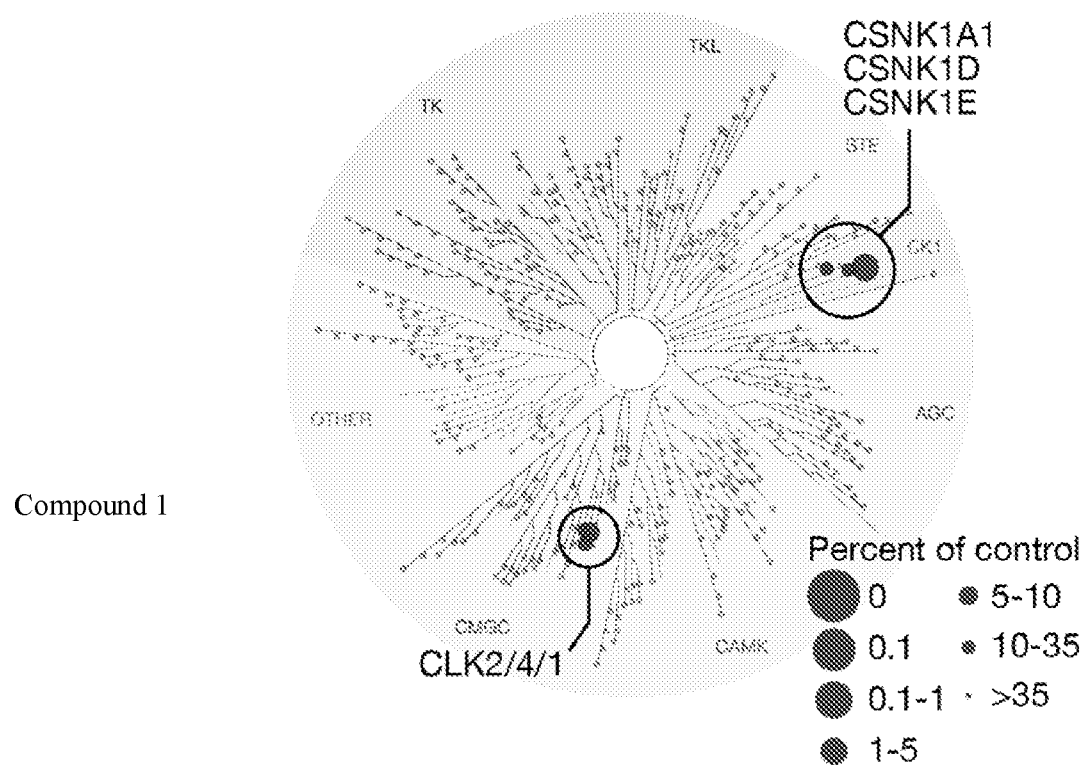
FIG. 1 illustrates exemplary results of kinome-wide profiling of compound 1 using the Kinomescan assay.

As disclosed herein, a gene expression-based approach was used to identify highly specific CSNK1A1 inhibitors: the Connectivity Map described below was examined for small molecules which biological activity resembled CSNK1A1 shRNA knockdown, thus correlating the cellular gene expression signature of CSNK1A1 knockdown with that of treatment with various small molecule compounds. Compound 1 was identified in this study, and its kinome-wide profiling using the Kinomescan assay revealed remarkable specificity for compound binding to CSNK1A1 out of the 450 kinases tested at a single dose of 10 μM (FIG. 1). CSNK1A1 confirmatory thermodynamic $K_d$ was 1,700 nM by Kinomescan and enzymatic $IC_{50}$ was 10.1 μM by Carna Biosciences mobility shift assay.

Unless defined otherwise, all technical and scientific terms used herein generally have the same meaning as commonly understood by one of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "administration" means providing the composition of the present invention to a subject by any suitable method.

As used herein, the term "alkyl" by itself or as part of another substituent means, unless otherwise stated, a straight or branched chain hydrocarbon having the number of carbon atoms designated (i.e., $C_1$-$C_{10}$ means one to ten carbon atoms). By way of illustration, but without limitation, the term "$C_1$-$C_8$ alkyl" refers to a straight chain or branched hydrocarbon moiety having from 1, 2, 3, 4, 5, 6, 7, or 8 carbon atoms. "$C_1$-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, iso-propyl, n-butyl, iso-butyl, sec-butyl, and tert-butyl. The term "$C_1$-$C_4$ n-alkyl" refers to straight chain hydrocarbon moieties that have 1, 2, 3, or 4 carbon atoms including methyl, ethyl, n-propyl, and n-butyl.

As used herein, the term "alkenyl" employed alone or in combination with other terms means, unless otherwise stated, a stable containing at least one double bond, and having from two to ten carbon atoms (i.e., $C_{2-10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to six carbon atoms (e.g., $C_{2-6}$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 2-methylprop-2-enyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), 2,3-dimethyl-2-butenyl ($C_6$) and the like. Additional examples of alkenyl include heptenyl ($C_7$), octenyl ($C_8$), octatrienyl ($C_8$) and the like. Further examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—$CH$=$CH_2$.

As used herein, the term "alkynyl" employed alone or in combination with other terms means, unless otherwise stated, a stable straight chain or branched chain hydrocarbon group with containing at least one triple bond, having from two to ten carbon atoms (i.e., $C_{2-10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In certain embodiments, an alkynyl comprises two to eight carbon atoms. In other embodiments, an alkynyl has two to six carbon atoms (e.g., $C_{2-6}$ alkynyl). The alkynyl is attached to the parent molecular structure by a single bond, for example, ethynyl, propynyl, butynyl, pentynyl, 3-methyl-4-pentenyl, hexynyl, and the like. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —$CR_2CR_2$—C≡CR, wherein each occurrence of R is independently H, alkyl, substituted alkyl, alkenyl or substituted alkenyl, with the proviso that at least one R group is not hydrogen.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, such as, but not limited to, ethoxy and methoxy.

The term "alkoxycarbonyl" refers to a group of the formula (alkoxy)(C=O)— attached to the parent molecular structure through the carbonyl carbon having from 1 to 10 carbon atoms. Thus a $C_{1-6}$ alkoxycarbonyl group is an alkoxy group having from 1 to 6 carbon atoms attached through its oxygen to a carbonyl linker. The $C_{1-6}$ designation does not include the carbonyl carbon in the atom count. "Lower alkoxycarbonyl" refers to an alkoxycarbonyl group wherein the alkyl portion of the alkoxy group is a lower alkyl group (e.g., $C_{1-4}$ alkoxy). In some embodiments, $C_{1-4}$ alkoxy is an alkoxy group which encompasses both straight and branched chain alkoxy groups of from 1 to 4 carbon atoms.

The term "amino" refers to —$NH_2$. "Monoalkylamino" refers to an —NH(alkyl) group, "Dialkylamino" refers to an —N(alkyl)(alkyl) group where each alkyl moiety may be the same or different.

The term "aminocarbonyl", "acylamino", "amide" or "amido" refers to a chemical moiety with formula —C(O)N($R^b$)$_2$, —C(O)N($R^b$)—, —$NR_bC(O)$— or —$NR_bC(O)R_b$, where $R_b$ is independently selected from hydrogen, alkyl, alkenyl, alkynyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl" or "arene" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. In a multi-ring group, only one ring is required to be aromatic, so groups such as indanyl are encompassed by the aryl definition. The ring or ring system can have 6 to 14 ring atoms (e.g., $C_{6-14}$ aromatic or $C_{6-14}$ aryl). Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. Non-limiting examples of aryl groups include phenyl, phenalenyl, naphthalenyl, tetrahydronaphthyl, phenanthrenyl, anthracenyl, fluorenyl, indolyl, indanyl, and the like.

As used herein, the term "aryl-($C_1$-$C_3$)alkyl" means a functional group wherein a one to three carbon alkylene chain is attached to an aryl group, e.g., —$CH_2CH_2$-phenyl or —$CH_2$-phenyl, —CH($CH_3$)-phenyl, —C($CH_3$)($CH_3$)-phenyl. In some embodiments, the group is aryl-$CH_2$— or aryl-CH($CH_3$)—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —CH$_2$CH$_2$-pyridyl. The term "substituted heteroaryl-(C$_1$-C$_3$)alkyl" means a heteroaryl-(C$_1$-C$_3$)alkyl functional group in which the heteroaryl group is substituted.

The term "C$_3$-C$_6$ cycloalkyl" or "C$_3$-C$_6$ cycloalkyl ring" refers to cyclopropyl, cyclobutyl, cyclopentyl, and cyclohexyl. The term "C$_3$-C$_7$ cycloalkyl" or "C$_3$-C$_7$ cycloalkyl ring" also includes cycloheptyl. The term "C$_3$-C$_8$ cycloalkyl" or "C$_3$-C$_8$ cycloalkyl ring" also includes cyclooctyl. The terms "cycloalkyl" and "carbocyclyl" are interchangeable. Cycloalkylalkyl refers to cycloalkyl moieties linked through an alkyl linker chain, as for example, but without limitation, cyclopropylmethyl, cyclopropylethyl, cyclopropylpropyl, cyclopropylbutyl, cyclobutylmethyl, cyclobutylethyl, cyclobutylpropyl, cyclopentylmethyl, cyclopentylethyl, cyclopentylpropyl, cyclohexylmethyl, cyclohexylethyl, and cyclohexylpropyl. The term "cycloalkyl" also includes bridged and spiro-fused cyclic structures containing no heteroatoms.

The term "heteroaryl" or "heteroaromatic ring" as used herein includes 5-, 6- and 7-membered monocyclic or polycyclic (e.g., bicyclic or tricyclic) aromatic ring system having ring carbon atoms and 1, 2, 3, or 4 ring heteroatoms provided in the aromatic ring system, wherein each heteroatom is independently selected from nitrogen, oxygen, phosphorous and sulfur. For example, a heteroaryl can have one or two 5- or 6-membered ring and 1 to 4 heteroatoms selected from N, O, and S. Heteroaryl polycyclic ring systems can include one or more heteroatoms in one or both rings. Exemplary heteroaryls include, but are not limited to, pyrrole, furan, thiophene, imidazole, oxazole, oxadiazole, thiazole, triazole, pyrazole, pyridine, pyrazine, pyridazine, azepine, oxepine, oxazine, triazine, pyrimidine, indole, and benzoimidazole, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like.

As used herein, the term "heteroalkyl" by itself or in combination with another term means, unless otherwise stated, a stable straight or branched chain alkyl group consisting of the stated number of carbon atoms and which have one or more skeletal chain atoms selected from an atom other than carbon, e.g., oxygen, nitrogen, sulfur, phosphorus or combinations thereof. In some embodiments, the heteroalkyl group can have one or two heteroatoms selected from the group consisting of O, N, and S. The nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d] pyridazinyl, 5,6,7,8,9,10 hexahydrocycloocta[d]pyrimidinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimdinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pyridinyl, and thiophenyl (i.e., thienyl).

The term "heterocyclic ring" or "heterocycle" is taken to mean a saturated, unsaturated, or partially unsaturated ring containing from 1, 2, 3, or 4 heteroatoms selected from nitrogen, oxygen and sulfur, said ring optionally being benzofused. A heterocyclic ring can be multicyclic e.g., bicyclic or tricyclic. Polycyclic ring systems can be a fused, bridged or spiro ring system. A heterocycle may have from 3 to 8 ring atoms. The term "3- to 8-membered heterocyclic ring" refers to a ring having from 3, 4, 5, 6, 7 or 8 atoms. The term "3- to 6-membered heterocyclic ring" refers to a ring having from 3, 4, 5, or 6 atoms. The term "5- to 6-membered heterocyclic ring" refers to a ring having 5 or 6 atoms. In some aspects, a heterocyclyl can have one or two 5- or 6-membered rings and 1 to 4 heteroatoms selected from N, O, and S. Exemplary mono-heterocyclic rings, for the purposes of the present invention, include furanyl, thiophenyl (thienyl or thiophenyl), pyrrolyl, pyrrolidinyl, pyridinyl, N-methylpyrrolyl, oxazolyl, isoxazolyl, pyrazolyl, imidazolyl, triazolyl, oxadiazolyl, thiadiazolyl, thiazolyl, thiazolidinyl, N-acetylthiazolidinyl, pyrimidinyl, pyrazinyl, pyridazinyl, and the like. "Heterocyclyl" also includes ring systems wherein the heterocycyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. Heterocyclic rings include bicyclic rings for example, 3-azabicyclo[3.1.0] hexane, 8-oxa-3-azabicyclo[3.2.1]octane. Benzofused heterocyclic rings include isoquinolinyl, benzoxazolyl, benzodioxolyl, benzothiazolyl, quinolinyl, benzofuranyl, benzothiophenyl, indolyl, and the like, all of which may be optionally substituted, which also of course includes optionally substituted on the benzo ring when the heterocycle is benzofused.

As may be specified herein, "heterocyclic ring" or "heterocycle" refers to saturated ring containing from 1, 2, 3, or 4 heteroatoms selected from nitrogen, oxygen and sulfur, and can be multi cyclic e.g., bicyclic or tricyclic. Exemplary heterocyclic rings, for the purposes of the present invention, include azetidinyl, pyrrolidinyl, pyrrolidinonyl, imidazolidinyl, pyrazolidinyl, oxazolidinyl, isoxazolidinyl, triazolidinyl, tetrahyrofuranyl, piperidinyl, piperazinyl, morpholinyl, oxetanyl, and oxathianyl-dioxide.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2, 5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e] [1,4]diazepinyl, 1,4,5,7-tetrahydropyrano[3,4-b]pyrrolyl, 5,6-dihydro-4H-furo[3,2-b]pyrrolyl, 6,7-dihydro-5H-furo [3,2-b]pyranyl, 5,7-dihydro-4H-thieno [2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro [3,2-c]pyridinyl, 4,5,6,7-tetrahydrothieno[3,2-b]pyridinyl, 1,2,3,4-tetrahydro-1,6-naphthyridinyl, and the like.

The term "carboxy" refers to —COOH.

The term "DMSO" refers to dimethylsulfoxide.

The term "halogen" refers to fluoro, chloro, bromo, or iodo.

The term "hydroxyl" or "hydroxy" means —OH.

As used herein, the term "substituted" means that an atom or group of atoms has replaced hydrogen as the substituent attached to another group. Unless stated otherwise, any group recited within the invention may be substituted.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halo, amino, acetamido and nitro. In other embodiments, the substituents are selected from $C_1$-$C_6$ alkyl, $C_2$-$C_6$ alkenyl, $C_2$-$C_6$ alkynyl, aryl, heterocyclyl, heteroaryl, halo, haloalkyl (including trifluoromethyl), —SR, —S(=O)($C_1$-$C_6$ alkyl), —S(=O)$_2$($C_1$-$C_6$ alkyl), —S(=O)$_2$ NRR, —OR, —C(=O)R, —O—C(=O)R, —C(=O)OR, —OC(=O)O($C_1$-$C_6$ alkyl), —NRR, —C(=O)NRR, —N(R)C(=O)R, —C(=NR)NRR, —P(=O)(OR)$_2$, cyano and nitro; wherein each R is independently selected from the group consisting of H, alkyl, heteroalkyl, cycloalkyl, aryl, heterocyclyl, and heteroaryl. As used herein, where a substituent is an alkyl or alkoxy group, the carbon chain may be branched or straight.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable.

For alkyl and cycloalkyl groups, the term "substituted" refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In some embodiments, the substituents are selected from $C_1$-$C_6$ alkyl, halo, hydroxy, alkoxy, amino, monoalkylamino, dialkylamino, aminocarbonyl, acylamino, carboxy, alkoxycarbonyl, sulfanyl, sulfinyl, sulfonyl and sulfonamide.

The terms "sulfanyl", "sulfide", and "thio" each refer to the radical —S—$R^b$, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. For instance, an "alkylthio" refers to the "alkyl-S—" radical, and "arylthio" refers to the "aryl-S—" radical, each of which are bound to the parent molecular group through the S atom. The terms "sulfide", "thiol", "mercapto", and "mercaptan" can also each refer to the group —$R^b$SH.

The term "sulfinyl" or "sulfoxide" refers to the —S(O)—$R^b$ radical, wherein for"sulfinyl", $R^b$ is H and for"sulfoxide", $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

The term "sulfonyl" or "sulfone" refers to the —S($O_2$)—$R^b$ radical, wherein $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

The term "sulfonamidyl" or "sulfonamido" refers to the following radicals: —S(=O)$_2$—($R^b$)$_2$, —N($R^b$)—S(=O)$_2$—$R^b$, —S(=O)$_2$—N($R^b$)—, or —N($R^b$)—S(=O)$_2$—, where each $R_b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. The $R^b$ groups in —S(=O)$_2$—($R^b$)$_2$ can be taken together with the nitrogen to which they are attached to form a 4-, 5-, 6-, or 7-membered heterocyclyl ring. In some embodiments, the term designates a $C_{1-4}$ sulfonamido, wherein each $R^b$ in the sulfonamido contains 1 carbon, 2 carbons, 3 carbons, or 4 carbons total.

In some aspects, the compound is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ⚊ which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

The term "enantiomers" refers to a pair of stereoisomers that are non-superimposable mirror images of each other. An atom having an asymmetric set of substituents can give rise to an enantiomer. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures.

Optically active (R)- and (S)-isomers can be prepared, for example, using chiral synthons or chiral reagents, or resolved using conventional techniques. Enantiomers can be isolated from racemic mixtures by any method known to those skilled in the art, including chiral high pressure liquid chromatography (HPLC), the formation and crystallization of chiral salts, or prepared by asymmetric syntheses.

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the compound of the invention can be a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Additionally, some compounds may undergo the tautomerization

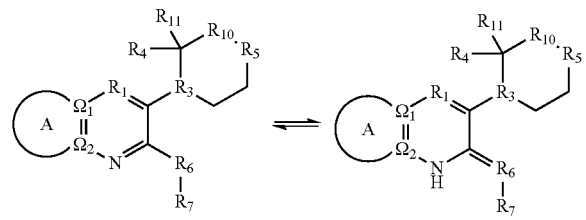

All chiral, diastereomeric, racemic, and geometric isomeric forms of a structure are intended, unless specific stereochemistry or isomeric form is specifically indicated. All processes used to prepare compounds of the present invention and intermediates made therein are considered to be part of the present invention. All tautomers of shown or described compounds are also considered to be part of the present invention.

As used herein, the term "ALL" refers to acute lymphoblastic leukemia.

As used herein, the term "AML" refers to acute myeloid leukemia.

In one aspect, the terms "co-administered" and "co-administration" as relating to a subject refer to administering to the subject a composition of the invention, or salt thereof, along with a composition that may also treat any of the diseases contemplated within the invention. In one embodiment, the co-administered compositions are administered separately, or in any kind of combination as part of a single therapeutic approach. The co-administered composition may be formulated in any kind of combinations as mixtures of solids and liquids under a variety of solid, gel, and liquid formulations, and as a solution.

As used herein, the term "CLL" refers to chronic lymphocytic leukemia.

As used herein, the term "CML" refers to chronic myeloid leukemia.

As used herein, the term "composition" or "pharmaceutical composition" refers to a mixture of at least one compound useful within the invention with a pharmaceutically acceptable carrier. The pharmaceutical composition facilitates administration of the compound to a subject.

As used herein, the term "compound 1" refers to cyclohexyl 2-cyano-2-(3-(4-ethyl piperazin-1-yl)quinoxalin-2-yl) acetate, or a salt or N-oxide thereof.

As used herein, the term "compound 2" refers to benzyl 2-cyano-2-(3-(4-methyl piperazin-1-yl)quinoxalin-2-yl)acetate, or a salt or N-oxide thereof.

As used herein, the term "compound 3" refers to 2-ethylbutyl 2-cyano-2-(3-(4-ethyl piperazin-1-yl)quinoxalin-2-yl)acetate, or a salt or N-oxide thereof.

As used herein, the term "compound 4" refers to cyclohexyl 2-cyano-2-(3-(4-methyl piperazin-1-yl)quinoxalin-2-yl)acetate, or a salt or N-oxide thereof.

As used herein, the term "compound 5" refers to isopropyl 2-cyano-2-(3-(4-methyl piperazin-1-yl)quinoxalin-2-yl)acetate, or a salt or N-oxide thereof.

As used herein, the term "δ" refers to delta (ppm).

By "disease" or "disorder" is meant any condition that damages or interferes with the normal function of a cell, tissue, or organ. In certain embodiments, the disease comprises a cancer in a subject.

As used herein, an "effective amount" of a therapeutic agent, e.g. a compound of the invention, refers to an amount effective, at dosages and for periods of time necessary, to achieve the desired therapeutic, biologic or prophylactic effect. For example, an effective amount of a compound of the invention is that amount sufficient to treat a disease, disorder, or condition. In another aspect, an effective amount of a compound is that amount sufficient to prevent a disease, disorder, or condition. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial toxicity and yet is entirely effective to treat the subject. The effective amount for any particular application can vary depending on such factors as the condition being treated, the particular compounds being administered the size of the subject, or the severity of the condition.

As used herein, the term "instructional material" includes a publication, a recording, a diagram, or any other medium of expression that may be used to communicate the usefulness of the compositions and methods of the invention. In some instances, the instructional material may be part of a kit useful for treating a hematological cancer in a subject. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

As used herein, the term "MDS" refers to myelodysplastic syndrome.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, "pharmaceutically acceptable carrier" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self-emulsifying drug delivery systems (SEDDS) such as d-a-tocopherol poly ethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as $\alpha$-, $\beta$-, and $\gamma$-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

By "pharmaceutical formulation" it is further meant that the carrier, solvent, excipient(s) and/or salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

As used herein, the term "salt" refers to a salt of a compound contemplated within the invention, including inorganic acids, organic acids, inorganic bases, organic bases, solvates, hydrates, or clathrates thereof. As used herein, the term "salt" embraces addition salts of free acids or free bases that are compounds useful within the invention. The term "acid addition salt" refers to a salt of a compound of the invention prepared by reaction of a compound of the invention with a mineral or organic acid. For exemplification of pharmaceutically acceptable acid addition salts, see, e.g., Berge, S. M., Bighley, L. D., and Monkhouse, D. C., *J. Pharm. Sci.*, 66:1, 1977. For example, compounds of this invention which are an amine compound are basic in nature and accordingly react with any of a number of inorganic and organic acids to form pharmaceutically acceptable acid addition salts.

Pharmaceutically acceptable acid addition salts of the invention can be formed by the reaction of a compound of the invention with an equimolar or excess amount of acid. Alternatively, hemi-salts can be formed by the reaction of a compound of the invention with the desired acid in a 2:1 ratio, compound to acid. The reactants are generally combined in a mutual solvent such as diethyl ether, tetrahydrofuran, methanol, ethanol, iso-propanol, benzene, or the like. The salts normally precipitate out of solution within, e.g., about one hour to about ten days and can be isolated by filtration or other conventional methods.

Inorganic acids commonly employed to form such salts include hydrochloric acid, hydrobromic acid, hydroiodic acid, sulfuric acid, phosphoric acid, and the like. Organic acids commonly employed to form such salts include p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, iso-butyrate, caproate, heptanoate, propiolate, oxalate, malonate, succinate, hemisuccinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, $\beta$-hydroxybutyrate, glycolate, tartrate, methanesulfonate, propanesulfonate, naphthalene-1-sulfonate, naphthalene-2-sulfonate, mandalate and the like. "Prodrugs" are intended to include any covalently bonded carriers that release an active parent drug (compound) of the present invention in vivo when such prodrug is administered to a subject. Prodrugs are prepared, for example, by modifying functional groups present in the compound in such a way that the modifications are cleaved, either in routine manipulation or in vivo, to the parent compound. Prodrugs include compounds of the invention wherein a hydroxyl or amino group is bonded to any group that, when the prodrug of the present invention is administered to a subject, it cleaves to form a free hydroxyl or free amino group, respectively. Examples of prodrugs include, but are not limited to, acetate, formate, and benzoate derivatives of alcohol and amine functional groups in the compounds of the present invention. Examples of prodrugs include, but are not limited to, benzamide derivatives of an amine functional group in the active compound and the like. Other examples of prodrugs include compounds that comprise —NO, —NO$_2$, —ONO, or —ONO$_2$ moieties.

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as ($C_{1-8}$)alkyl, ($C_{1-12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 10 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as [3-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino ($C_{2-3}$)alkyl.

Similarly, if a disclosed compound or a pharmaceutically acceptable form of the compound contains an alcohol functional group, a prodrug can be formed by the replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, α-amino($C_{1-4}$)alkanoyl, arylacyl, and α-aminoacyl, or α-aminoacyl-α-aminoacyl, where each α-aminoacyl group is independently selected from the naturally occurring L-amino acids, —P(O)(OH)$_2$, —P(O)(O($C_{1-6}$)alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_{1-10}$)alkyl, ($C_{3-7}$)cycloalkyl, benzyl, a natural α-aminoacyl or natural α-aminoacyl-natural-α-aminoacyl, —C(OH)C(O)OY$^1$ wherein Y$^1$ is H, ($C_{1-6}$) alkyl or benzyl, C(OY$^2$)Y$^3$ wherein Y$^2$ is ($C_{1-4}$)alkyl and Y$^3$ is ($C_{1-6}$)alkyl, carboxy($C_{1-6}$)alkyl, amino($C_{1-4}$)alkyl or mono-N— or di-N,N—($C_{1-6}$)alkylaminoalkyl, —C(Y$^4$)Y$^5$ wherein Y$^4$ is H or methyl and Y$^5$ is mono-N— or di-N,—($C_{1-6}$)alkylamino, morpholino, piperidin-1-yl or pyrrolidin-1-yl.

In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The term "prevent" or "preventing" or "prevention," as used herein, means avoiding or delaying the onset of symptoms associated with a disease or condition in a subject that has not developed such symptoms at the time the administering of an agent or compound commences. Disease, condition, and disorder are used interchangeably herein.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

The term "solvate" means a solvent addition form that contains either a stoichiometric or non-stoichiometric amount of solvent. Some compounds have a tendency to trap a fixed molar ratio of solvent molecules in a solid state, thus forming a solvate. If the solvent is water, the solvate formed is a hydrate; when the solvent is alcohol, the solvate formed is an alcoholate. Hydrates are formed by the combination of one or more molecules of water with one of the substances in which the water retains its molecular state as H$_2$O, such combination being able to form one or more hydrates.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the term "treat," "treatment" or "treating" herein, is meant decreasing the symptoms, markers, and/or any negative effects of a disease, disorder, and/or condition in any appreciable degree in a patient who currently has the a disease, disorder, and/or condition. Treatment can include a decrease in the severity of symptoms in acute or chronic disease as well as a decrease in the relapse or exacerbation rate in relapsing-remitting disease. In one aspect, treating a disease means reversing or stopping the disease's progression. Ameliorating a disease and alleviating a disease are equivalent to treating a disease.

As used herein, the term "prevent," "prevention," or "preventing" refers to any method to partially or completely prevent or delay the onset of one or more symptoms or features of a disease, disorder, and/or condition. Prevention is causing the clinical symptoms of the disease state not to develop, i.e., inhibiting the onset of disease, in a subject that may be exposed to or predisposed to the disease state, but does not yet experience or display symptoms of the disease state. Prevention may be administered to a subject who does not exhibit signs of a disease, disorder, and/or condition.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

In one aspect, the invention provides anticancer compounds. In certain embodiments, the compounds inhibit at least one casein kinase 1 family member. In other embodiments, the compounds inhibit at least one selected from the group consisting of casein kinase 1 alpha 1 (CSNK1A1), casein kinase 1 delta (CSNK1D), and casein kinase 1 epsilon (CSNK1E). In yet other embodiments, the compounds inhibit casein kinase 1 alpha 1 (CSNK1A1). In yet other embodiments, the compounds inhibit casein kinase 1 delta (CSNK1D). In yet other embodiments, the compounds inhibit casein kinase 1 epsilon (CSNK1E).

The compounds may have the structure of formula (I) and subgenera thereof (e.g., (Ia), (Ib), (Ic), (Id), (Ie), (If), (Ig), (Ih), (Ii), (Ij), (Ik), (Il), (Im), (In), etc.):

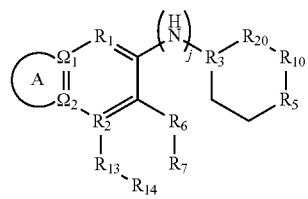

(I)

wherein:

"j" is 0 or 1;

$R_1$ is selected from the group consisting of N, C—H, C—F and C—OH, where at least one of $R_1$ and $R_2$ is N;

$R_2$ is selected from the group consisting of N (i.e. $R_{13}$ is absent), C—H (i.e. $R_{13}$ is absent), C—F (i.e. $R_{13}$ is absent), C—OH (i.e. $R_{13}$ is absent), and C, $R_3$ is selected from the group consisting of N, CH, CF and COH;

$R_5$ is selected from the group consisting of N(H), N($C_1$-$C_6$ alkyl), C(H)—NH$_2$, C(H)—NH($C_1$-$C_6$ alkyl), C(H)—($C_1$-$C_6$ alkyl)-NH$_2$, C(H)—C(=O)—NH$_2$, and C(H)—N($C_1$-$C_6$ alkyl)($C_1$-$C_6$ alkyl);

one of $R_6$ or $R_7$ is absent (i.e., it is a bond) and the other of $R_6$ or $R_{13}$ is selected from the group consisting of —C(H)(CN)—, —C(H)(C≡CH)—, —CH$_2$—, —C(H)(CH$_3$)—, —C(CH$_3$)(CN)—, —N(CN)—, and —NH—; where $R_7$ is hydrogen when $R_6$ is absent, and where $R_{14}$ is hydrogen when $R_{13}$ is absent;

$R_7$ and $R_{14}$ are independently selected from the group consisting of —C(=O)OR$_8$, —C(=O)N(R$_9$)R$_8$, —C(=O)N(H)R$_8$, —NHC(=O)R$_8$, —C(=O)C(R$_9$)=C(R$_9$)(R$_9$), N$^1$—R$_8$-1H-imidazol-2-yl, —CH$_2$OR$_8$, and 2-R$_8$-1,3,5-oxadiazol-5-yl;

$R_{10}$ and $R_{20}$ are selected from the group consisting of C(H)(R$_{12}$), C(R$_{12}$)(R$_{12}$), and C(=O);

each occurrence of $R_8$ is independently selected from the group consisting of H, $C_1$-$C_6$ alkyl, aryl, $C_3$-$C_8$ cycloalkyl, $C_3$-$C_8$ cycloalkyl-($C_1$-$C_3$)alkyl, $C_3$-$C_8$ heterocycloalkyl-($C_1$-$C_3$)alkyl, aryl-($C_1$-$C_3$)alkyl, ($C_1$-$C_6$) hydroxyalkyl, imidazol-2-yl optionally substituted with methyl, and oxadiazol-5-yl optionally substituted with methyl or benzyl;

each occurrence of $R_9$ is independently selected from the group consisting of H, $C_1$-$C_6$ alkyl, aryl, and halogen;

each occurrence of $R_{12}$ is independently selected from the group consisting of H, $C_1$-$C_6$ alkyl, aryl, ($C_1$-$C_6$) hydroxyalkyl, $C_3$-$C_8$ cycloalkyl-($C_1$-$C_3$)alkyl, —C(=O)O—($C_1$-$C_6$) alkyl;

moiety "A" is selected from the group consisting of:

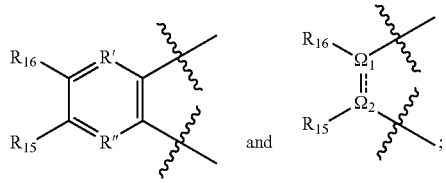

wherein R' and R" are independently selected from the group consisting of N, C—H, C—F, and C—R$_{17}$;

$\Omega_1$ and $\Omega_2$ are independently selected at each occurrence from C, CH, and N and the dashed ("-----") bond is a double bond or single bond;

$R_{15}$, $R_{16}$, and $R_{17}$ are independently selected at each occurrence from hydrogen, aryl, halo, amino, and nitro; and each alkyl, aryl, arylalkyl, heterocycloalkylalkyl, cycloalkylalkyl, and/or cycloalkyl group is independently optionally substituted with at least one selected from the group consisting of $C_1$-$C_6$ alkyl, halo, hydroxy, alkoxy, amino, monoalkylamino, dialkylamino, aminocarbonyl, acylamino, carboxy, alkoxycarbonyl, sulfanyl, sulfinyl, sulfonyl, and sulfonamide; and, each aryl and/or aryl($C_1$-$C_3$)alkyl group is independently optionally substituted with at least one selected from the group consisting of $C_1$-$C_6$ alkyl, $C_2$-$C_6$ alkenyl, $C_2$-$C_6$ alkynyl, aryl, heterocyclyl, heteroaryl, halo, haloalkyl (including trifluoromethyl), —SR, —S(=O)($C_1$-$C_6$ alkyl), —S(=O)$_2$($C_1$-$C_6$ alkyl), —S(=O)$_2$NRR, —OH, —OR, —C(=O)R, —O—C(=O)R, —C(=O)OR, —OC(=O)O($C_1$-$C_6$ alkyl), —NRR, —C(=O)NRR, —N(R)C(=O)R, —C(=NR)NRR, —P(=O)(OR)$_2$, cyano and nitro; wherein each R is independently selected from the group consisting of H, alkyl, heteroalkyl, cycloalkyl, aryl, heterocyclyl, and heteroaryl.

In certain embodiments, the invention includes a compound of formula (Ia), or a salt or N-oxide thereof:
a compound of formula (I):

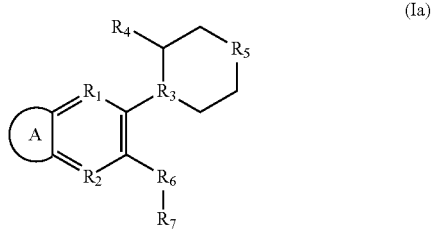

(Ia)

wherein $R_4$ is hydrogen, CH, or CN.

In some embodiments, the compound is cyclohexyl 2-cyano-2-(3-(4-ethylpiperazin-1-yl)quinoxalin-2-yl)acetate (compound 1);

benzyl 2-cyano-2-(3-(4-methylpiperazin-1-yl)quinoxalin-2-yl)acetate (compound 2);
2-ethylbutyl 2-cyano-2-(3-(4-ethylpiperazin-1-yl)quinoxalin-2-yl)acetate (compound 3);
cyclohexyl 2-cyano-2-(3-(4-methylpiperazin-1-yl)quinoxalin-2-yl)acetate (compound 4);
isopropyl 2-cyano-2-(3-(4-methylpiperazin-1-yl)quinoxalin-2-yl)acetate (compound 5);
benzyl 2-(3-(4-methylpiperazin-1-yl)quinoxalin-2-yl)but-3-ynoate;
benzyl 2-(3-(4-methylpiperazin-1-yl)quinoxalin-2-yl)propanoate;
benzyl 2-cyano-2-(3-(4-methylpiperazin-1-yl)quinoxalin-2-yl)propanoate;
N-benzyl-2-cyano-2-(3-(4-methylpiperazin-1-yl)quinoxalin-2-yl)acetamide;
1-phenylethyl 2-cyano-2-(3-(4-methylpiperazin-1-yl)quinoxalin-2-yl)acetate;
2-phenylpropan-2-yl 2-cyano-2-(3-(4-methylpiperazin-1-yl)quinoxalin-2-yl)acetate;
3-hydroxy-2-(3-(4-methylpiperazin-1-yl)quinoxalin-2-yl)propanenitrile;
3-methoxy-2-(3-(4-methylpiperazin-1-yl)quinoxalin-2-yl)propanenitrile;
3-(benzyloxy)-2-(3-(4-methylpiperazin-1-yl)quinoxalin-2-yl)propanenitrile;
N-(cyano(3-(4-methylpiperazin-1-yl)quinoxalin-2-yl)methyl)-2-phenylacetamide;
benzyl N-cyano(3-(4-methylpiperazin-1-yl)quinoxalin-2-yl)carbamate;
pentan-3-yl 2-cyano-2-(3-(piperidin-4-ylamino)quinoxalin-2-yl)acetate;
1-(3-(4-methylpiperazin-1-yl)quinoxalin-2-yl)but-3-en-2-one;
N-(3-(4-methylpiperazin-1-yl)quinoxalin-2-yl)acrylamide;
benzyl 2-(3-(2-cyano-4-methylpiperazin-1-yl)quinoxalin-2-yl)acetate;
benzyl 2-cyano-2-(3-(2,4-dimethylpiperazin-1-yl)quinoxalin-2-yl)acetate;
benzyl 2-cyano-2-(3-(1-methylpiperidin-4-yl)quinoxalin-2-yl)acetate;
benzyl 2-cyano-2-(3-(4-fluoro-1-methylpiperidin-4-yl)quinoxalin-2-yl)acetate;
benzyl 2-cyano-2-(3-(4-hydroxy-1-methylpiperidin-4-yl)quinoxalin-2-yl)acetate;
N-(cyano(3-(4-methylpiperazin-1-yl)quinoxalin-2-yl)methyl)acetamide;
benzyl 2-(3-(4-aminopiperidin-1-yl)quinoxalin-2-yl)-2-cyanoacetate;
benzyl 2-cyano-2-(3-(4-(methylamino)piperidin-1-yl)quinoxalin-2-yl)acetate;
benzyl 2-cyano-2-(3-(4-(dimethylamino)piperidin-1-yl)quinoxalin-2-yl)acetate;
2-(1-benzyl-1H-imidazol-2-yl)-2-(3-(4-methylpiperazin-1-yl)quinoxalin-2-yl)acetonitrile;
2-(1-methyl-1H-imidazol-2-yl)-2-(3-(4-methylpiperazin-1-yl)quinoxalin-2-yl)acetonitrile;
2-(5-benzyl-1,3,4-oxadiazol-2-yl)-2-(3-(4-methylpiperazin-1-yl)quinoxalin-2-yl)acetonitrile;
2-(5-methyl-1,3,4-oxadiazol-2-yl)-2-(3-(4-methylpiperazin-1-yl)quinoxalin-2-yl)acetonitrile;
benzyl 2-cyano-2-(3-(4-methylpiperazin-1-yl)quinolin-2-yl)acetate;
benzyl 2-cyano-2-(2-(4-methylpiperazin-1-yl)quinolin-3-yl)acetate;
benzyl 2-cyano-2-(2-(4-methylpiperazin-1-yl)-1,5-naphthyridin-3-yl)acetate;
benzyl 2-cyano-2-(3-(4-methylpiperazin-1-yl)-1,5-naphthyridin-2-yl)acetate;
benzyl 2-cyano-2-(2-(4-methylpiperazin-1-yl)-4-oxo-1,4-dihydroquinolin-3-yl)acetate;
benzyl 2-cyano-2-(3-(4-methylpiperazin-1-yl)-4-oxo-1,4-dihydroquinolin-2-yl)acetate;
benzyl 2-cyano-2-(5,6-dimethyl-3-(4-methylpiperazin-1-yl)pyrazin-2-yl)acetate;
benzyl 2-cyano-2-(3-(4-methylpiperazin-1-yl)pyrazin-2-yl)acetate;
benzyl 2-cyano-2-(4-fluoro-3-(4-methylpiperazin-1-yl)quinolin-2-yl)acetate;
benzyl 2-cyano-2-(4-fluoro-2-(4-methylpiperazin-1-yl)quinolin-3-yl)acetate;
4-fluorobenzyl 2-cyano-2-(3-(4-methylpiperazin-1-yl)quinoxalin-2-yl)acetate;
2-ethylbutyl 2-cyano-2-(3-(4-methylpiperazin-1-yl)quinoxalin-2-yl)acetate;
2-ethylbutyl 2-cyano-2-(3-(piperazin-1-yl)quinoxalin-2-yl)acetate;
2,2 dimethyl propyl 2-cyano-2-(3-(piperazin-1-yl)quinoxalin-2-yl)acetate;
2,2 dimethyl propyl 2-cyano-2-(3-(methylpiperazin-1-yl)quinoxalin-2-yl)acetate;
2-fluorobenzyl 2-cyano-2-(3-(piperazin-1-yl)quinoxalin-2-yl)acetate;
3-fluorobenzyl 2-cyano-2-(3-(piperazin-1-yl)quinoxalin-2-yl)acetate;
4-fluorobenzyl 2-cyano-2-(3-(piperazin-1-yl)quinoxalin-2-yl)acetate;
3-aminobenzyl 2-cyano-2-(3-(piperazin-1-yl)quinoxalin-2-yl)acetate;
2-ethylbutyl 2-cyano-2-(3-(4-(amino)piperidin-1-yl)quinoxalin-2-yl)acetate;
2-ethylbutyl 2-cyano-2-(3-(4-(aminomethyl)piperidin-1-yl)quinoxalin-2-yl)acetate;
cyclohexyl 2-cyano-2-(3-(4-methylpiperazin-1-yl)quinoxalin-2-yl)acetate;
pentan-3-yl 2-cyano-2-(3-(3-isopropylpiperazin-1-yl)quinoxalin-2-yl)acetate;
cycloheptylmethyl 2-cyano-2-(3-(piperazin-1-yl)quinoxalin-2-yl)acetate;
cyclohexylmethyl 2-cyano-2-(3-(4-methylpiperazin-1-yl)quinoxalin-2-yl)acetate;
cyclohexylmethyl 2-cyano-2-(3-(4-methylpiperazin-1-yl)quinoxalin-2-yl)acetate;
2-ethylbutyl 2-cyano-2-(3-(3,3-dimethylpiperazin-1-yl)quinoxalin-2-yl)acetate;
isobutyl 2-(3-(4-carbamoylpiperidin-1-yl)quinoxalin-2-yl)-2-cyanoacetate;
pyridin-4-ylmethyl 2-cyano-2-(3-(4-methylpiperidin-1-yl)quinoxalin-2-yl)acetate;
cyclopentylmethyl 2-cyano-2-(3-(piperazin-1-yl)quinoxalin-2-yl)acetate;
2-ethylbutyl 2-cyano-2-(3-(3-phenylpiperazin-1-yl)quinoxalin-2-yl)acetate;
2-ethylbutyl 2-cyano-2-(3-((S)-3-methylpiperazin-1-yl)quinoxalin-2-yl)acetate;
4-fluorobenzyl 2-cyano-2-(3-(piperazin-1-yl)quinoxalin-2-yl)acetate;
2-ethylbutyl 2-cyano-2-(3-(3-ethylpiperazin-1-yl)quinoxalin-2-yl)acetate;
2-ethylbutyl 2-cyano-2-(3-(3-(hydroxymethyl)piperazin-1-yl)quinoxalin-2-yl)acetate;
cyclohexylmethyl 2-cyano-2-(3-(3-methylpiperazin-1-yl)quinoxalin-2-yl)acetate;

methyl 4-(3-(1-cyano-2-(2-ethylbutoxy)-2-oxoethyl)quinoxalin-2-yl)piperazine-2-carboxylate;
3-(2-ethylbutoxy)-2-(3-(3-oxopiperazin-1-yl)quinoxalin-2-yl)but-3-enenitrile;
2-ethylbutyl 2-cyano-2-(3-(3-oxopiperazin-1-yl)quinoxalin-2-yl)acetate;
2-cyano-N-(cyclohexylmethyl)-2-(3-(piperazin-1-yl)quinoxalin-2-yl)acetamide;
pyridin-3-ylmethyl 2-cyano-2-(3-(piperazin-1-yl)quinoxalin-2-yl)acetate;
3-aminobenzyl 2-cyano-2-(3-(piperazin-1-yl)quinoxalin-2-yl)acetate;
cyclohexylmethyl 2-cyano-2-(3-(piperazin-1-yl)quinoxalin-2-yl)acetate;
2-ethylbutyl 2-cyano-2-(3-(3-methylpiperazin-1-yl)quinoxalin-2-yl)acetate;
naphthalen-2-ylmethyl 2-cyano-2-(3-(piperazin-1-yl)quinoxalin-2-yl)acetate;
4-fluorobenzyl 2-cyano-2-(3-(4-methylpiperazin-1-yl)quinoxalin-2-yl)acetate;
2-ethylbutyl 2-cyano-2-(3-((R)-3-methylpiperazin-1-yl)quinoxalin-2-yl)acetate;
cyclohexylmethyl 2-cyano-2-(8-fluoro-3-(piperazin-1-yl)quinoxalin-2-yl)acetate;
cyclohexylmethyl 2-cyano-2-(6-fluoro-3-(piperazin-1-yl)quinoxalin-2-yl)acetate;
cyclohexylmethyl 2-cyano-2-(6-(2-fluorophenyl)-3-(piperazin-1-yl)quinoxalin-2-yl)acetate;
cyclohexylmethyl 2-cyano-2-(6-(2-hydroxyphenyl)-3-(piperazin-1-yl)quinoxalin-2-yl)acetate;
N-benzyl-2-cyano-2-(3-(piperazin-1-yl)quinoxalin-2-yl)acetamide;
cyclohexylmethyl 2-cyano-2-(5-fluoro-3-(piperazin-1-yl)quinoxalin-2-yl)acetate;
cyclohexylmethyl 2-cyano-2-(6-nitro-3-(piperazin-1-yl)quinoxalin-2-yl)acetate;
cyclohexylmethyl 2-cyano-2-(6-phenyl-3-(piperazin-1-yl)quinoxalin-2-yl)acetate;
cyclohexylmethyl 2-cyano-2-(6-(piperazin-1-yl)pyrimidin-4-yl)acetate;
cyclohexylmethyl 2-cyano-2-(6-phenyl-3-(piperazin-1-yl)pyrazin-2-yl)acetate;
cyclohexylmethyl 2-cyano-2-(6-(4-hydroxyphenyl)-3-(piperazin-1-yl)quinoxalin-2-yl)acetate;
cyclohexylmethyl 2-cyano-2-(6-(3-fluorophenyl)-3-(piperazin-1-yl)quinoxalin-2-yl)acetate;
cyclohexylmethyl 2-cyano-2-(3-(piperazin-1-yl)quinolin-2-yl)acetate;
cyclohexylmethyl 2-cyano-2-(6-(4-fluorophenyl)-3-(piperazin-1-yl)quinoxalin-2-yl)acetate;
5-cyclohexyl-3-oxo-2-(3-(piperazin-1-yl)pyrazin-2-yl)pentanenitrile;
5-cyclohexyl-3-oxo-2-(3-(piperazin-1-yl)quinoxalin-2-yl)pentanenitrile;
cyclohexyl 2-(7-amino-3-(piperazin-1-yl)quinoxalin-2-yl)-2-cyanoacetate; or
cyclohexyl 2-(5-amino-3-(piperazin-1-yl)quinoxalin-2-yl)-2-cyanoacetate.

In some embodiments, the compound is not cyclohexyl 2-cyano-2-(3-(4-ethylpiperazin-1-yl)quinoxalin-2-yl)acetate (compound 1), benzyl 2-cyano-2-(3-(4-methylpiperazin-1-yl)quinoxalin-2-yl)acetate (compound 2), 2-ethylbutyl 2-cyano-2-(3-(4-ethylpiperazin-1-yl)quinoxalin-2-yl)acetate (compound 3), cyclohexyl 2-cyano-2-(3-(4-methylpiperazin-1-yl)quinoxalin-2-yl)acetate (compound 4), isopropyl 2-cyano-2-(3-(4-methylpiperazin-1-yl)quinoxalin-2-yl)acetate (compound 5), N-benzyl-2-cyano-2-(3-(4-methylpiperazin-1-yl)quinoxalin-2-yl)acetamide, or 2-(1-methyl-1H-imidazol-2-yl)-2-(3-(4-methylpiperazin-1-yl)quinoxalin-2-yl)acetonitrile. In some embodiments, the compound is not 2-cyano-N-(3-methoxybenzyl)-2-(3-(4-methylpiperazin-1-yl)quinoxalin-2-yl)acetamide. In some embodiments, the compound is not 2-cyano-N-(3-methoxybenzyl)-2-(3-(piperidin-1-yl)quinoxalin-2-yl)acetamide. In some embodiments, the compound is not 2-cyano-N-(3-methoxybenzyl)-2-(3-morpholinoquinoxalin-2-yl)acetamide. In some embodiments, the compound is not 1-(3-(1-cyano-3-(cyclohexylamino)-2-oxopropyl)quinoxalin-2-yl)piperidine-4-carboxamide. In some embodiments, the compound is not cyclohexyl 2-cyano-2-(3-(4-(4-fluorophenyl)piperazin-1-yl)quinoxalin-2-yl)acetate. In some embodiments, the compound having the structure of formula (I) may not be cyclohexyl 2-cyano-2-(3-(4-ethylpiperazin-1-yl)quinoxalin-2-yl)acetate (compound 1). In some embodiments, the compound having the structure of formula (I) may not be benzyl 2-cyano-2-(3-(4-methylpiperazin-1-yl)quinoxalin-2-yl)acetate (compound 2). In some embodiments, the compound having the structure of formula (I) may not be 2-ethylbutyl 2-cyano-2-(3-(4-ethylpiperazin-1-yl)quinoxalin-2-yl)acetate. In some embodiments, the compound having the structure of formula (I) may not be (compound 3). In some embodiments, the compound having the structure of formula (I) may not be cyclohexyl 2-cyano-2-(3-(4-methylpiperazin-1-yl)quinoxalin-2-yl)acetate. In some embodiments, the compound having the structure of formula (I) may not be (compound 4). In some embodiments, the compound having the structure of formula (I) may not be isopropyl 2-cyano-2-(3-(4-methylpiperazin-1-yl)quinoxalin-2-yl)acetate (compound 5). In some embodiments, the compound having the structure of formula (I) may not be benzyl 2-(3-(4-methylpiperazin-1-yl)quinoxalin-2-yl)but-3-ynoate. In some embodiments, the compound having the structure of formula (I) may not be benzyl 2-(3-(4-methylpiperazin-1-yl)quinoxalin-2-yl)propanoate.

In some embodiments, the compound having the structure of formula (I) may not be benzyl 2-cyano-2-(3-(4-methylpiperazin-1-yl)quinoxalin-2-yl)propanoate. In some embodiments, the compound having the structure of formula (I) may not be N-benzyl-2-cyano-2-(3-(4-methylpiperazin-1-yl)quinoxalin-2-yl)acetamide. In some embodiments, the compound having the structure of formula (I) may not be 1-phenylethyl 2-cyano-2-(3-(4-methylpiperazin-1-yl)quinoxalin-2-yl)acetate. In some embodiments, the compound having the structure of formula (I) may not be 2-phenylpropan-2-yl 2-cyano-2-(3-(4-methylpiperazin-1-yl)quinoxalin-2-yl)acetate. In some embodiments, the compound having the structure of formula (I) may not be 3-hydroxy-2-(3-(4-methylpiperazin-1-yl)quinoxalin-2-yl)propanenitrile. In some embodiments, the compound having the structure of formula (I) may not be 3-methoxy-2-(3-(4-methylpiperazin-1-yl)quinoxalin-2-yl)propanenitrile. In some embodiments, the compound having the structure of formula (I) may not be 3-(benzyloxy)-2-(3-(4-methylpiperazin-1-yl)quinoxalin-2-yl)propanenitrile. In some embodiments, the compound having the structure of formula (I) may not be N-(cyano(3-(4-methylpiperazin-1-yl)quinoxalin-2-yl)methyl)-2-phenylacetamide. In some embodiments, the compound having the structure of formula (I) may not be benzyl N-cyano(3-(4-methylpiperazin-1-yl)quinoxalin-2-yl)carbamate. In some embodiments, the compound having the structure of formula (I) may not be 1-(3-(4-methylpiperazin-1-yl)quinoxalin-2-yl)but-3-en-2-one. In some embodiments, the compound having the structure of formula (I) may not be N-(3-(4-methylpiperazin-1-yl)quinoxalin-2-yl)acrylamide.

In some embodiments, the compound having the structure of formula (I) may not be benzyl 2-(3-(2-cyano-4-methylpiperazin-1-yl)quinoxalin-2-yl)acetate. In some embodiments, the compound having the structure of formula (I) may not be benzyl 2-cyano-2-(3-(2,4-dimethylpiperazin-1-yl)quinoxalin-2-yl)acetate. In some embodiments, the compound having the structure of formula (I) may not be benzyl 2-cyano-2-(3-(1-methylpiperidin-4-yl)quinoxalin-2-yl)acetate. In some embodiments, the compound having the structure of formula (I) may not be benzyl 2-cyano-2-(3-(4-fluoro-1-methylpiperidin-4-yl)quinoxalin-2-yl)acetate. In some embodiments, the compound having the structure of formula (I) may not be benzyl 2-cyano-2-(3-(4-hydroxy-1-methylpiperidin-4-yl)quinoxalin-2-yl)acetate. In some embodiments, the compound having the structure of formula (I) may not be N-(cyano(3-(4-methylpiperazin-1-yl)quinoxalin-2-yl)methyl)acetamide. In some embodiments, the compound having the structure of formula (I) may not be benzyl 2-(3-(4-aminopiperidin-1-yl)quinoxalin-2-yl)-2-cyanoacetate. In some embodiments, the compound having the structure of formula (I) may not be benzyl 2-cyano-2-(3-(4-(methylamino)piperidin-1-yl)quinoxalin-2-yl)acetate. In some embodiments, the compound having the structure of formula (I) may not be benzyl 2-cyano-2-(3-(4-(dimethylamino)piperidin-1-yl)quinoxalin-2-yl)acetate. In some embodiments, the compound having the structure of formula (I) may not be 2-(1-benzyl-1H-imidazol-2-yl)-2-(3-(4-methylpiperazin-1-yl)quinoxalin-2-yl)acetonitrile. In some embodiments, the compound having the structure of formula (I) may not be 2-(1-methyl-1H-imidazol-2-yl)-2-(3-(4-methylpiperazin-1-yl)quinoxalin-2-yl)acetonitrile. In some embodiments, the compound having the structure of formula (I) may not be 2-(5-benzyl-1,3,4-oxadiazol-2-yl)-2-(3-(4-methylpiperazin-1-yl)quinoxalin-2-yl)acetonitrile. In some embodiments, the compound having the structure of formula (I) may not be 2-(5-methyl-1,3,4-oxadiazol-2-yl)-2-(3-(4-methylpiperazin-1-yl)quinoxalin-2-yl)acetonitrile. In some embodiments, the compound having the structure of formula (I) may not be benzyl 2-cyano-2-(3-(4-methylpiperazin-1-yl)quinolin-2-yl)acetate. In some embodiments, the compound having the structure of formula (I) may not be benzyl 2-cyano-2-(2-(4-methylpiperazin-1-yl)quinolin-3-yl)acetate. In some embodiments, the compound having the structure of formula (I) may not be benzyl 2-cyano-2-(2-(4-methylpiperazin-1-yl)-1,5-naphthyridin-3-yl)acetate. In some embodiments, the compound having the structure of formula (I) may not be benzyl 2-cyano-2-(3-(4-methylpiperazin-1-yl)-1,5-naphthyridin-2-yl)acetate. In some embodiments, the compound having the structure of formula (I) may not be benzyl 2-cyano-2-(2-(4-methylpiperazin-1-yl)-4-oxo-1,4-dihydroquinolin-3-yl)acetate. In some embodiments, the compound having the structure of formula (I) may not be benzyl 2-cyano-2-(3-(4-methylpiperazin-1-yl)-4-oxo-1,4-dihydroquinolin-2-yl)acetate. In some embodiments, the compound having the structure of formula (I) may not be benzyl 2-cyano-2-(5,6-dimethyl-3-(4-methylpiperazin-1-yl)pyrazin-2-yl)acetate. In some embodiments, the compound having the structure of formula (I) may not be benzyl 2-cyano-2-(3-(4-methylpiperazin-1-yl)pyrazin-2-yl)acetate. In some embodiments, the compound having the structure of formula (I) may not be benzyl 2-cyano-2-(4-fluoro-3-(4-methylpiperazin-1-yl)quinolin-2-yl)acetate. In some embodiments, the compound having the structure of formula (I) may not be benzyl 2-cyano-2-(4-fluoro-2-(4-methylpiperazin-1-yl)quinolin-3-yl)acetate. In some embodiments, the compound having the structure of formula (I) may not be 4-fluorobenzyl 2-cyano-2-(3-(4-methylpiperazin-1-yl)quinoxalin-2-yl)acetate. In some embodiments, the compound having the structure of formula (I) may not be 2-ethylbutyl 2-cyano-2-(3-(4-methylpiperazin-1-yl)quinoxalin-2-yl)acetate. In some embodiments, the compound having the structure of formula (I) may not be 2-ethylbutyl 2-cyano-2-(3-(piperazin-1-yl)quinoxalin-2-yl)acetate. In some embodiments, the compound having the structure of formula (I) may not be 2,2 dimethyl propyl 2-cyano-2-(3-(piperazin-1-yl)quinoxalin-2-yl)acetate. In some embodiments, the compound having the structure of formula (I) may not be 2,2 dimethyl propyl 2-cyano-2-(3-(methylpiperazin-1-yl)quinoxalin-2-yl)acetate. In some embodiments, the compound having the structure of formula (I) may not be 2-fluorobenzyl 2-cyano-2-(3-(piperazin-1-yl)quinoxalin-2-yl)acetate. In some embodiments, the compound having the structure of formula (I) may not be 3-fluorobenzyl 2-cyano-2-(3-(piperazin-1-yl)quinoxalin-2-yl)acetate. In some embodiments, the compound having the structure of formula (I) may not be 4-fluorobenzyl 2-cyano-2-(3-(piperazin-1-yl)quinoxalin-2-yl)acetate. In some embodiments, the compound having the structure of formula (I) may not be 3-aminobenzyl 2-cyano-2-(3-(piperazin-1-yl)quinoxalin-2-yl)acetate. In some embodiments, the compound having the structure of formula (I) may not be 2-ethylbutyl 2-cyano-2-(3-(4-(amino)piperidin-1-yl)quinoxalin-2-yl)acetate. In some embodiments, the compound having the structure of formula (I) may not be 2-ethylbutyl 2-cyano-2-(3-(4-(aminomethyl)piperidin-1-yl)quinoxalin-2-yl)acetate. In some embodiments, the compound having the structure of formula (I) may not be cyclohexyl 2-cyano-2-(3-(4-methylpiperazin-1-yl)quinoxalin-2-yl)acetate. In some embodiments, the compound having the structure of formula (I) may not be pentan-3-yl 2-cyano-2-(3-(3-isopropylpiperazin-1-yl)quinoxalin-2-yl)acetate. In some embodiments, the compound having the structure of formula (I) may not be cycloheptylmethyl 2-cyano-2-(3-(piperazin-1-yl)quinoxalin-2-yl)acetate. In some embodiments, the compound having the structure of formula (I) may not be cyclohexylmethyl 2-cyano-2-(3-(4-methylpiperazin-1-yl)quinoxalin-2-yl)acetate. In some embodiments, the compound having the structure of formula (I) may not be cyclohexylmethyl 2-cyano-2-(3-(4-methylpiperazin-1-yl)quinoxalin-2-yl)acetate. In some embodiments, the compound having the structure of formula (I) may not be 2-ethylbutyl 2-cyano-2-(3-(3,3-dimethylpiperazin-1-yl)quinoxalin-2-yl)acetate. In some embodiments, the compound having the structure of formula (I) may not be isobutyl 2-(3-(4-carbamoylpiperidin-1-yl)quinoxalin-2-yl)-2-cyanoacetate. In some embodiments, the compound having the structure of formula (I) may not be pyridin-4-ylmethyl 2-cyano-2-(3-(4-methylpiperidin-1-yl)quinoxalin-2-yl)acetate. In some embodiments, the compound having the structure of formula (I) may not be cyclopentylmethyl 2-cyano-2-(3-(piperazin-1-yl)quinoxalin-2-yl)acetate. In some embodiments, the compound having the structure of formula (I) may not be 2-ethylbutyl 2-cyano-2-(3-(3-phenylpiperazin-1-yl)quinoxalin-2-yl)acetate. In some embodiments, the compound having the structure of formula (I) may not be 2-ethylbutyl 2-cyano-2-(3-((S)-3-methylpiperazin-1-yl)quinoxalin-2-yl)acetate. In some embodiments, the compound having the structure of formula (I) may not be 4-fluorobenzyl 2-cyano-2-(3-(piperazin-1-yl)quinoxalin-2-yl)acetate. In some embodiments, the compound having the structure of formula (I) may not be 2-ethylbutyl 2-cyano-2-(3-(3-ethylpiperazin-1-yl)quinoxalin-2-yl)acetate. In some embodiments, the compound having the structure of formula (I) may not be 2-ethylbutyl 2-cyano-2-(3-(3-(hydroxymethyl)piperazin-1-yl)quinoxalin-2-yl)acetate. In some embodiments, the compound having the structure of formula (I) may not be cyclohexylmethyl 2-cyano-2-(3-(3-methylpiperazin-1-yl)quinoxalin-2-yl)acetate. In some embodiments, the compound having the structure of formula (I) may not be methyl 4-(3-(1-cyano-2-(2-ethylbutoxy)-2-oxoethyl)quinoxalin-2-yl)piperazine-2-carboxylate. In some embodiments, the compound having the structure of formula (I) may not be 3-(2-ethylbutoxy)-2-(3-(3-oxopiperazin-1-yl)quinoxalin-2-yl)but-3-enenitrile. In some embodiments, the compound having the structure of formula (I) may not be 2-ethylbutyl 2-cyano-2-(3-(3-oxopiperazin-1-yl)quinoxalin-2-yl)acetate. In some embodiments, the compound having the structure of formula (I) may not be 2-cyano-N-(cyclohexylmethyl)-2-(3-(piperazin-1-yl)quinoxalin-2-yl)acetamide. In some embodiments, the compound having the structure of formula (I) may not be pyridin-3-ylmethyl 2-cyano-2-(3-(piperazin-1-yl)quinoxalin-2-yl)acetate. In some embodiments, the compound having the structure of formula (I) may not be 3-aminobenzyl 2-cyano-2-(3-(piperazin-1-yl)quinoxalin-2-yl)acetate. In some embodiments, the compound having the structure of formula (I) may not be cyclohexylmethyl 2-cyano-2-(3-(piperazin-1-yl)quinoxalin-2-yl)acetate. In some embodiments, the compound having the structure of formula (I) may not be 2-ethylbutyl 2-cyano-2-(3-(3-methylpiperazin-1-yl)quinoxalin-2-yl)acetate. In some embodiments, the compound having the structure of formula (I) may not be naphthalen-2-ylmethyl 2-cyano-2-(3-(piperazin-1-yl)quinoxalin-2-yl)acetate. In some embodiments, the compound having the structure of formula (I) may not be 4-fluorobenzyl 2-cyano-2-(3-(4-methylpiperazin-1-yl)quinoxalin-2-yl)acetate. In some embodiments, the compound having the structure of formula (I) may not be 2-ethylbutyl 2-cyano-2-(3-((R)-3-methylpiperazin-1-yl)quinoxalin-2-yl)acetate. In some embodiments, the compound having the structure of formula (I) may not be cyclohexylmethyl 2-cyano-2-(8-fluoro-3-(piperazin-1-yl)quinoxalin-2-yl)acetate. In some embodiments, the compound having the structure of formula (I) may not be cyclohexylmethyl 2-cyano-2-(6-fluoro-3-(piperazin-1-yl)quinoxalin-2-yl)acetate. In some embodiments, the compound having the structure of formula (I) may not be cyclohexylmethyl 2-cyano-2-(6-(2-fluorophenyl)-3-(piperazin-1-yl)quinoxalin-2-yl)acetate. In some embodiments, the compound having the structure of formula (I) may not be cyclohexylmethyl 2-cyano-2-(6-(2-hydroxyphenyl)-3-(piperazin-1-yl)quinoxalin-2-yl)acetate. In some embodiments, the compound having the structure of formula (I) may not be N-benzyl-2-cyano-2-(3-(piperazin-1-yl)quinoxalin-2-yl)acetamide. In some embodiments, the compound having the structure of formula (I) may not be cyclohexylmethyl 2-cyano-2-(5-fluoro-3-(piperazin-1-yl)quinoxalin-2-yl)acetate. In some embodiments, the compound having the structure of formula (I) may not be cyclohexylmethyl 2-cyano-2-(6-nitro-3-(piperazin-1-yl)quinoxalin-2-yl)acetate. In some embodiments, the compound having the structure of formula (I) may not be cyclohexylmethyl 2-cyano-2-(6-phenyl-3-(piperazin-1-yl)quinoxalin-2-yl)acetate. In some embodiments, the compound having the structure of formula (I) may not be cyclohexylmethyl 2-cyano-2-(6-(piperazin-1-yl)pyrimidin-4-yl)acetate. In some embodiments, the compound having the structure of formula (I) may not be cyclohexylmethyl 2-cyano-2-(6-phenyl-3-(piperazin-1-yl)pyrazin-2-yl)acetate. In some embodiments, the compound having the structure of formula (I) may not be cyclohexylmethyl 2-cyano-2-(6-(4-hydroxyphenyl)-3-(piperazin-1-yl)quinoxalin-2-yl)acetate. In some embodiments, the compound having the structure of formula (I) may not be cyclohexylmethyl 2-cyano-2-(6-(3-fluorophenyl)-3-(piperazin-1-yl)quinoxalin-2-yl)acetate. In some embodiments, the compound having the structure of formula (I) may not be cyclohexylmethyl 2-cyano-2-(3-(piperazin-1-yl)quinolin-2-yl)acetate. In some embodiments, the compound having the structure of formula (I) may not be cyclohexylmethyl 2-cyano-2-(6-(4-fluorophenyl)-3-(piperazin-1-yl)quinoxalin-2-yl)acetate. In some embodiments, the compound having the structure of formula (I) may not be 5-cyclohexyl-3-oxo-2-(3-(piperazin-1-yl)pyrazin-2-yl)pentanenitrile. In some embodiments, the compound having the structure of formula (I) may not be 5-cyclohexyl-3-oxo-2-(3-(piperazin-1-yl)quinoxalin-2-yl)pentanenitrile. The invention further includes a pharmaceutical composition comprising the compound of the invention and a pharmaceutically acceptable carrier.

In certain embodiments, the pharmaceutical composition further comprises at least one additional agent that is useful to treat the diseases or disorders contemplated herein. In certain embodiments, the compound of the invention and the additional agent are co-formulated in the composition.

The compounds of the present invention may be synthesized using techniques well-known in the art of organic synthesis. The starting materials and intermediates required for the synthesis may be obtained from commercial sources or synthesized according to methods known to those skilled in the art.

In a non-limiting aspect, certain compounds contemplated within the invention may be prepared using the following synthetic scheme:

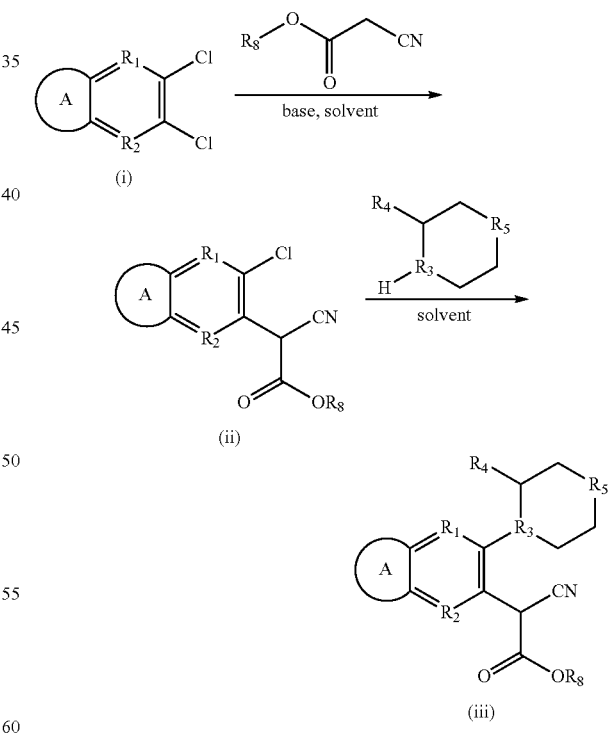

According to the scheme, the ortho-dichloro aryl compound (i) may be reacted with the $R_8$ ester of cyanoacetic acid in the presence of base (such as but not limited to potassium or sodium carbonate) in a solvent (such as, but not limited to, dimethylformamide (DMF) or dimethylsulfoxide (DMSO)), in the optional presence of an ammonium salt (such as, but not limited to, benzyltriethylammonium chloride), to generate the 2-aryl-2-cyano acetate ester (ii). Displacement of the aromatic chloride in (ii) with a nucleophile generates compound (iii) contemplated within the invention.

In certain embodiments, the compounds of the invention are useful in the methods of the invention in combination with at least one additional agent useful for treating or preventing a disease or disorder contemplated within the invention. This additional agent may comprise compounds identified herein or compounds, e.g., commercially available compounds, known to treat, prevent or reduce the symptoms of a hematological cancer, such as, but not limited to, AML and MDS.

In certain embodiments, the at least one additional agent is an anticancer agent. In other embodiments, the at least one additional agent can be selected from lenalidomide, azacitidine, decitabine, erythropoietin, daunorubicin, idarubicin, cytarabine, mitoxantrone, etoposide, gilteritinib, ATRA (all-trans retinoic acid), or arsenic trioxide.

In one aspect, the at least one additional agent includes, but is not limited to, a chemotherapeutic agent, an anti-cell proliferation agent or any combination thereof. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents are so named because of their ability to add alkyl groups to many electronegative groups under conditions present in cells, thereby interfering with DNA replication to prevent cancer cells from reproducing. Most alkylating agents are cell cycle non-specific. In some aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

Antitumor antibiotics generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

Miscellaneous agents include chemotherapeutics such as bleomycin, hydroxyurea, L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In certain embodiments, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In other embodiments, the cytotoxic agent is TNF-α, gelonin, Prodigiosin, a ribosome-inhibiting protein (RIP), *Pseudomonas* exotoxin, *Clostridium difficile* Toxin B, *Helicobacter pylori* VacA, *Yersinia enterocolitica* YopT, Violacein, diethylenetriaminepentaacetic acid, irofulven, Diptheria Toxin, mitogillin, ricin, botulinum toxin, cholera toxin, saporin 6, or a combination thereof.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In one aspect, the invention includes a method of treating or preventing a cancer in a subject. In one aspect, the invention includes a method of treating a cancer in a subject. In certain embodiments, the method comprises administering to the subject a therapeutically effective amount of at least one compound contemplated within the invention. In other embodiments, the at least one compound is formulated in a pharmaceutical composition. In yet other embodiments, the compound is a compound of formula (I), or a salt thereof, as recited elsewhere herein.

In certain embodiments, the cancer comprises a hematological cancer. In other embodiments, the hematological cancer comprises acute myeloid leukemia (AML) and/or myelodysplastic syndrome (MDS), including 5q-MDS. In yet other embodiments, the cancer comprises colorectal cancer. In some embodiments, the colorectal cancer may comprise colon and/or rectal cancer.

In certain embodiments, the compound or composition is administered to the subject by at least one route selected from oral, rectal, mucosal (e.g., by oral or nasal inhalation), transmucosal, topical (transdermal), and intravenous, intradermal, intramuscular, subcutaneous, intracutaneous, intrauterine, epidural and intracerebroventricular injections. In other embodiments, the subject is further administered at least one additional agent useful for treating or preventing a cancer. In yet other embodiments, the subject is a mammal. In yet other embodiments, the mammal is human. In yet other embodiments, the subject is not responsive to one or more commercially available and/useful anticancer agents.

The compositions of the present invention may contain a pharmaceutical acceptable carrier, excipient and/or diluent, and may be administered by a suitable method to a subject. The compositions of the present invention may be formulated in various forms, including oral dosage forms or sterile injectable solutions, according to any conventional method known in the art. In other embodiments, the compositions may also be used as an inhalation-type drug delivery system. In yet other embodiments, the compositions of the invention may be formulated for injectable solutions.

The compositions may be formulated as powders, granules, tablets, capsules, suspensions, emulsions, syrup, aerosol, preparations for external application, suppositories and sterile injectable solutions. Suitable formulations known in the art are disclosed in, for example, Remington's Pharmaceutical Science (Mack Publishing Company, Easton Pa.). Carriers, excipients and diluents that may be contained in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propyl hydroxylbenzoate, talc, magnesium stearate or mineral oil.

Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g., BHT), buffering agents (e.g. phosphate or citrate buffers), and effervescent agents such as citrate/bicarbonate mixtures. Capsule formulations may be of the hard gelatin or soft gelatin variety and can contain the active component in solid, semi-solid, or liquid form. Gelatin capsules can be formed from animal gelatin or synthetic or plant derived equivalents thereof. The solid dosage forms (e.g., tablets, capsules) can be coated or un-coated, but typically have a coating, for example a protective film coating (e.g. a wax or varnish) or a release controlling coating. The coating (e.g., a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum. Alternatively or additionally, the coating can be used as a taste masking agent to mask unpleasant tastes such as bitter tasting drugs. The coating may contain sugar or other agents that assist in masking unpleasant tastes. Instead of, or in addition to, a coating, the compound can be presented in a solid matrix comprising a release controlling agent, for example a release delaying agent that may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art. The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient has access to the package insert contained in the patient pack, normally missing in patient prescriptions. The inclusion of a package insert has been shown to improve patient compliance with the physician's instructions. Each tablet, capsule, caplet, pill, etc. can be a single dose, with a dose, for example, as herein discussed, or a dose can be two or more tablets, capsules, caplets, pills, and so forth; for example if a tablet, capsule and so forth is 125 mg and the dose is 250 mg, the patient may take two tablets, capsules and the like, at each interval there is to administration.

The compositions of the present invention may be formulated with commonly used diluents or excipients, such as fillers, extenders, binders, wetting agents, disintegrants, or surfactants. Solid formulations for oral administration include tablets, pills, powders, granules, or capsules, and such solid formulations comprise, in addition to the composition, at least one excipient, for example, starch, calcium carbonate, sucrose, lactose or gelatin. In addition to simple excipients, lubricants such as magnesium stearate or talc may also be used. Liquid formulations for oral administration include suspensions, solutions, emulsions and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, or injectable esters such as ethyl oleate may be used. As the base of the suppositories, witepsol, Macrogol, Tween 61, cacao butter, laurin fat, or glycerogelatin may be used.

The dose of the pharmaceutical compositions of the present invention varies depending on the patient's condition and weight, the severity of the disease, the type of drug, and the route and period of administration and may be suitably selected by those skilled in the art. In some aspects, the pharmaceutical composition of the present invention may be administered at a dose of about 0.01-100 mg/kg/day. The administration may be anywhere from 1 to 4 times daily, e.g., once, twice, three times or four times daily. The maximum amount administered in a 24 hour period may be up to about 1500 mg. The administration may be over a course of 2 to 30 days, e.g., 3 to 21 days, such as 7, 10 or 14 days. The skilled person can adjust dosing depending on the subject's body weight and overall health condition and the purpose for administering the compound. Repeated courses of treatment may be pursued depending on the response obtained.

The compositions of the present invention may be administered to a subject by various routes. All modes of administration are contemplated, for example, orally, rectally, mucosally (e.g., by oral or nasal inhalation), transmucosally, topically (transdermal), or by intravenous, intradermal, intramuscular, subcutaneous, intracutaneous, intrauterine, epidural or intracerebroventricular injection.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the assay, screening, and therapeutic methods of the invention, and are not intended to limit the scope of what the inventor(s) regard(s) as the invention.

EXAMPLES

The invention is now described with reference to the following Examples. These Examples are provided for the purpose of illustration only, and the invention is not limited to these Examples.

Unless noted otherwise, the starting materials for the synthesis described herein were obtained from commercial sources or known synthetic procedures and were used without further purification.

Example 1: Identification of CSNK1A1 Inhibitors

In order to identify inhibitors of CSNK1A1, the CSNK1A1 knockdown signatures in CMap were compared to all CMap compound signatures, and resultant compounds were ranked by strength of signature similarity. The top ranked compound from this analysis (compound 1) was predicted to act as a CSNK1A1 inhibitor.

Figure 2:
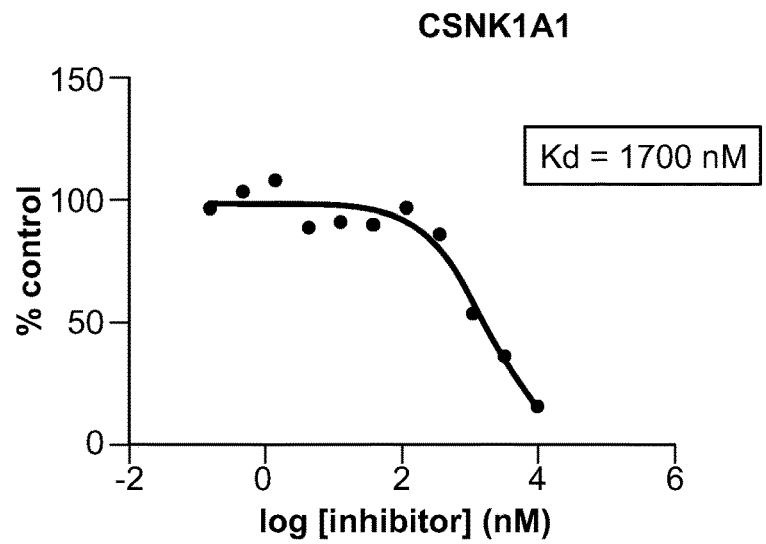
FIG. 2 comprises a set of graphs illustrating experimental $K_d$ values for compound 1 against various casein 1 kinase family members.
Figure 2:
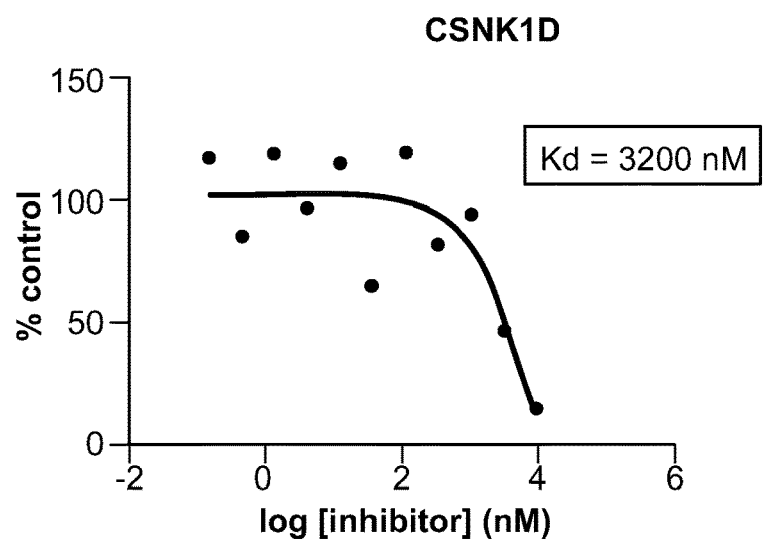
Figure 2:
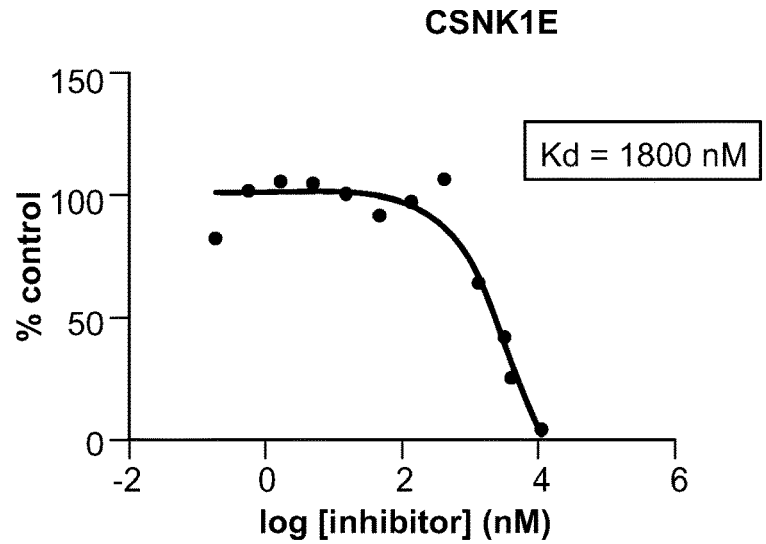
Figure 3:
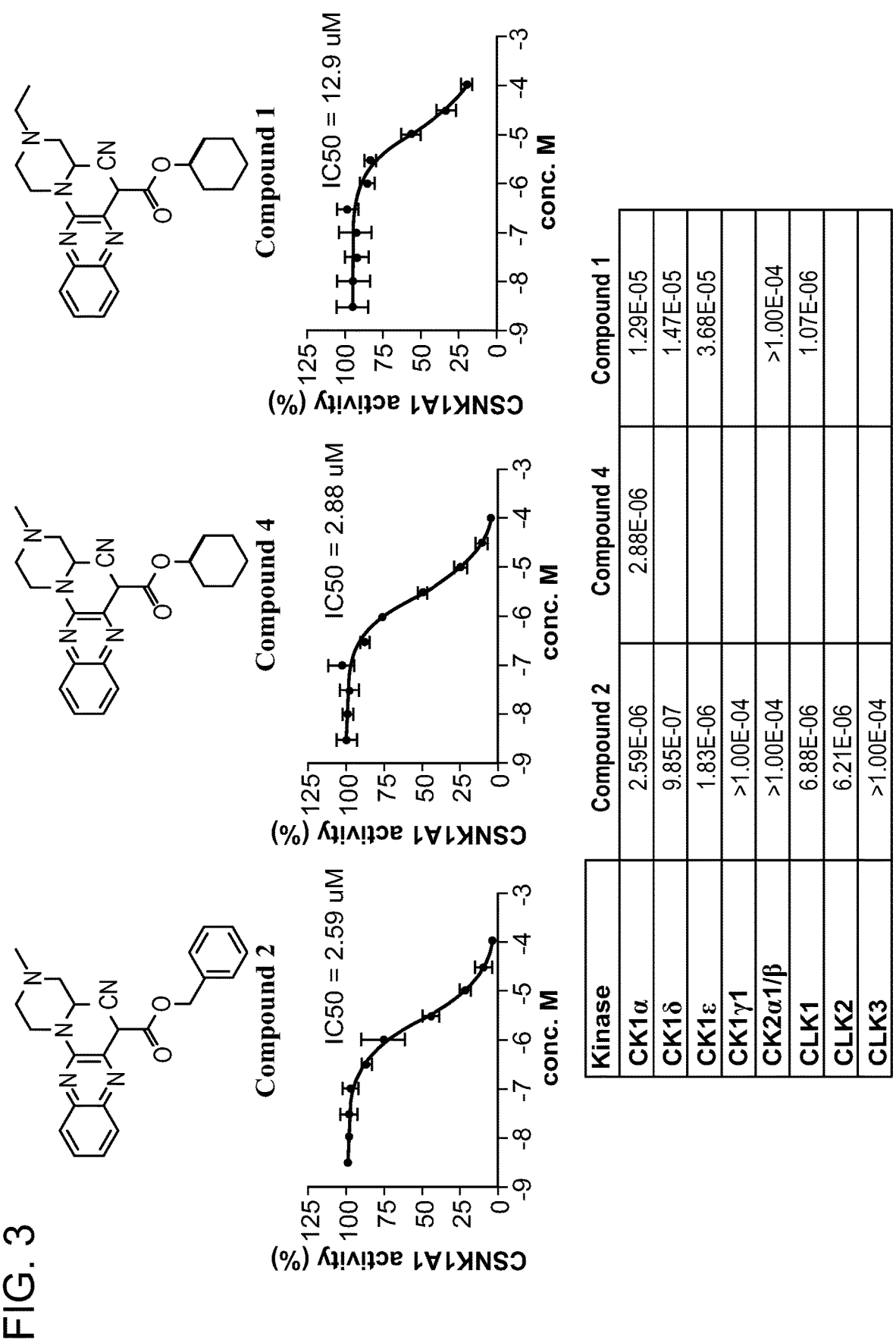
FIG. 3 comprises a set of graphs and table illustrating experimental $IC_{50}$ values against various kinases for compounds 2, 4 and 1.

The CMap prediction was confirmed using Kinomescan (FIG. 1). Compound 1 bound to only six out of over 400 kinases tested in the assay, including CSNK1A1. Upon confirmatory testing, compound 1 inhibited CSNK1A1 with $K_d$ of 1,700 nM and CSNK1D with $K_d$ of 3,200 nM (FIG. 2). Analogs of this initial hit also showed selective inhibition of CSNK1A1 (FIG. 3).

$IC_{50}$ values for exemplary compounds are recited in Table 1.

TABLE 1

| Structure | Nomenclature | $IC_{50}$ (M) |
|---|---|---|
| 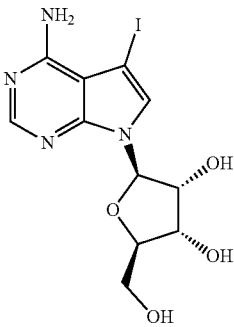 [SMILES: Nc1ncnc2c1c(I)cn2[C@@H]1O[C@H](CO)[C@@H](O)[C@H]1O] | 5-iodotubercidin | $2.87 \times 10^{-7}$ |

TABLE 1-continued

| Structure | Nomenclature | IC$_{50}$ (M) |
|---|---|---|
| 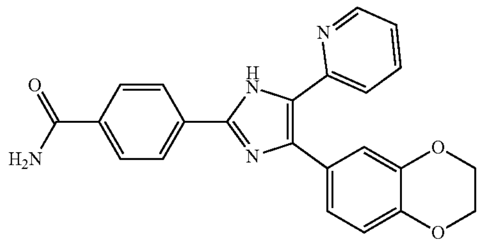 [SMILES: NC(=O)c1ccc(-c2nc(-c3ccc4c(c3)OCCO4)c(-c3ccccn3)[nH]2)cc1] | D-4476 | $3.21 \times 10^{-7}$ |
| 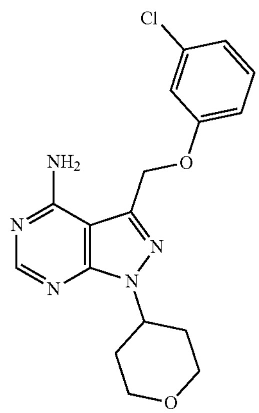 [SMILES: Nc1ncnc2c1c(COc1cccc(Cl)c1)nn2C1CCOCC1] | PF4800567 | $8.57 \times 10^{-7}$ |
| 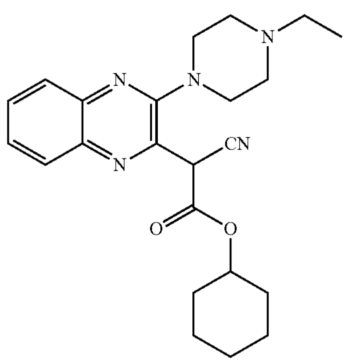 [SMILES: CCN1CCN(c2nc3ccccc3nc2C(C#N)C(=O)OC2CCCCC2)CC1] | cyclohexyl 2-cyano-2-(3-(4-ethylpiperazin-1-yl)quinoxalin-2-yl)acetate (compound 1) | $1.29 \times 10^{-5}$ |
| 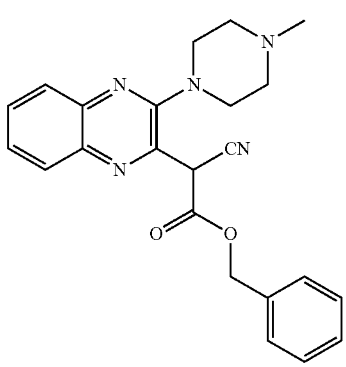 [SMILES: CN1CCN(c2nc3ccccc3nc2C(C#N)C(=O)OCc2ccccc2)CC1] | benzyl 2-cyano-2-(3-(4-methylpiperazin-1-yl)quinoxalin-2-yl)acetate (compound 2) | $2.59 \times 10^{-6}$ |

TABLE 1-continued

| Structure | Nomenclature | IC$_{50}$ (M) |
|---|---|---|
| 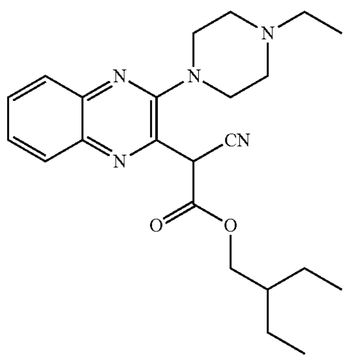 [SMILES: CCC(CC)COC(=O)C(C#N)c1nc2ccccc2nc1N1CCN(CC)CC1] | 2-ethylbutyl 2-cyano-2-(3-(4-ethylpiperazin-1-yl)quinoxalin-2-yl)acetate (compound 3) | $5.00 \times 10^{-6}$ |
| 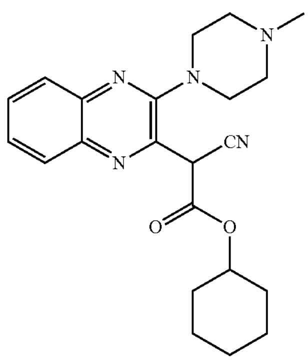 [SMILES: CN1CCN(c2nc3ccccc3nc2C(C#N)C(=O)OC2CCCCC2)CC1] | cyclohexyl 2-cyano-2-(3-(4-methylpiperazin-1-yl)quinoxalin-2-yl)acetate (compound 4) | $3.18 \times 10^{-6}$ |
| 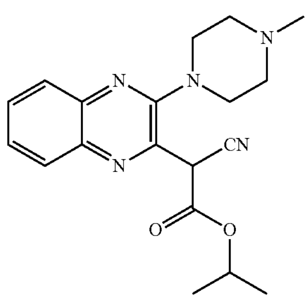 [SMILES: CC(C)OC(=O)C(C#N)c1nc2ccccc2nc1N1CCN(C)CC1] | isopropyl 2-cyano-2-(3-(4-methylpiperazin-1-yl)quinoxalin-2-yl)acetate (compound 5) | $5.46 \times 10^{-5}$ |
| 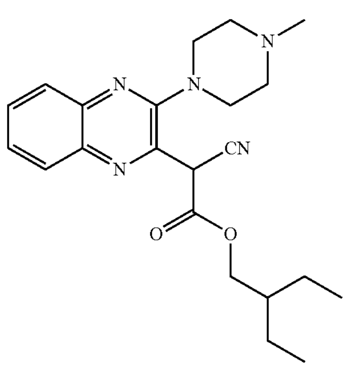 [SMILES: CCC(CC)COC(=O)C(C#N)c1nc2ccccc2nc1N1CCN(C)CC1] | 2-ethylbutyl 2-cyano-2-(3-(4-(methylpiperazin-1-yl)quinoxalin-2-yl)acetate | $3.99 \times 10^{-7}$ |

TABLE 1-continued

| Structure | Nomenclature | IC$_{50}$ (M) |
|---|---|---|
| 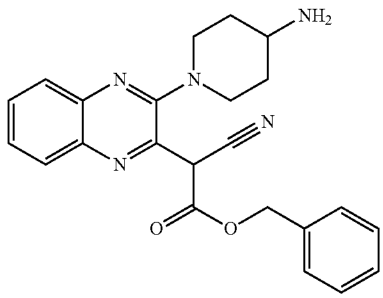 [SMILES: N#CC(C(=O)OCc1ccccc1)c1nc2ccccc2nc1N1CCC(N)CC1] | benzyl 2-(3-(4-aminopiperidin-1-yl)quinoxalin-2-yl)-2-cyanoacetate | $1.89 \times 10^{-6}$ |
| 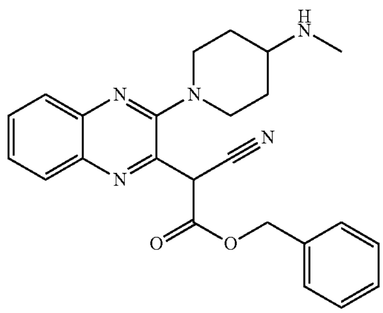 [SMILES: CNC1CCN(c2nc3ccccc3nc2C(C#N)C(=O)OCc2ccccc2)CC1] | benzyl 2-cyano-2-(3-(4-(methylamino)piperidin-1-yl)quinoxalin-2-yl)acetate | $4.39 \times 10^{-6}$ |
| 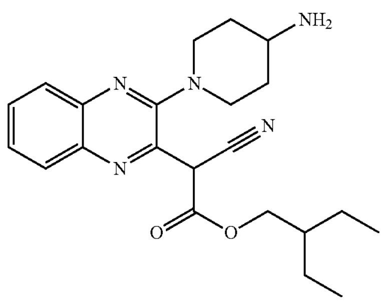 [SMILES: CCC(CC)COC(=O)C(C#N)c1nc2ccccc2nc1N1CCC(N)CC1] | 2-ethylbutyl 2-cyano-2-(3-(4-(amino)piperidin-1-yl)quinoxalin-2-yl)acetate | $3.32 \times 10^{-6}$ |
| 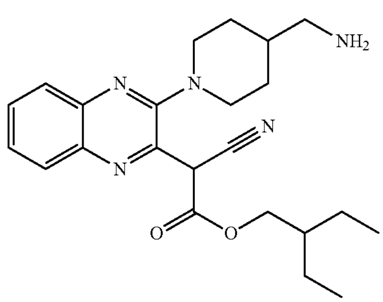 [SMILES: CCC(CC)COC(=O)C(C#N)c1nc2ccccc2nc1N1CCC(CN)CC1] | 2-ethylbutyl 2-cyano-2-(3-(4-(aminomethyl)piperidin-1-yl)quinoxalin-2-yl)acetate | $1.75 \times 10^{-6}$ |
| 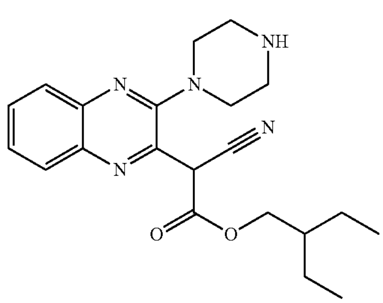 [SMILES: CCC(CC)COC(=O)C(C#N)c1nc2ccccc2nc1N1CCNCC1] | 2-ethylbutyl 2-cyano-2-(3-(4-(piperazin-1-yl)quinoxalin-2-yl)acetate | $9.4 \times 10^{-8}$ |

TABLE 1-continued

| Structure | Nomenclature | IC$_{50}$ (M) |
|---|---|---|
| 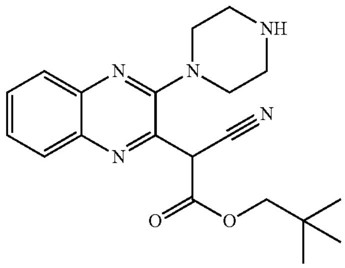 [SMILES: CC(C)(C)COC(=O)C(C#N)c1nc2ccccc2nc1N1CCNCC1] | 2,2 dimethyl propyl 2-cyano-2-(3-(4-(piperazin-1-yl)quinoxalin-2-yl)acetate | $2.10 \times 10^{-7}$ |
| 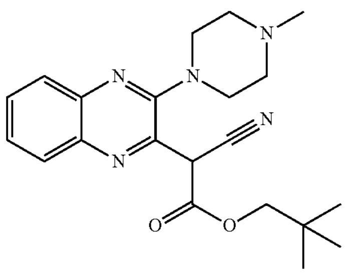 [SMILES: CN1CCN(c2nc3ccccc3nc2C(C#N)C(=O)OCC(C)(C)C)CC1] | 2,2 dimethyl propyl 2-cyano-2-(3-(4-(methylpiperazin-1-yl)quinoxalin-2-yl)acetate | $7.15 \times 10^{-7}$ |
| 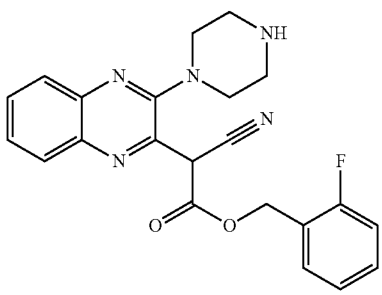 [SMILES: N#CC(C(=O)OCc1ccccc1F)c1nc2ccccc2nc1N1CCNCC1] | 2-fluorobenzyl 2-cyano-2-(3-(4-(piperazin-1-yl)quinoxalin-2-yl)acetate | $1.88 \times 10^{-6}$ |
| 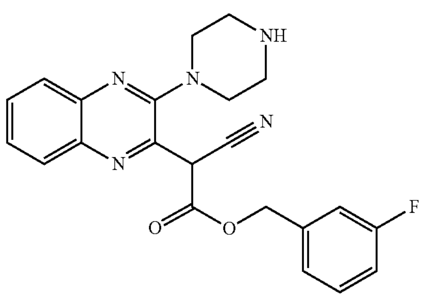 [SMILES: N#CC(C(=O)OCc1cccc(F)c1)c1nc2ccccc2nc1N1CCNCC1] | 3-fluorobenzyl 2-cyano-2-(3-(4-(piperazin-1-yl)quinoxalin-2-yl)acetate | $2.68 \times 10^{-7}$ |
| 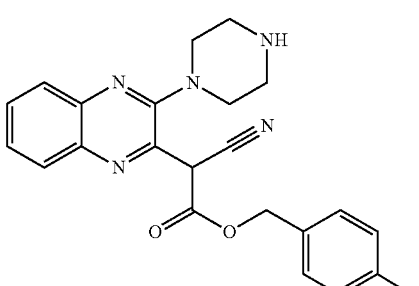 | 4-fluorobenzyl 2-cyano-2-(3-(4-(piperazin-1-yl)quinoxalin-2-yl)acetate | $1.29 \times 10^{-6}$ |

TABLE 1-continued

| Structure | Nomenclature | IC$_{50}$ (M) |
|---|---|---|
| 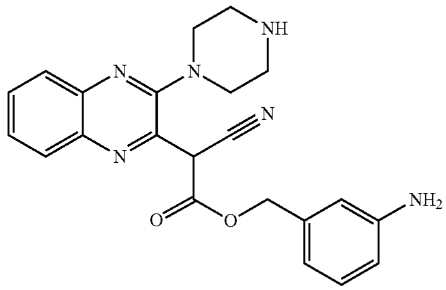 [SMILES: N#CC(C(=O)OCc1cccc(N)c1)c1nc2ccccc2nc1N1CCNCC1] | 3-aminobenzyl 2-cyano-2-(3-(4-(piperazin-1-yl)quinoxalin-2-yl)acetate | $4.13 \times 10^{-6}$ |
| 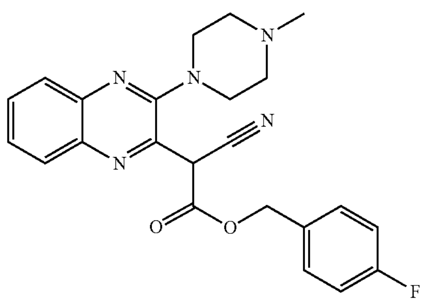 [SMILES: CN1CCN(c2nc3ccccc3nc2C(C#N)C(=O)OCc2ccc(F)cc2)CC1] | 4-fluorobenzyl 2-cyano-2-(3-(4-(methylpiperazin-1-yl)quinoxalin-2-yl)acetate | $2.89 \times 10^{-6}$ |

Example 2: Determination of CSNK1A1 Expression

Figure 4A:
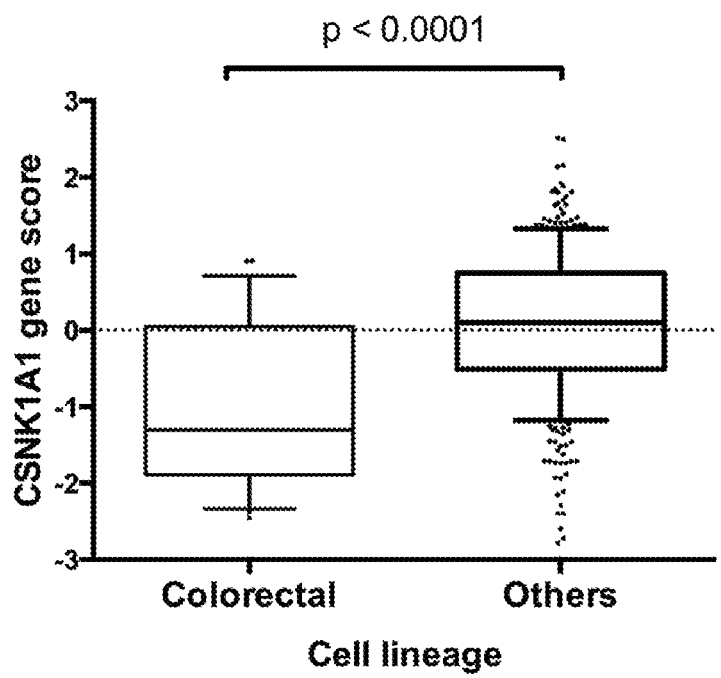
FIG. 4A illustrates the CSNK1A1 gene score of colorectal and other cell lineages.
Figure 4B:
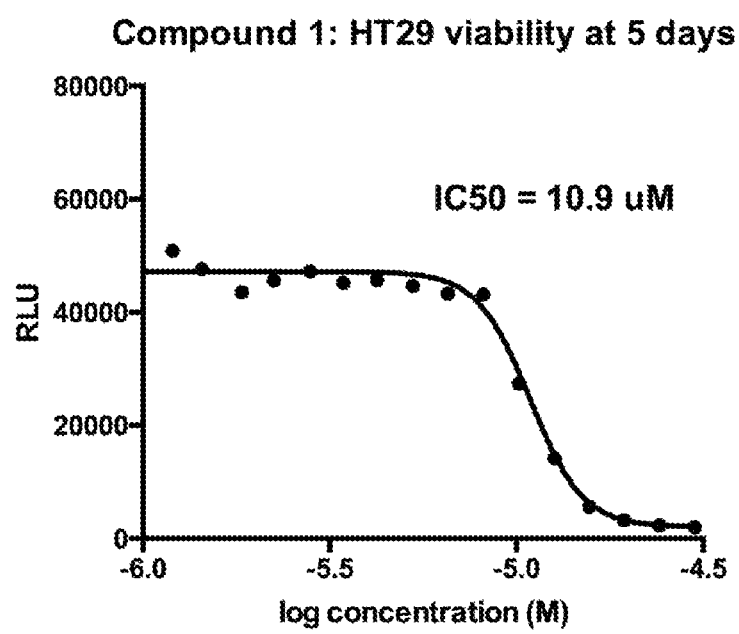
FIG. 4B comprises a graph illustrating an experimental $IC_{50}$ value for Compound 1 in HT29 cells.

In addition to its role as a target in hematologic malignancies, CSNK1A1 expression is also essential to certain epithelial cancer cell lines. Systematic knockdown of CSNK1A1 across 384 cancer cell lines using ten unique RNA interference constructs revealed increased sensitivity of colorectal cell lines versus all other lineages. Results from each independent RNA interference construct were summarized into a single gene-level score, and the colorectal distribution of sensitivities was evaluated against the other lineages by the Mann-Whitney test as shown in FIG. 4A. At least one of the colorectal cancer cell lines sensitive to CSNK1A1-knockdown, HT-29, was also inhibited by treatment with Compound 1 as shown in FIG. 4B. Cell viability was assessed by ATP abundance at 5 days using the Cell Titer Glo assay.

The results described herein above were obtained using the following methods and materials.

L1000 Gene Expression Profiling

The L1000 assay enables the detection of gene expression profiles from cell lines or RNA in high-throughput 384-well plate format. The assay couples ligation-mediated amplification using gene-specific probes and multiplex PCR with bead-based detection. This assay has been used to create a comprehensive data set containing gene expression profiles from multiple cell lines systematically treated with compounds, gene knockdown (via infection with lentiviral shRNA constructs), or gene overexpression (via infection with lentiviral cDNA constructs). This dataset is known as the "Connectivity Map." Resultant profiles are converted to differential expression signatures, which are then compared to each other by calculating an enrichment score metric (variant of the Kolmogorov-Smirnov test). The enrichment score enables matching of compound and gene perturbations for shared cellular effects.

Kinase Binding Assay

The Kinomescan assay is a site-directed small molecule competition binding assay to quantitatively measure interactions between test compounds and more than 450 kinase assays. The assay employs DNA-tagged kinase proteins and a bead-immobilized kinase ligand. Active test compounds compete with the immobilized ligand and decrease the amount of bead-bound kinase. The assay result is detected using a multiplex quantitative PCR approach.

Kinase Enzymatic Assay

Enzymatic assays were performed using a mobility shift assay on the LabChip system. Purified kinase protein was incubated with ATP, substrate, and assay buffer (20 mM Hepes—pH 7.5; 5 mM MgCl$_2$, and 0.01% Triton X-100). The assay reaction was initiated with 5 μM ATP and with each compound present. Compounds were tested at the K$_{M,ATP}$ for the protein target (GST-tagged full-length human CK1α, available from Carna Biosciences, Japan) or over a range of ATP concentrations between 5 μM and 9 μM. 1 μM Profiler Pro FL-Peptide 16 (5-FAM-KRR-RALpSVASLPGL-CONH$_2$ (SEQ ID NO: 1)) substrate was used. AC50 values were determined using phosphorylated and unphosphorylated substrates. Table 2 shows the mean AC50 values for compounds of the invention.

Cell Viability Assay

Cell viability assays were conducted against colorectal carcinoma cell line HT29. Cells were plated in wells and at 24 hours after plating, compounds were added to determine their effect on cell viability at various dosages. After 48 hours from compound administration, the cell viability was determined and the IC$_{50}$ values were calculated. Table 2 also shows the IC$_{50}$ values measured for the HT29 solid tumor cell line measured at 72 hours from plating. FIG. 4B illustrates the results of another cell viability measurement and IC$_{50}$ value for Compound 1 assessed by ATP abundance on HT29 at 5 days.

TABLE 2
| Compound | AC50 (μM) MEAN | IC50 (M) (HT29) |
|---|---|---|
| 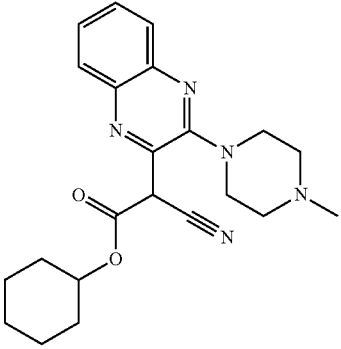 [SMILES: CN1CCN(c2nc3ccccc3nc2C(C#N)C(=O)OC2CCCCC2)CC1] | 3.498 | 1.00E−02 |
| 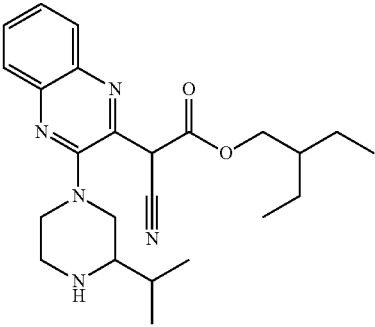 [SMILES: CCC(CC)COC(=O)C(C#N)c1nc2ccccc2nc1N1CCNC(C(C)C)C1] | 1.392 | |
| 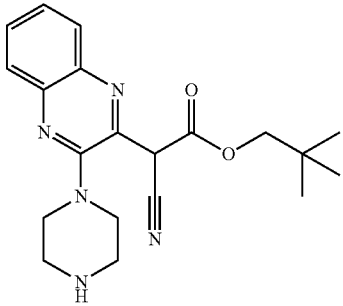 [SMILES: CC(C)(C)COC(=O)C(C#N)c1nc2ccccc2nc1N1CCNCC1] | 0.151 | |
| 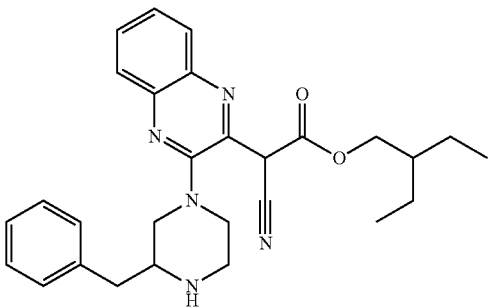 [SMILES: CCC(CC)COC(=O)C(C#N)c1nc2ccccc2nc1N1CCNC(Cc2ccccc2)C1] | 1.268 | |

TABLE 2-continued
| Compound | AC50 (μM) MEAN | IC50 (M) (HT29) |
|---|---|---|
| 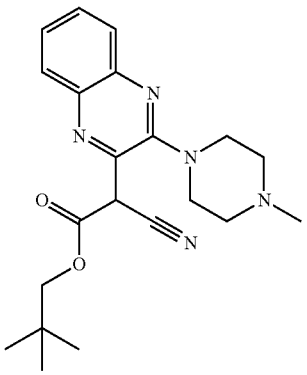 [SMILES: CN1CCN(c2nc3ccccc3nc2C(C#N)C(=O)OCC(C)(C)C)CC1] | 0.822 | |
| 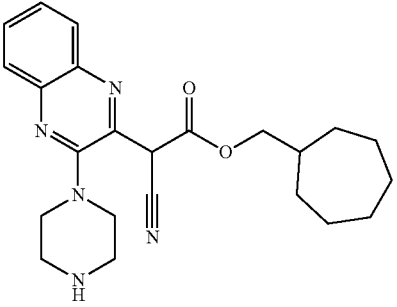 [SMILES: N#CC(C(=O)OCC1CCCCCC1)c1nc2ccccc2nc1N1CCNCC1] | 0.355 | |
| 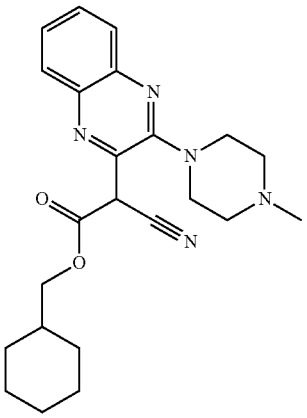 [SMILES: CN1CCN(c2nc3ccccc3nc2C(C#N)C(=O)OCC2CCCCC2)CC1] | 0.029 | |
| 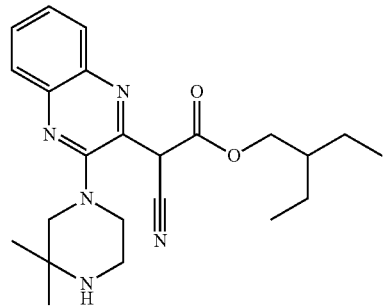 [SMILES: CCC(CC)COC(=O)C(C#N)c1nc2ccccc2nc1N1CCNC(C)(C)C1] | 0.159 | 2.13E−06 |

TABLE 2-continued

| Compound | AC50 (μM) MEAN | IC50 (M) (HT29) |
|---|---|---|
| (quinoxaline with piperidine-4-carboxamide, cyano, isobutyl ester) | 4.64 | |
| (quinoxaline with piperazine, cyano, pyridin-4-ylmethyl ester) | 0.468 | |
| (quinoxaline with piperazine, cyano, 2-fluorobenzyl ester) | 1.509 | |
| (quinoxaline with 4-(aminomethyl)piperidine, cyano, 2-ethylbutyl ester) | 2.598 | |

TABLE 2-continued
| Compound | AC50 (μM) MEAN | IC50 (M) (HT29) |
|---|---|---|
| 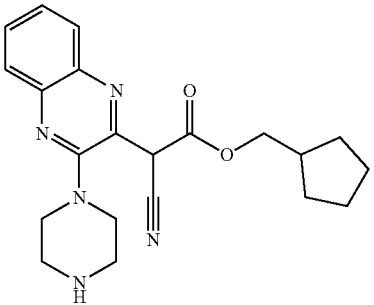 [SMILES: N#CC(C(=O)OCC1CCCC1)c1nc2ccccc2nc1N1CCNCC1] | 0.138 | |
| 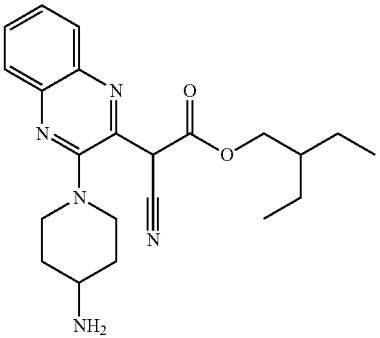 [SMILES: CCC(CC)COC(=O)C(C#N)c1nc2ccccc2nc1N1CCC(N)CC1] | 4.222 | |
| 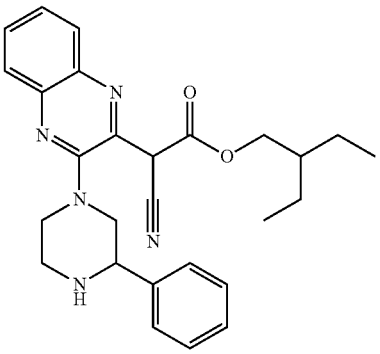 [SMILES: CCC(CC)COC(=O)C(C#N)c1nc2ccccc2nc1N1CCNC(c2ccccc2)C1] | 2.221 | |
| 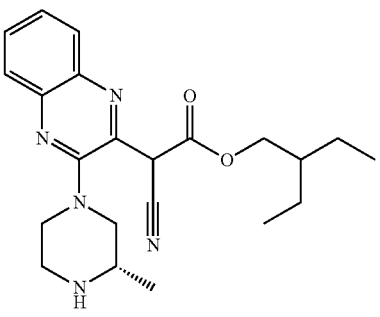 [SMILES: CCC(CC)COC(=O)C(C#N)c1nc2ccccc2nc1N1CCN[C@@H](C)C1] | 1.221 | |

TABLE 2-continued
| Compound | AC50 (μM) MEAN | IC50 (M) (HT29) |
|---|---|---|
| 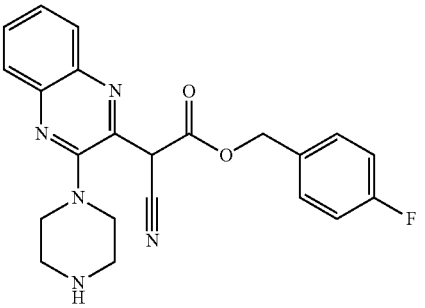 [SMILES: N#CC(C(=O)OCc1ccc(F)cc1)c1nc2ccccc2nc1N1CCNCC1] | 2.73 | |
| 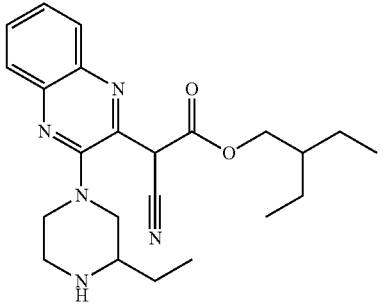 [SMILES: CCC(CC)COC(=O)C(C#N)c1nc2ccccc2nc1N1CCNC(CC)C1] | 0.958 | |
| 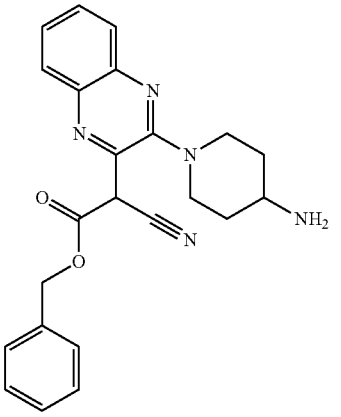 [SMILES: N#CC(C(=O)OCc1ccccc1)c1nc2ccccc2nc1N1CCC(N)CC1] | 1.82 | |
| 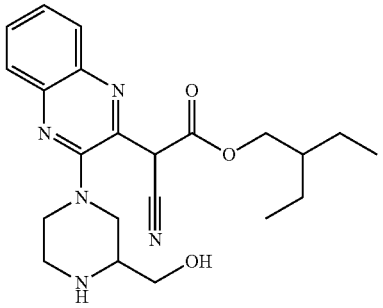 [SMILES: CCC(CC)COC(=O)C(C#N)c1nc2ccccc2nc1N1CCNC(CO)C1] | 0.517 | |

TABLE 2-continued

| Compound | AC50 (μM) MEAN | IC50 (M) (HT29) |
|---|---|---|
| (structure) | 2.791 | 5.68E−05 |
| (structure) | 0.353 | |
| (structure) | 0.304 | |
| (structure) | 3.145 | |

TABLE 2-continued
| Compound | AC50 (μM) MEAN | IC50 (M) (HT29) |
|---|---|---|
| 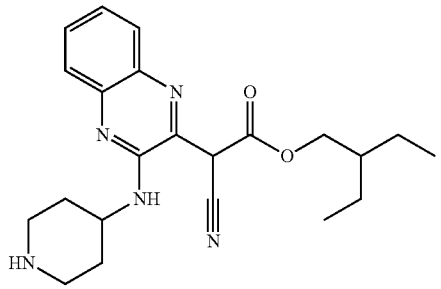 [SMILES: CCC(CC)COC(=O)C(C#N)c1nc2ccccc2nc1NC1CCNCC1] | 1.331 | |
| 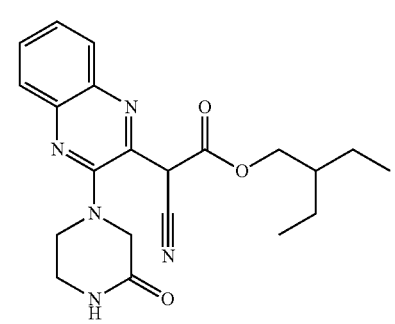 [SMILES: CCC(CC)COC(=O)C(C#N)c1nc2ccccc2nc1N1CCNC(=O)C1] | 1.741 | |
| 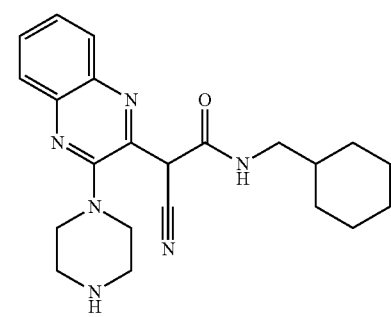 [SMILES: N#CC(C(=O)NCC1CCCCC1)c1nc2ccccc2nc1N1CCNCC1] | 1.758 | |
| 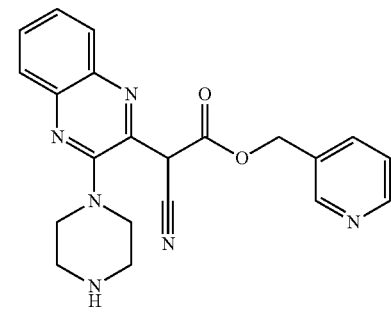 [SMILES: N#CC(C(=O)OCc1cccnc1)c1nc2ccccc2nc1N1CCNCC1] | 0.95 | |
| 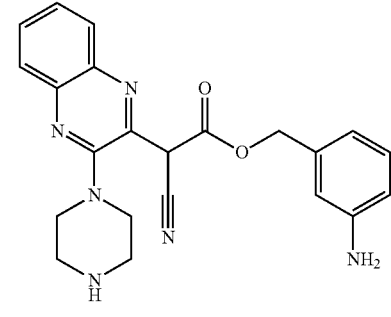 [SMILES: N#CC(C(=O)OCc1cccc(N)c1)c1nc2ccccc2nc1N1CCNCC1] | 3.805 | |

TABLE 2-continued
| Compound | AC50 (μM) MEAN | IC50 (M) (HT29) |
|---|---|---|
| 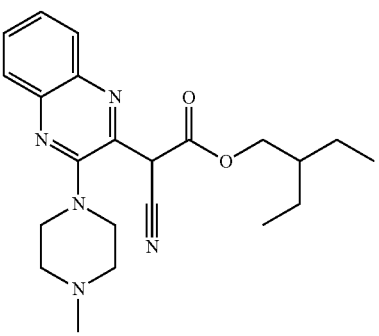 [SMILES: CCC(CC)COC(=O)C(C#N)c1nc2ccccc2nc1N1CCN(C)CC1] | 1.34 | |
| 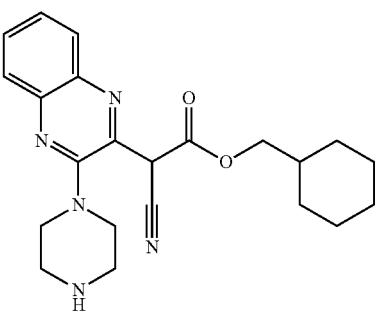 [SMILES: N#CC(C(=O)OCC1CCCCC1)c1nc2ccccc2nc1N1CCNCC1] | 0.02 | 3.78E−06 |
| 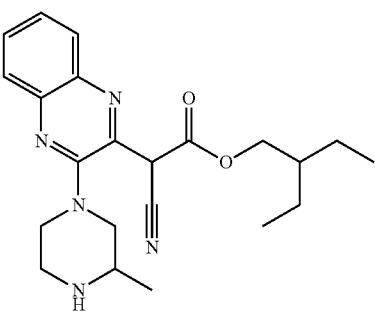 [SMILES: CCC(CC)COC(=O)C(C#N)c1nc2ccccc2nc1N1CCNC(C)C1] | 0.434 | |
| 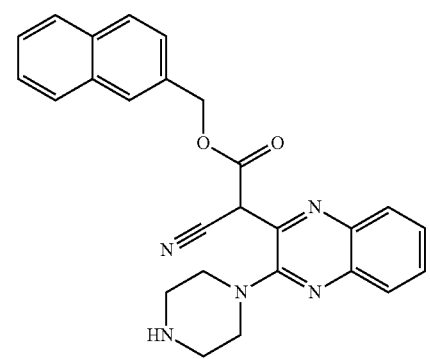 [SMILES: N#CC(C(=O)OCc1ccc2ccccc2c1)c1nc2ccccc2nc1N1CCNCC1] | 3.866 | |

TABLE 2-continued
| Compound | AC50 (μM) MEAN | IC50 (M) (HT29) |
|---|---|---|
| 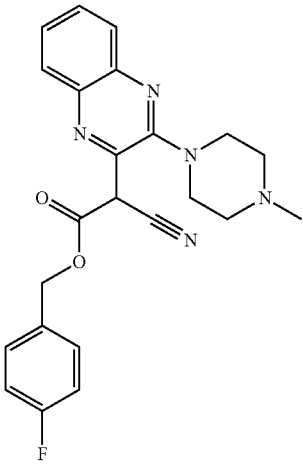 [SMILES: CN1CCN(c2nc3ccccc3nc2C(C#N)C(=O)OCc2ccc(F)cc2)CC1] | 2.041 | |
| 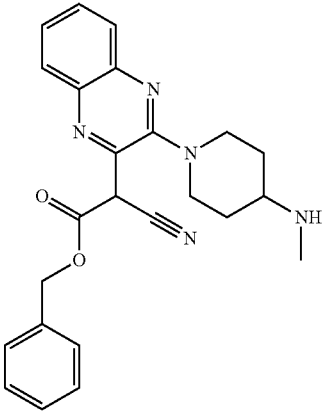 [SMILES: CNC1CCN(c2nc3ccccc3nc2C(C#N)C(=O)OCc2ccccc2)CC1] | 3.65 | |
| 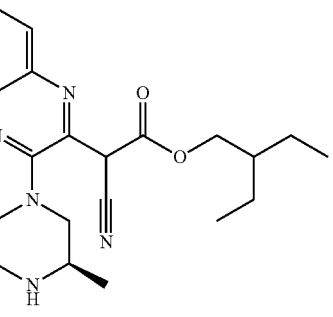 | 0.333 | |
| 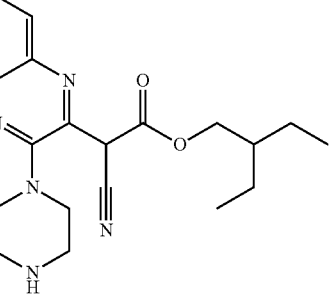 | 1.939 | |

TABLE 2-continued
| Compound | AC50 (µM) MEAN | IC50 (M) (HT29) |
|---|---|---|
| 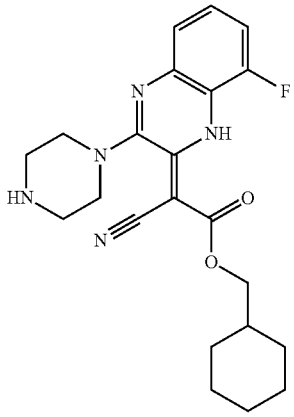 [SMILES: N#C/C(C(=O)OCC1CCCCC1)=C1/Nc2c(F)cccc2N=C1N1CCNCC1] | 1.143 | |
| 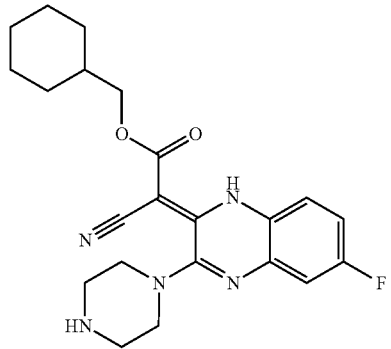 [SMILES: N#C/C(C(=O)OCC1CCCCC1)=C1/Nc2ccc(F)cc2N=C1N1CCNCC1] | 0.065 | |
| 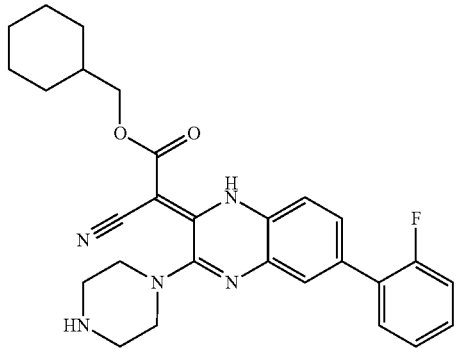 [SMILES: N#C/C(C(=O)OCC1CCCCC1)=C1/Nc2ccc(-c3ccccc3F)cc2N=C1N1CCNCC1] | 0.043 | 1.90E−06 |
| 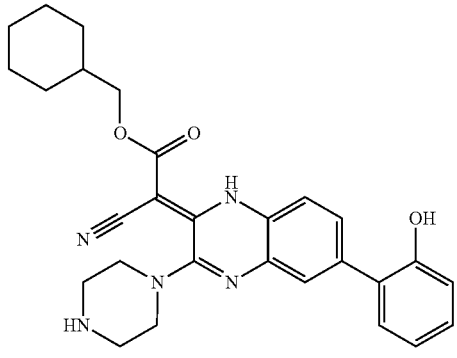 [SMILES: N#C/C(C(=O)OCC1CCCCC1)=C1/Nc2ccc(-c3ccccc3O)cc2N=C1N1CCNCC1] | 0.043 | 8.37E−07 |

TABLE 2-continued

| Compound | AC50 (μM) MEAN | IC50 (M) (HT29) |
|---|---|---|
| (structure) | 1.925 | |
| (structure) | 0.405 | |
| (structure) | 0.158 | |
| (structure) | 0.27 | |

TABLE 2-continued
| Compound | AC50 (μM) MEAN | IC50 (M) (HT29) |
|---|---|---|
| 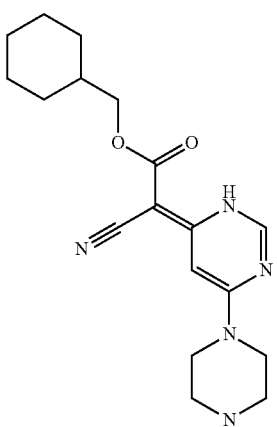 | 3.778 | |
| 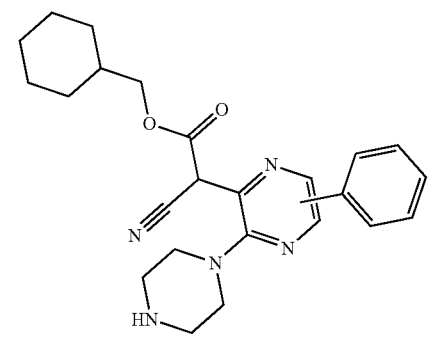 | 0.136† | |
| 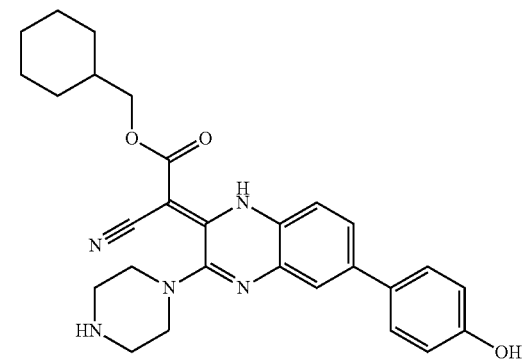 [SMILES: N#C/C(C(=O)OCC1CCCCC1)=C1/Nc2ccc(-c3ccc(O)cc3)cc2N=C1N1CCNCC1] | 0.013 | 4.72E−07 |
| 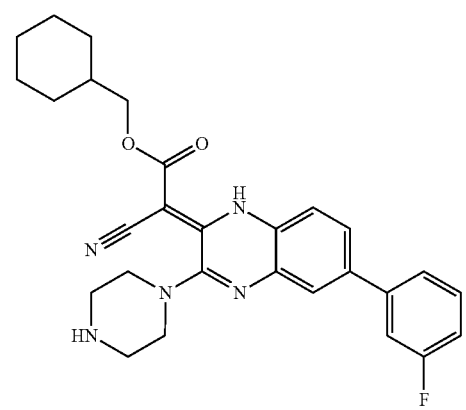 [SMILES: N#C/C(C(=O)OCC1CCCCC1)=C1/Nc2ccc(-c3cccc(F)c3)cc2N=C1N1CCNCC1] | 0.108 | 2.31E−06 |

TABLE 2-continued
| Compound | AC50 (μM) MEAN | IC50 (M) (HT29) |
|---|---|---|
| 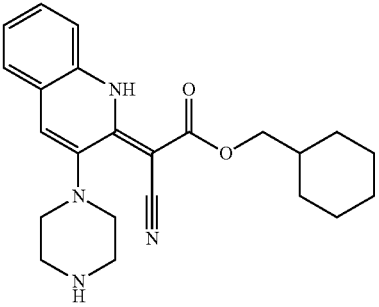 [SMILES: N#C/C(C(=O)OCC1CCCCC1)=C1/Nc2ccccc2C=C1N1CCNCC1] | 1.331 | |
| 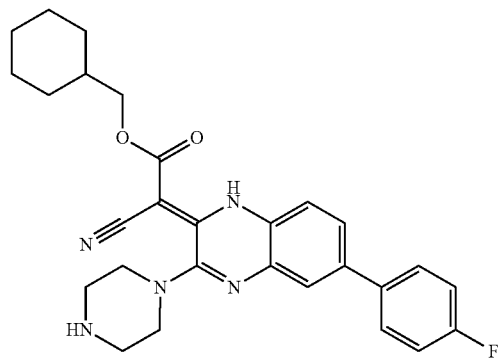 [SMILES: N#C/C(C(=O)OCC1CCCCC1)=C1/Nc2ccc(-c3ccc(F)cc3)cc2N=C1N1CCNCC1] | 0.074 | 1.78E−06 |
| 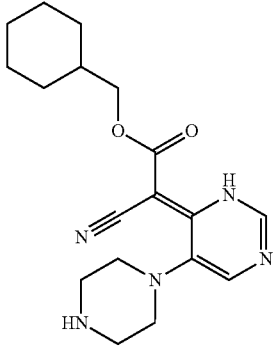 [SMILES: N#C/C(C(=O)OCC1CCCCC1)=C1/NC=NC=C1N1CCNCC1] | 0.467 | |
| 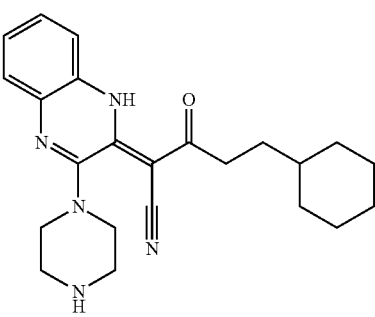 [SMILES: N#C/C(C(=O)CCC1CCCCC1)=C1/Nc2ccccc2N=C1N1CCNCC1] | 3.149 | |

TABLE 2-continued

| Compound | AC50 (μM) MEAN | IC50 (M) (HT29) |
|---|---|---|
| 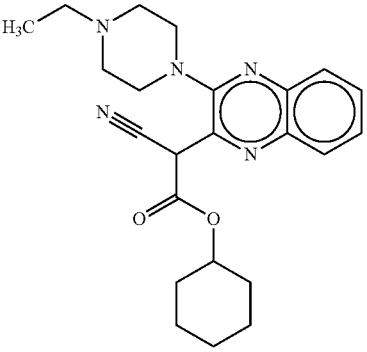 | | 1.74E−05 |
| 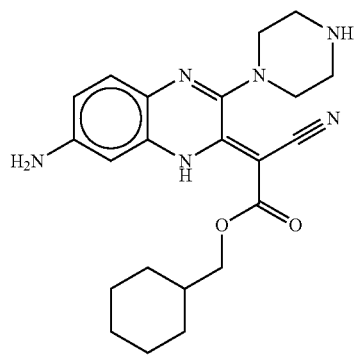 | | 3.71E−06 |
| 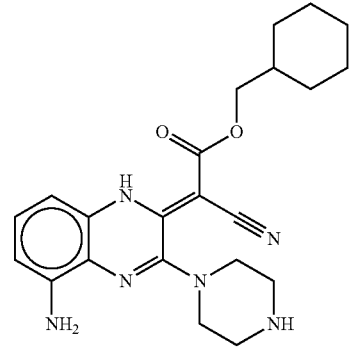 | | 5.46E−06 |

†This measured compound was synthesized and isolated as described for the synthesis of (Z)-cyclohexylmethyl 2-cyano-2-(5-phenyl-3-(piperazin-1-yl)pyrazin-2(1H)-ylidene)acetate or (Z)-cyclohexylmethyl 2-cyano-2-(6-phenyl-3-(piperazin-1-yl)pyrazin-2(1H)-ylidene)acetate. The higher yield regioisomer from that synthesis was used to measure the AC50. It will be understood that both (Z)-cyclohexylmethyl 2-cyano-2-(5-phenyl-3-(piperazin-1-yl)pyrazin-2(1H)-ylidene)acetate and (Z)-cyclohexylmethyl 2-cyano-2-(6-phenyl-3-piperazin-1-yl)pyrazin-2(1H)-ylidene)acetate are compounds having the structure of formula (I).

Example 3: Chemical Synthesis

The compounds provided herein can be prepared from readily available starting materials using the following general methods and procedures. General procedures for specific compounds described below may be used to synthesize compounds of the invention. Reactions were monitored by thin layer chromatography (TLC) with 0.25 mm E. Merck pre-coated silica gel plates (60 $F_{254}$) and Waters Alliance HT LCMS system (Waters 2998 UV/Visible Detector, Waters Acquity SQD Mass, Waters e2795 Sample Manager) using Waters Cortecs C18 column (3×30 mm, 2.7 μm particle size):solvent gradient=97% A at 0 min, 5% A at 1.75 min, 97% A at 2.28 min, total 2.60 min; solvent A=Water (MilliQ)+0.01% formic acid (Sigma); solvent B=Acetonitrile (EMD)+0.01% formic acid (Sigma); flow rate: 1.75 mL/min. Purification of reaction products was carried out by flash chromatography using CombiFlash® Rf with Teledyne Isco RediSep® Rf High Performance Gold or Silicycle SiliaSep™ High Performance columns (4 g, 12 g, 24 g, 40 g, 80 g or 120 g. 1H NMR and 13C NMR spectra were obtained using a Bruker 300 Ultrashield or Bruker 400 Ascend. Chemical shifts are reported relative to chloroform (δ=7.24) for 1H NMR or dimethyl sulfoxide (δ=2.50) for 1H NMR and dimethyl sulfoxide (δ=39.51)

General Procedure A:

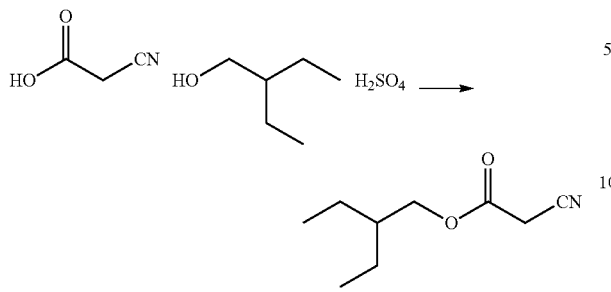

Method 1: A mixture of 2-cyanoacetic acid (4.82 g, 0.05666 mol, 1.1 eq), 2-ethylbutan-1-ol (5.26 g, 0.05150 mol, 1.0 eq) and sulfuric acid (505 mg, 0.005150 mol, 0.1 eq) in toluene (80 ml) was stirred at 80° C. overnight. The reaction was coded down, quenched with sat. $NaHCO_3$ followed by extraction with AcOEt. The combined organic layers were dried over $MgSO_4$, filtered, concentrated and purified by column chromatography on silica gel (0 to 40% AcOEt/hexanes) to furnish 2-ethylbutyl 2-cyanoacetate (4.90 g, 56% yield). NMR: 1H NMR (400 MHz, Chloroform-d) δ 4.17 (d, J=5.8 Hz, 2H), 3.47 (s, 2H), 1.59 (hept, J=6.1 Hz, 1H), 1.40 (p, J=7.4, 6.9 Hz, 4H), 0.93 (t, J=7.5 Hz, 6H).

Method 2: To a solution of 2-cyanoacetic acid (1.1 eq) in DCM (0.05 M) were added the alcohol (1.0 eq), DMAP (0.5 eq) and EDCl (1.5 eq) at room temperature. The reacting mixture was stirred overnight, then diluted in sat. $NaHCO_3$/DCM followed by extraction with DCM. The combined organic layers were washed with brine, dried over $MgSO_4$, filtered, concentrated and purified by column chromatography on silica gel.

General Procedure B:

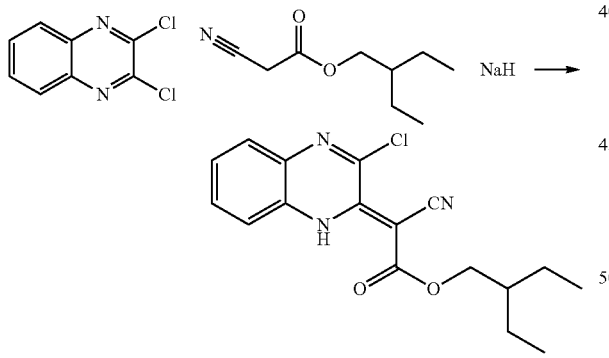

Sodium hydride (349 mg, 0.008792 mol, 1.2 eq) was added to a solution of 2-ethylbutyl 2-cyanoacetate (1.23 g, 0.007326 mol, 1.00 eq) in dry DMF (20 ml) at 0° C. under inert atmosphere. After 10 minutes, 2,3-dichloroquinoxaline (1.75 g, 0.008792 mol, 1.2 eq) was added and the reacting mixture was stirred overnight at 70° C. The solution was cooled to 0° C. then diluted in sat. $NH_4Cl$ and extracted with DCM. The combined organic layers were dried over $MgSO_4$, filtered and concentrated. Purification by column chromatography on silica gel (0 to 30% AcOEt/hexanes) provided 2-ethylbutyl 2-(3-chloroquinoxalin-2-yl)-2-cyanoacetate as a yellow solid (2.20 g, 74% yield). LCMS (m/z): 332 $[M+H]^+$.

General Procedure C:

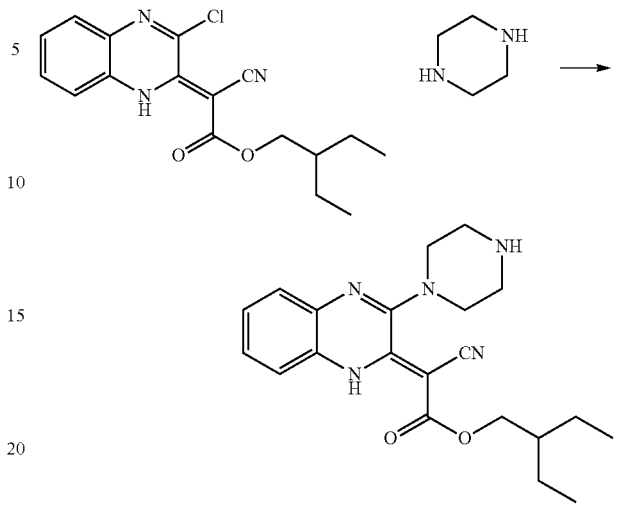

A solution of (Z)-2-ethylbutyl 2-(3-chloroquinoxalin-2 (1H)-ylidene)-2-cyanoacetate (1 eq), piperazine (3 eq) and DIPEA (3 eq) in methanol (0.1M) was stirred at 120° C. in a microwave for 90 minutes or until completion. The solution was cooled down, diluted in water/DCM followed by extraction with DCM. The combined organic layers were dried over $MgSO_4$, filtered, concentrated and purified by column chromatography on silica gel (0 to 100% AcOEt in hexanes) or by reverse phase C18 (5 to 100% $CH_3CN$ 0.1% TFA in water 0.1% TFA) to furnish (Z)-2-ethylbutyl 2-cyano-2-(3-(piperazin-1-yl)quinoxalin-2(1H)-ylidene)acetate. LCMS (m/z): 380 $[M–H]^-$. 1H NMR (400 MHz, Chloroform-d) δ 14.23 (s, 1H), 9.89 (s, 2H), 7.72 (d, J=7.9 Hz, 1H), 7.48 (t, J=7.2 Hz, 1H), 7.41 (t, J=7.7, 1H), 7.35 (d, J=8.0, 1H), 4.23 (d, J=5.7 Hz, 2H), 3.96-3.78 (m, 2H), 3.67 (m, 2H), 3.63-3.30 (m, 4H), 1.67 (m, 1H), 1.47 (p, J=7.2 Hz, 4H), 0.96 (t, J=7.4 Hz, 6H).

General Procedure D:

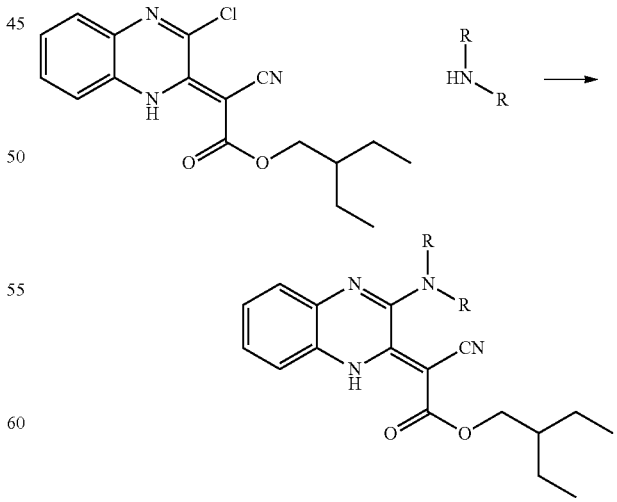

For primary amines: in a microwave vial, (Z)-2-ethylbutyl 2-(3-chloroquinoxalin-2(1H)-ylidene)-2-cyanoacetate (1 eq), the corresponding amine (2 eq), sodium tert-butoxide (2.5 eq), XPhos (0.1 eq) and XPhos Pd G3 (0.1 eq) were dissolved in degassed THF (0.1 M). The vessel was flushed with argon, sealed and heated overnight at 95° C. The reacting mixture was cooled down, then diluted in sat. NH₄Cl and extracted with AcOEt. The combined organic layers were washed with brine, dried over MgSO₄, filtered, concentrated and purified by reverse phase C18 (CH₃CN 0.1% TFA in water 0.1% TFA).

For secondary amines: in a microwave vial, (Z)-2-ethylbutyl 2-(3-chloroquinoxalin-2(1H)-ylidene)-2-cyanoacetate (1 eq), the corresponding amine (2 eq), sodium tert-butoxide (2.5 eq), BINAP (0.1 eq) and Pd₂dba₃ (0.1 eq) were dissolved in degassed THF (0.1 M). The vessel was flushed with argon, sealed and heated overnight at 95° C. The reacting mixture was cooled down, then diluted in sat. NH₄Cl and extracted with AcOEt. The combined organic layers were washed with brine, dried over MgSO₄, filtered, concentrated and purified by reverse phase C18 (CH₃CN 0.1% TFA in water 0.1% TFA).

General Procedure E:

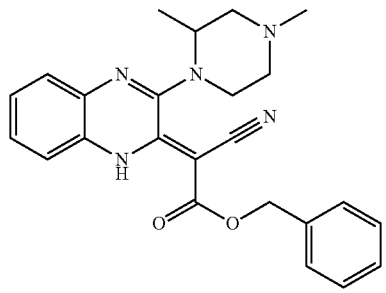 [SMILES: CC1CN(C)CCN1C1=Nc2ccccc2N/C1=C(/C#N)C(=O)OCc1ccccc1]

(Z)-benzyl 2-cyano-2-(3-(2,4-dimethylpiperazin-1-yl)quinoxalin-2(1H)-ylidene)acetate To a mixture of (Z)-benzyl 2-(3-chloroquinoxalin-2(1H)-ylidene)-2-cyanoacetate (147 mg, 437 umol) in DMSO (1.5 mL) was added 1,3-dimethylpiperazine (50 mg, 437 umol)

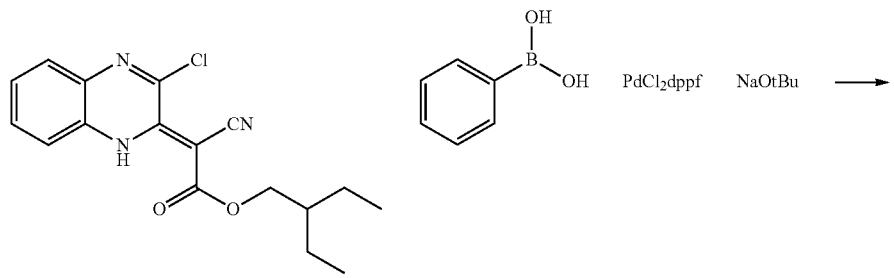

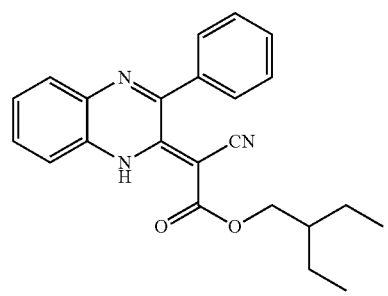

In a microwave vial, (Z)-2-ethylbutyl 2-(3-chloroquinoxalin-2(1H)-ylidene)-2-cyanoacetate (1 eq), the corresponding boronic acid or boronic ester (2 eq), sodium tert-butoxide (3 eq) and PdCl₂dppf (0.1 eq) were dissolved in degassed THF:H₂O (4:1, 0.1 M). The vessel was flushed with argon, sealed and stirred at 95° C. for 4 h or until reaction is complete. The reacting mixture was cooled down, then diluted in sat. NH₄Cl and extracted with AcOEt. The combined organic layers were washed with brine, dried over MgSO₄, filtered and purified by reverse phase C18 (CH₃CN 0.1% TFA in water 0.1% TFA).

and DIPEA (0.5 mL). The solution was treated under microwave at 110° C. for 4 hours. The reaction was diluted in water followed by extraction with AcOEt. The combined organic layers were dried over MgSO₄, filtered and concentrated. The residue was purified by column chromatography on silica gel (0 to 15% MeOH in DCM), and by prep TLC (10% MeOH in DCM) to give the desired product (Z)-benzyl 2-cyano-2-(3-(2,4-dimethylpiperazin-1-yl)quinoxalin-2(1H)-ylidene)acetate (8.5 mg, 5%). 1H NMR (400 MHz, Chloroform-d) δ 14.05 (s, 1H), 7.71 (d, J=7.7 Hz, 1H), 7.52-7.29 (m, 8H), 5.37 (s, 2H), 4.15-3.99 (m, 1H), 3.62 (s, 1H), 2.91 (s, 3H), 2.51 (s, 1H), 2.36 (s, 3H), 1.26 (d, J=15.1 Hz, 4H).

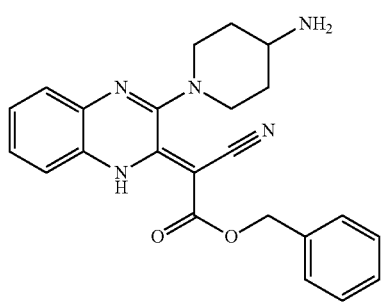 [SMILES: N#C/C(C(=O)OCc1ccccc1)=C1/Nc2ccccc2N=C1N1CCC(N)CC1]

(Z)-benzyl 2-(3-(4-aminopiperidin-1-yl)quinoxalin-2(1H)-ylidene)-2-cyanoacetate

A solution of (Z)-benzyl 2-(3-chloroquinoxalin-2(1H)-ylidene)-2-cyanoacetate (0.2 g, 592 umol), tert-butyl piperidin-4-ylcarbamate (0.177 g, 887 umol), and Et$_3$N (0.2 ml) in THF (2.5 mL) was stirred at 50° C. overnight. The reaction was diluted in water followed by extraction with AcOEt. The combined organic layers were dried over MgSO$_4$, filtered and concentrated. The residue was purified by column chromatography on silica gel (0 to 15% MeOH in DCM) to afford (Z)-benzyl 2-(3-(4-((tert-butoxycarbonyl)amino)piperidin-1-yl)quinoxalin-2(1H)-ylidene)-2-cyanoacetate (250 mg).

Boc deprotection: A solution of (Z)-benzyl 2-(3-(4-((tert-butoxycarbonyl)amino)piperidin-1-yl)quinoxalin-2(1H)-ylidene)-2-cyanoacetate was stirred in 10% TFA in DCM (5 ml) at room temperature until completion. The reaction was concentrated under vacuum and the excess TFA was azeotroped with toluene (3×) to provide (Z)-benzyl 2-(3-(4-aminopiperidin-1-yl)quinoxalin-2(1H)-ylidene)-2-cyanoacetate. TFA salt isolated. LCMS (m/z): 400 [M−H]$^-$.

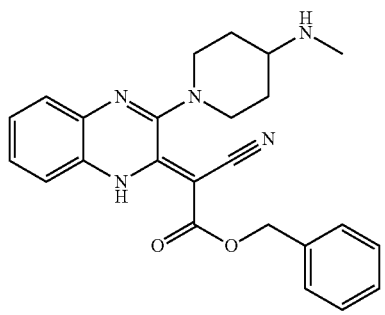 [SMILES: CNC1CCN(C2=Nc3ccccc3N/C2=C(/C#N)C(=O)OCc2ccccc2)CC1]

(Z)-benzyl 2-cyano-2-(3-(4-(methylamino)piperidin-1-yl)quinoxalin-2(1H)-ylidene)acetate To a mixture of (Z)-benzyl 2-(3-chloroquinoxalin-2(1H)-ylidene)-2-cyanoacetate (0.3 g, 888 umol), tert-butyl methyl (piperidin-4-yl)carbamate (0.28 g, 1.33 mmol) in THF (1.5 mL) was added Et$_3$N (0.17 g, 1.77 mol). The reaction was stirred overnight at 50° C., then diluted in water and extracted with AcOEt. The combined organic layers were dried over MgSO$_4$, filtered and concentrated. The residue was purified by column chromatography on silica gel (0 to 15% MeOH in DCM) to afford (Z)-benzyl 2-(3-(4-((tert-butoxycarbonyl)(methyl)amino)piperidin-1-yl)quinoxalin-2(1H)-ylidene)-2-cyanoacetate (333 mg, 72% yield).

Boc deprotection: A solution of (Z)-benzyl 2-(3-(4-((tert-butoxycarbonyl)(methyl)amino)piperidin-1-yl)quinoxalin-2(1H)-ylidene)-2-cyanoacetate (40 mg, 77.5 umol) was stirred in 10% TFA in DCM (5 ml) at room temperature until completion. The reaction was concentrated under vacuum and the excess TFA was azeotroped with toluene (3×) to provide (Z)-benzyl 2-cyano-2-(3-(4-(methylamino)piperidin-1-yl)quinoxalin-2(1H)-ylidene)acetate (33 mg). TFA salt isolated. LCMS (m/z): 416 [M+H]$^+$.

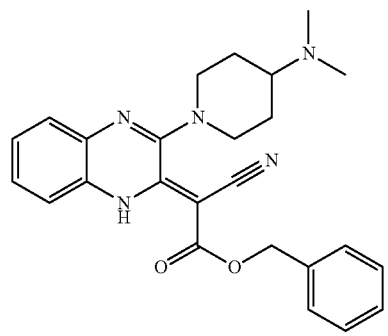 [SMILES: CN(C)C1CCN(C2=Nc3ccccc3N/C2=C(/C#N)C(=O)OCc2ccccc2)CC1]

(Z)-benzyl 2-cyano-2-(3-(4-(dimethylamino)Piperidin-1-yl)quinoxalin-2(1H)-ylidene)acetate Prepared following general procedure C using N,N-dimethylpiperidin-4-amine. LCMS (m/z): 430 [M+H]$^+$.

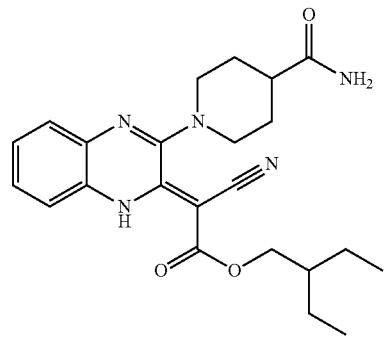 [SMILES: CCC(CC)COC(=O)/C(C#N)=C1\Nc2ccccc2N=C1N1CCC(C(N)=O)CC1]

(Z)-2-ethylbutyl 2-(3-(4-carbamoylpiperidin-1-yl)quinoxalin-2(1H)-ylidene)-2-cyanoacetate Prepared following general procedure C using piperidine-4-carboxamide. LCMS (m/z): 396 [M+H]$^+$.

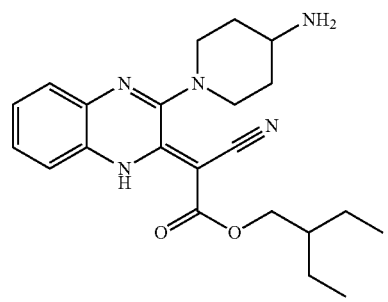 [SMILES: CCC(CC)COC(=O)/C(C#N)=C1\Nc2ccccc2N=C1N1CCC(N)CC1]

(Z)-2-ethylbutyl 2-(3-(4-aminopiperidin-1-yl)quinoxalin-2(1H)-ylidene)-2-cyanoacetate Prepared following general procedure C using tert-butyl piperidin-4-ylcarbamate. Boc deprotection: the purified adduct was stirred in 5% TFA in DCM overnight. The mixture was concentrated, diluted in DCM and washed with sat. NaHCO$_3$ (3×), water and brine. The organic layer was dried over MgSO$_4$, filtered concentrated and purified by reverse phase C18 (CH$_3$CN 0.1% TFA in water 0.1% TFA). TFA salt isolated. LCMS (m/z): 394 [M–H]$^-$. 1H NMR (400 MHz, Methanol-d4) δ 7.66 (d, J=7.1 Hz, 1H), 7.56-7.36 (m, 3H), 4.24 (d, J=5.5 Hz, 2H), 3.88 (m, 2H), 3.03 (br, 3H), 1.97 (br, 4H), 1.63 (p, J=6.1 Hz, 1H), 1.49 (p, J=7.5 Hz, 4H), 0.98 (t, J=7.5 Hz, 6H).

(Z)-2-ethylbutyl 2-cyano-2-(3-(3-methylpiperazin-1-yl)quinoxalin-2(1H)-ylidene)

Prepared following general procedure C using tert-butyl 2-methylpiperazine-1-carboxylate. Boc deprotection: the purified adduct was stirred in 5% TFA in DCM overnight. The mixture was then concentrated, diluted in DCM and washed with sat. NaHCO$_3$ (3×), water and brine. The organic layer was dried over MgSO$_4$, filtered, concentrated and purified by reverse phase (CH$_3$CN 0.1% TFA in water 0.1% TFA). TFA salt isolated. 1H NMR (400 MHz, Methanol-d4) δ 7.66 (d, J=7.1 Hz, 1H), 7.56-7.36 (m, 3H), 4.24 (d, J=5.5 Hz, 2H), 3.94-3.69 (br, 4H), 3.58 (br, 1H), 3.21-2.87 (s, 2H), 1.63 (p, J=6.1 Hz, 1H), 1.49 (p, J=7.5 Hz, 4H), 0.98 (t, J=7.5 Hz, 6H). LCMS (m/z): 394 [M–H]$^-$.

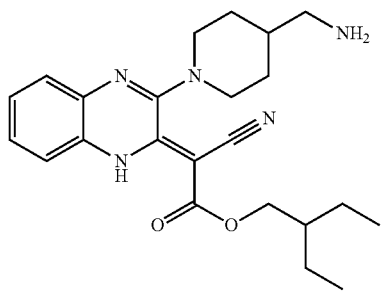 [SMILES: CCC(CC)COC(=O)/C(C#N)=C1\Nc2ccccc2N=C1N1CCC(CN)CC1]

(Z)-2-ethylbutyl 2-(3-(4-(aminomethyl)piperidin-1-yl)quinoxalin-2(1H)-ylidene)-2-cyanoacetate Prepared following general procedure C using benzyl (piperidin-4-ylmethyl)carbamate. Cbz deprotection: the purified adduct was dissolved in MeOH and degassed for 10 minutes with Argon. Pd/C (5%) was then added and the reacting mixture was stirred under hydrogen atmosphere for 5 h. The solution was then degassed for 15 minutes with argon, filtered over celite, concentrated and purified by reverse phase (CH$_3$CN 0.1% TFA in water 0.1% TFA). TFA salt isolated. 1H NMR (400 MHz, DMSO-d6) δ 13.78 (s, 1H), 7.78 (br, 2H), 7.72 (d, J==8.1 Hz, 1H), 7.62 (br, 1H), 7.43 (br, 2H), 4.17 (d, J=5.7 Hz, 2H), 3.92-3.57 (m, 2H), 2.72 (d, J=27.3 Hz, 4H), 1.80 (m, 5H), 1.59 (p, J=6.1 Hz, 1H), 1.39 (p, J=7.1 Hz, 4H), 0.91 (t J=7.4 Hz, 6H). LCMS (m/z): 408 [M–H]$^-$.

(Z)-2-ethylbutyl 2-cyano-2-(3-(3-oxopiperazin-1-yl)quinoxalin-2(1H)-ylidene)acetate Prepared following general procedure C using piperazin-2-one. 1H NMR (400 MHz, Chloroform-d) δ 14.15 (s, 1H), 7.70 (d, J=7.8 Hz, 1H), 7.54-7.38 (m, 2H), 7.35 (d, J=8.0 Hz, 1H), 6.94 (s, 1H), 4.23 (d, J=5.7 Hz, 2H), 4.16 (s, 2H), 3.94-3.33 (m, 4H), 1.68 (p, J=6.2 Hz, 1H), 1.48 (p, J=7.0 Hz, 4H), 0.96 (t, J=7.5 Hz, 6H). LCMS (m/z): 394 [M–H]$^-$.

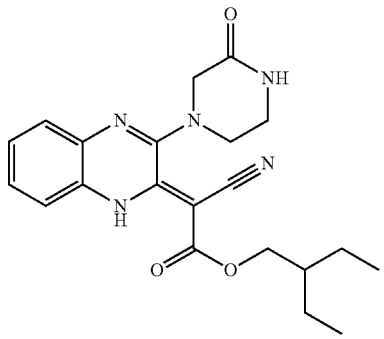

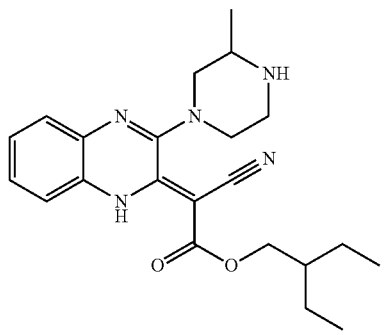 [SMILES: CCC(CC)COC(=O)/C(C#N)=C1\Nc2ccccc2N=C1N1CCNC(C)C1]

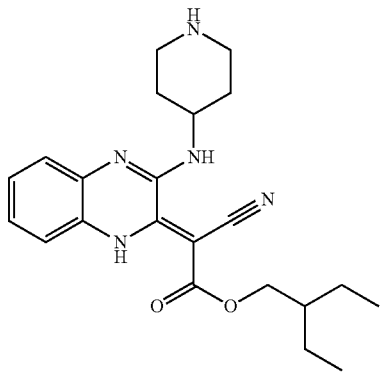 [SMILES: CCC(CC)COC(=O)/C(C#N)=C1\Nc2ccccc2N=C1NC1CCNCC1]

(Z)-2-ethylbutyl 2-cyano-2-(3-(piperidin-4-ylamino)quinoxalin-2(1H)-ylidene)acetate Prepared following general procedure C using piperidin-4-amine. LCMS (m/z): 394 [M–H]$^-$.

117

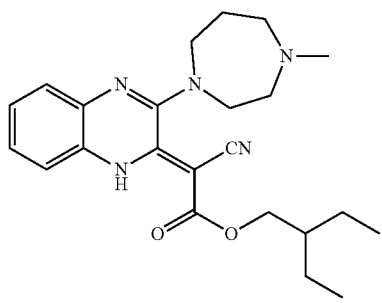 [SMILES: CCC(CC)COC(=O)/C(C#N)=C1\Nc2ccccc2N=C1N1CCCN(C)CC1]

(Z)-2-ethylbutyl 2-cyano-2-(3-(4-methyl-1,4-diazepan-1-yl)quinoxalin-2(1H)-ylidene)acetate Prepared following general procedure D using 1-methyl-1,4-diazepane. 1H NMR (400 MHz, Chloroform-d) δ 14.14 (s, 1H), 7.69 (d, J=7.9 Hz, 1H), 7.50 (t, J=7.0 Hz, 1H), 7.47-7.39 (t, J=7.9 Hz, 1H), 7.36 (d, J=8.0 Hz, 1H), 4.31-4.01 (m, 4H), 3.97-3.63 (m, 4H), 3.48 (m, 1H), 3.30-3.07 (m, 1H), 2.92 (s, 3H), 2.43 (brs, 2H), 1.67 (m, 1H), 1.48 (p, J=6.4, 5.7 Hz, 4H), 0.97 (t, J=7.4 Hz, 6H). LCMS (m/z): 408 [M−H]⁻.

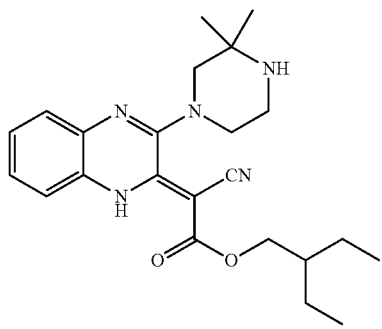 [SMILES: CCC(CC)COC(=O)/C(C#N)=C1\Nc2ccccc2N=C1N1CCNC(C)(C)C1]

(Z)-2-ethylbutyl 2-cyano-2-(3-(3,3-dimethylpiperazin-1-yl)quinoxalin-2(1H)-ylidene)acetate Prepared following general procedure C using tert-butyl 2,2-dimethylpiperazine-1-carboxylate. Boc deprotection: The purified intermediate was stirred in 5% TFA in DCM overnight. The solvent was evaporated and the excess TFA was azeotroped with toluene (3×). TFA salt isolated. LCMS (m/z): 408 [M−H]⁻. 1H NMR. (400 MHz, Chloroform-d) δ 14.28 (s, 1H), 9.61 (s, 2H), 7.72 (d, J=7.7 Hz, 1H), 7.49 (t, J=8.3 Hz, 1H), 7.43 (t, J=8.3 Hz, 1H), 7.36 (d, J=7.9 Hz, 1H), 4.29-4.18 (m, 3H), 3.92-3.81 (br, 1H), 3.54-3.47 (br, 2H), 3.36-3.23 (br, 1H), 3.11-2.97 (s, 1H), 1.78-1.54 (m, 7H), 1.49 (p, J=7.1 Hz, 4H), 0.97 (t, J=7.4 Hz, 6H).

118

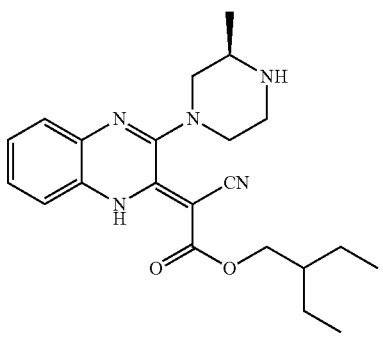 [SMILES: CCC(CC)COC(=O)/C(C#N)=C1\Nc2ccccc2N=C1N1CCN[C@H](C)C1]

(R,Z)-2-ethylbutyl 2-cyano-2-(3-(3-methylpiperazin-1-yl)quinoxalin-2(1H)-ylidene)acetate Prepared following general procedure C using (R)-tert-butyl 2-methylpiperazine-1-carboxylate. Boc deprotection: The purified intermediate was stirred in 5% TFA in DCM overnight. The solvent was evaporated and the excess TFA was azeotroped with toluene (3×). TFA salt isolated. LCMS (m/z): 394 [M−H]⁻. 1H NMR (400 MHz, Chloroform-d) δ 14.25 (s, 1H), 9.85 (s, 1H), 9.58 (s, 1H), 7.73 (d, J=6.6 Hz, 1H), 7.49 (t, J=7.4 Hz, 1H), 7.42 (t, J=7.2 Hz, 1H), 7.35 (d, J=7.9 Hz, 1H), 4.23 (d, J=7.7 Hz, 2H), 3.97-3.72 (m, 4H), 3.54-3.45 (m, 1H), 3.37-3.27 (m, 1H), 3.10-3.09 (m, 1H), 1.68 (p, 6.2 Hz, 1H), 1.48 (m, 7H), 0.96 (t, J=7.4 Hz, 6H).

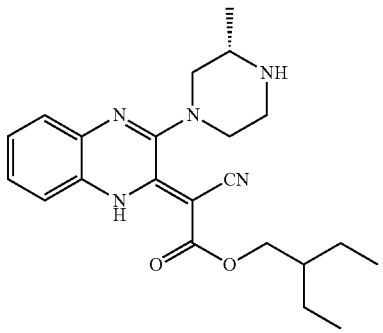 [SMILES: CCC(CC)COC(=O)/C(C#N)=C1\Nc2ccccc2N=C1N1CCN[C@@H](C)C1]

(S,Z)-2-ethylbutyl 2-cyano-2-(3-(3-methylpiperazin-1-yl)quinoxalin-2(1H)-ylidene)acetate Prepared following general procedure C using (S)-tert-butyl 2-methylpiperazine-1-carboxylate. Boc deprotection: The purified intermediate was stirred in 5% TFA in DCM overnight. The solvent was evaporated and the excess TFA was azeotroped with toluene (3×). TFA salt isolated. LCMS (m/z): 394 [M−H]⁻. 1H NMR (400 MHz, Chloroform-d) δ 14.25 (s, 1H), 10.05 (s, 1H), 9.52 (s, 1H), 7.73 (d, J=6.9 Hz, 1H), 7.49 (t, J=7.4 Hz, 1H), 7.42 (t, J=7.5 Hz, 1H), 7.35 (d, J=7.9 Hz, 1H), 4.23 (d, J=7.8 Hz, 2H), 4.01-3.69 (m, 4H), 3.59-3.44 (m, 1H), 3.39-3.25 (s, 1H), 3.21-3.04 (m, 1H), 1.68 (p, 6.2 Hz, 1H), 1.48 (m, 7H), 0.96 (t, J=7.5 Hz, 6H).

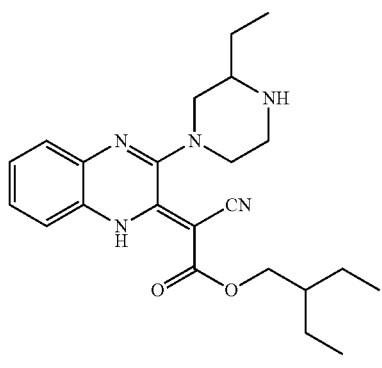 [SMILES: CCC(CC)COC(=O)/C(C#N)=C1\Nc2ccccc2N=C1N1CCNC(CC)C1]

(Z)-2-ethylbutyl 2-cyano-2-(3-(3-ethylpiperazin-1-yl)quinoxalin-2(1H)-ylidene)acetate Prepared following general procedure C using tert-butyl 2-ethylpiperazine-1-carboxylate. Boc deprotection: The purified intermediate was stirred in 5% TFA in DCM overnight. The solvent was evaporated and the excess TFA was azeotroped with toluene (3×). TFA salt isolated. LCMS (m/z): 408 [M−H]⁻. 1H NMR (400 MHz, Chloroform-d) δ 14.26 (s, 1H), 9.85 (s, 1H), 9.56 (s, 1H), 7.74 (d, J=6.9 Hz, 1H), 7.49 (t, J=7.4 Hz, 1H), 7.43 (t, J=7.2 Hz, 1H), 7.36 (d, J=8.0 Hz, 1H), 4.24 (d, J=5.8 Hz, 2H), 3.90-3.711 (m, 4H), 3.55-3.46 (m, 1H), 3.38-3.28 (m, 1H), 3.17-3.05 (m, 1H), 1.63-1.97 (m, 3H), 1.48 (p, J=7.2 Hz, 4H), 1.24-1.05 (br, 3H), 0.96 (t, J=7.4 Hz, 6H).

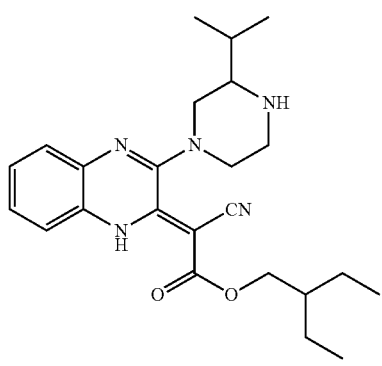 [SMILES: CCC(CC)COC(=O)/C(C#N)=C1\Nc2ccccc2N=C1N1CCNC(C(C)C)C1]

(Z)-2-ethylbutyl 2-cyano-2-(3-(3-isopropylpiperazin-1-yl)quinoxalin-2(1H)-ylidene)acetate Prepared following general procedure C using tert-butyl 2-isopropylpiperazine-1-carboxylate. Boc deprotection: The purified intermediate was stirred in 5% TFA in DCM overnight. The solvent was evaporated and the excess TFA was azeotroped with toluene (3×), TFA salt isolated. LCMS (m/z): 422 [M−H]⁻. 1H NMR (400 MHz, Chloroform-d) δ 14.26 (s, 1H), 9.67 (s, 1H), 9.55 (s, 1H), 7.74 (d, J=7.8 Hz, 1H), 7.49 (t, J=7.3 Hz, 1H), 7.43 (t, J=7.4 Hz, 1H), 7.36 (d, J=7.8 Hz, 1H), 4.24 (d, J=5.4 Hz, 2H), 3.83 (m, 2H), 3.66 (br, 1H) 3.53 (d, J=11.9 Hz, 1H), 3.44-3.25 (m, 1H), 3.24-3.05 (m, 1H), 2.13 (br, 1H), 1.68 (p, J=6.2 Hz, 1H), 1.47 (p, J=6.9 Hz, 4H), 1.18 (d, J=6.7 Hz, 2H), 1.14 (d, J=6.6 Hz, 2H), 0.96 (t, J=7.4 Hz, 6H).

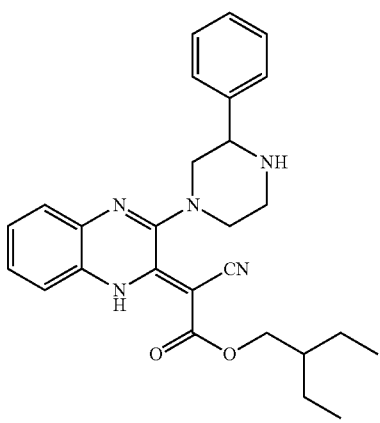 [SMILES: CCC(CC)COC(=O)/C(C#N)=C1\Nc2ccccc2N=C1N1CCNC(c2ccccc2)C1]

(Z)-2-ethylbutyl 2-cyano-2-(3-(3-phenylpiperazin-1-yl)quinoxalin-2(1H)-ylidene)

Prepared following general procedure C using tert-butyl 2-phenylpiperazine-1-carboxylate. Boc deprotection: The purified intermediate was stirred in 5% TFA in DCM overnight. The solvent was evaporated and the excess TFA was azeotroped with toluene (3×). TFA salt isolated. LCMS (m/z): 456 [M−H]⁻. 1H NMR (400 MHz, Chloroform-d) δ 14.26 (s, 1H), 10.06 (s, 2H), 7.71 (d, J=7.9 Hz, 1H), 7.57 (br, 1H), 7.52-7.45 (m, 1H), 7.42 (m, 4H), 7.35 (d, J=8.7 Hz, 1H), 4.86 (d, J=11.1 Hz, 1H), 4.21 (m, 2H), 3.86 (d, J=12.7 Hz, 1H), 3.72 (m, 1H), 3.53 (t, J=12.0 Hz, 1H), 3.40 (m, 1H), 3.14 (d, J=11.8 Hz, 1H), 1.77-1.57 (m, 1H), 1.48 (p, J=7.2 Hz, 4H), 0.97 (t, J=7.4 Hz, 6H).

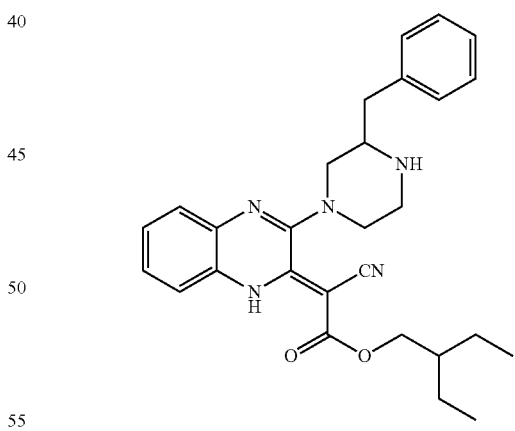

(Z)-2-ethylbutyl 2-(3-(3-benzylpiperazin-1-yl)quinoxalin-2(1H)-ylidene)-2-cyanoacetate Prepared following general procedure C using tert-butyl 2-benzylpiperazine-1-carboxylate. Boc deprotection: The purified intermediate was stirred in 5% TFA in DCM overnight. The solvent was evaporated and the excess TFA was azeotroped with toluene (3×). TFA salt isolated. LCMS (m/z): 470 [M−H]⁻.

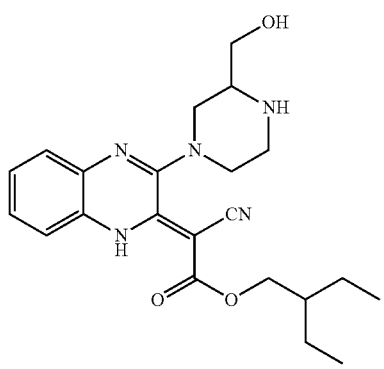 [SMILES: CCC(CC)COC(=O)/C(C#N)=C1\Nc2ccccc2N=C1N1CCNC(CO)C1]

(Z)-2-ethylbutyl 2-cyano-2-(3-(3-(hydroxymethyl)piperazin-1-yl)quinoxalin-2(1H)-ylidene)acetate Prepared following general procedure C using tert-butyl 2-(hydroxymethyl)piperazine-1-carboxylate. Boc deprotection: The purified intermediate was stirred in 5% TFA in DCM overnight. The solvent was evaporated and the excess TFA was azeotroped with toluene (3×). TFA salt isolated. LCMS (m/z): 410 [M−H]−. 1H NMR (400 MHz, Chloroform-d) δ 14.18 (s, 1H), 9.54 (brs, 2H), 7.73 (d, J=7.5 Hz, 1H), 7.49 (t, J=7.4 Hz, 1H), 7.42 (t, J=7.4 Hz, 1H), 7.35 (d, J=7.9 Hz, 1H), 4.23 (d, J=5.6 Hz, 2H), 4.16-3.94 (m, 2H), 3.92-3.68 (m, 5H), 3.64-3.54 (m, 1H), 3.49-3.20 (m, 2H), 1.67 (p, J=6.1 Hz, 1H), 1.47 (p, J=7.2 Hz, 4H), 0.96 (t, J=7.4 Hz, 6H).

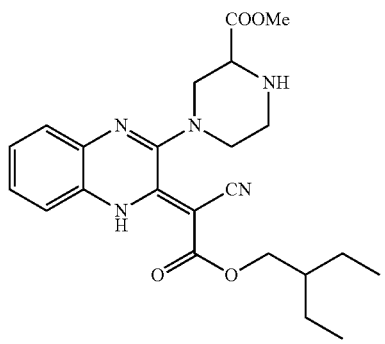 [SMILES: CCC(CC)COC(=O)/C(C#N)=C1\Nc2ccccc2N=C1N1CCNC(C(=O)OC)C1]

(Z)-methyl 4-(3-(1-cyano-2-(2-ethylbutoxy)-2-oxoethylidene)-3,4-dihydroquinoxalin-2-yl)piperazine-2-carboxylate Prepared following general procedure C using 1-tert-butyl 2-methylpiperazine-1,2-dicarboxylate. Boc deprotection: The purified intermediate was stirred in 5% TFA in DCM overnight. The solvent was evaporated and the excess TFA was azeotroped with toluene (3×). Converted to the free base and purified by column chromatography (0 to 15% MeOH in DCM). LCMS (m/z): 438 [M−H]−. 1H NMR (400 MHz, Chloroform-d) δ 14.26 (s, 1H), 7.74 (d, J=7.9 Hz, 1H), 7.51 (t, J=7.2 Hz, 1H), 7.43 (t, J=8.2 Hz, 1H), 7.36 (d, J=7.9 Hz, 1H), 4.57-4.74 (br, 1H), 4.00-4.26 (m, 4H), 3.94-3.70 (m, J=14.9 Hz, 6H), 3.55-3.41 m, 2H), 1.68 (m, 1H), 1.48 (p, J=7.1 Hz, 4H), 0.97 (t, J=7.4 Hz, 6H).

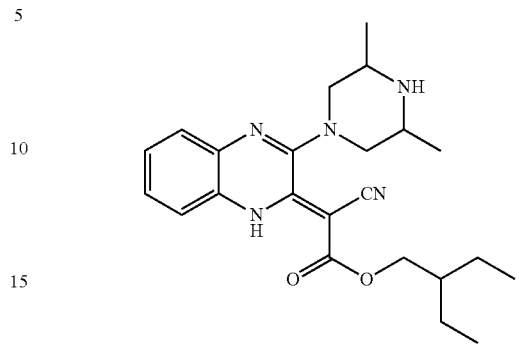

(Z)-2-ethylbutyl 2-cyano-2-(3-(3,5-dimethylpiperazin-1-yl)quinoxalin-2(1H)-ylidene)

Prepared following general procedure C using tert-butyl 2,6-dimethylpiperazine-1-carboxylate. Boc deprotection: The purified intermediate was stirred in 5% TFA in DCM overnight. The solvent was evaporated and the excess TFA was azeotroped with toluene (3×). TFA salt isolated. LCMS (m/z): 408 [M−H]−. 1H NMR (400 MHz, Chloroform-d) δ 14.25 (s, 1H), 10.14 (s, 1H), 9.31 (s, 1H), 7.73 (br, 1H), 7.48 (t, J=7.3 Hz, 1H), 7.42 (t, J=7.1 Hz, 1H), 7.35 (d, J=7.8 Hz, 1H), 4.23 (d, J=5.8 Hz, 2H), 4.10-3.86 (m, 2H), 3.86-3.66 (m, 2H), 3.22-3.08 (m, 2H), 1.68 (p, 6.2 Hz, 1H), 1.51-1.38 (m, 10H), 0.96 (t, J=7.4 Hz, 6H).

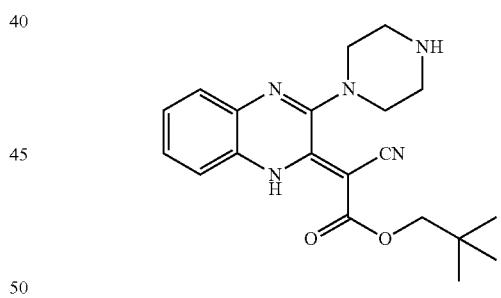

(Z)-neopentyl 2-cyano-2-(3-(piperazin-1-yl)quinoxalin-2(1H)-ylidene)acetate neopentyl 2-cyanoacetate was prepared following general procedure A. (Z)-neopentyl 2-(3-chloroquinoxalin-2(1H)-ylidene)-2-cyanoacetate was prepared following general procedure B. (Z)-neopentyl 2-cyano-2-(3-(piperazin-1-yl)quinoxalin-2(1H)-ylidene)acetate was prepared following general procedure C. TFA salt. LCMS (m/z): 368 [M+H]+. 1H NMR (400 MHz, Methanol-d4) δ 7.74 (d, J=8.0 Hz, 1H), 7.56 (m, 2H), 7.47 (m, 1H), 4.00 (s, 2H), 3.84 (m, 2H), 3.69-3.46 (m, 4H), 3.35 (m, 2H), 1.06 (s, 9H).

123

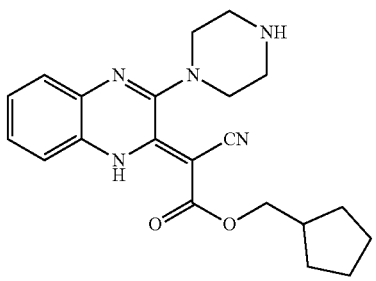 [SMILES: N#C/C(C(=O)OCC1CCCC1)=C1/Nc2ccccc2N=C1N1CCNCC1]

(Z)-cyclopentylmethyl 2-cyano-2-(3-(piperazin-1-yl)
quinoxalin-2(1H)-ylidene)

cyclopentylmethyl 2-cyanoacetate was prepared following general procedure A. (Z)-cyclopentylmethyl 2-(3-chloroquinoxalin-2(1H)-ylidene)-2-cyanoacetate was prepared following general procedure B. (Z)-cyclopentylmethyl 2-cyano-2-(3-(piperazin-1-yl)quinoxalin-2(1H)-ylidene)acetate was prepared following general procedure C. TFA salt isolated. LCMS (m/z): 378 [M–H]⁻. 1H NMR (400 MHz, Chloroform-d) δ 14.25 (s, 1H) 9.85 (brs, 2H), 7.73 (d, J=7.8 Hz, 1H), 7.49 (t, J=7.7 Hz, 1H), 7.43 (t, J=7.0 Hz, 1H), 7.35 (d, J=8.0 Hz, 1H), 4.20 (d, J=6.8 Hz, 2H), 3.96-3.61 (m, 4H), 3.61-3.33 (m, 4H), 2.35 (m, 1H), 1.85 (m, 2H), 1.78-1.56 (m, 4H), 1.43 (m, 2H).

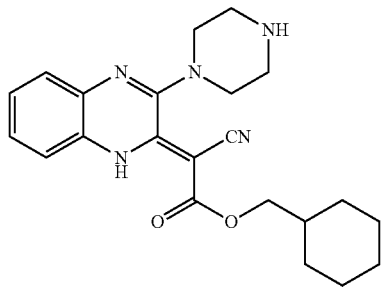 [SMILES: N#C/C(C(=O)OCC1CCCCC1)=C1/Nc2ccccc2N=C1N1CCNCC1]

(Z)-cyclohexylmethyl 2-cyano-2-(3-(piperazin-1-yl)
quinoxalin-2(1H)-ylidene)acetate cyclohexylmethyl 2-cyanoacetate was prepared following general procedure A. (Z)-cyclohexylmethyl 2-(3-chloroquinoxalin-2(1H)-ylidene)-2-cyanoacetate was prepared following general procedure B. (Z)-cyclohexylmethyl 2-cyano-2-(3-(piperazin-1-yl)quinoxalin-2(1H)-ylidene)acetate was prepared following general procedure C. TFA salt isolated. LCMS (m/z): 392 [M–H]⁻. 1H NMR (400 MHz, Chloroform-d) δ 14.25 (s, 1H), 9.85 (brs, 2H), 7.73 (d, J=7.8 Hz, 1H), 7.49 (t, J=7.7 Hz, 1H), 7.43 (t, J=7.0 Hz, 1H), 7.35 (d, J=8.0 Hz, 1H), 4.11 (d, J=6.8 Hz, 2H), 3.96-3.61 (m, 4H), 3.61-3.33 (m, 4H), 1.90-1.67 (m, 6H), 1.37-1.17 (m, 3H), 1.14-1.02 (m, 2H).

124

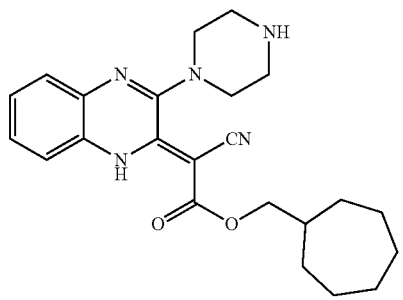 [SMILES: N#C/C(C(=O)OCC1CCCCCC1)=C1/Nc2ccccc2N=C1N1CCNCC1]

(Z)-cycloheptylmethyl 2-cyano-2-(3-(piperazin-1-yl)
quinoxalin-2(1H)-ylidene)acetate cycloheptylmethyl 2-cyanoacetate was prepared following general procedure A. (Z)-cycloheptylmethyl 2-(3-chloroquinoxalin-2(1H)-ylidene)-2-cyanoacetate was prepared following general procedure B. (Z)-cycloheptylmethyl 2-cyano-2-(3-(piperazin-1-yl)quinoxalin-2(1H)-ylidene)acetate was prepared following general procedure C. TFA salt isolated. LCMS (m/z): 406 [M–H]⁻. 1H NMR (400 MHz, Chloroform-d) δ 14.24 (brs, 1H), 9.88 (brs, 2H), 7.72 (d, J=8.1 Hz, 1H), 7.49 (t, J=7.5 Hz, 1H), 7.42 (t, J=7.2 Hz, 1H), 7.35 (d, J=7.8 Hz, 1H), 4.11 (d, J=6.3 Hz, 2H), 3.93-3.63 (m, 4H), 3.63-3.37 (m, 4H), 2.16-1.91 (m, 2H), 1.91-1.79 (m, 2H), 1.79-1.67 (m, 2H), 1.67-1.42 (m, 5H), 1.42-1.19 (m, 2H).

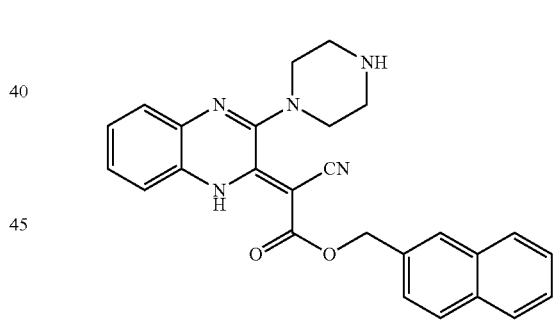

(Z)-naphthalen-2-ylmethyl 2-cyano-2-(3-(piperazin-1-yl)quinoxalin-2(1H)-ylidene)acetate naphthalen-2-ylmethyl 2-cyanoacetate was prepared following general procedure A. (Z)-naphthalen-2-ylmethyl 2-(3-chloroquinoxalin-2(1H)-ylidene)-2-cyanoacetate was prepared following general procedure B. (Z)-naphthalen-2-ylmethyl 2-cyano-2-(3-(piperazin-1-yl)quinoxalin-2(1H)-ylidene)acetate was prepared following general procedure C. TFA salt isolated. LCMS (m/z): 438 [M–H]⁻. 1H NMR (400 MHz, Methanol-d4) δ 7.98 (s, 1H), 7.90 (m, 3H), 7.75 (d, J=8.1 Hz, 1H), 7.55 (m, 6H), 5.54 (s, 2H), 3.95-3.75 (m, 2H), 3.72-3.45 (m, 4H), 3.40-3.28 (m, 2H).

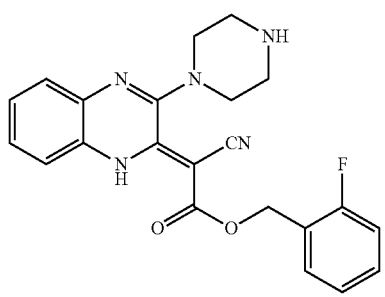 [SMILES: N#C/C(C(=O)OCc1ccccc1F)=C1/Nc2ccccc2N=C1N1CCNCC1]

(Z)-2-fluorobenzyl 2-cyano-2-(3-(piperazin-1-yl)quinoxalin-2(1H)-ylidene)acetate 2-fluorobenzyl 2-cyanoacetate was prepared following general procedure A. (Z)-2-fluorobenzyl 2-(3-chloroquinoxalin-2(1H)-ylidene)-2-cyanoacetate was prepared following general procedure B. (Z)-2-fluorobenzyl 2-cyano-2-(3-(piperazin-1-yl)quinoxalin-2(1H)-ylidene)acetate was prepared following general procedure C. TFA salt isolated. LCMS (m/z): 406 [M−H]⁻. 1H NMR (400 MHz, DMSO-d6) δ 13.75 (brs, 1H), 8.76 (brs, 2H), 7.83 (d, J=8.6 Hz, 1H), 7.69 (d, J=7.7 Hz, 1H), 7.54 (m, 2H), 7.51-7.39 (m, 2H), 7.34-7.21 (m, 2H), 5.38 (s, 2H), 3.66-3.10 (m, 8H).

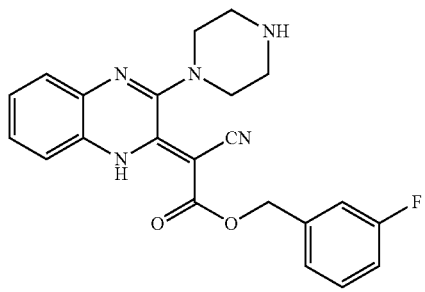 [SMILES: N#C/C(C(=O)OCc1cccc(F)c1)=C1/Nc2ccccc2N=C1N1CCNCC1]

(Z)-3-fluorobenzyl 2-cyano-2-(3-(piperazin-1-yl)quinoxalin-2(1H)-ylidene)acetate 3-fluorobenzyl 2-cyanoacetate was prepared following general procedure A. (Z)-3-fluorobenzyl 2-(3-chloroquinoxalin-2(1H)-ylidene)-2-cyanoacetate was prepared following general procedure B. (Z)-3-fluorobenzyl 2-cyano-2-(3-(piperazin-1-yl)quinoxalin-2(1H)-ylidene)acetate was prepared following general procedure C. TFA salt isolated. LCMS (m/z): 404 [M−H]⁻.

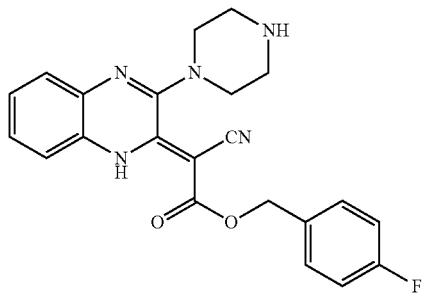 [SMILES: N#C/C(C(=O)OCc1ccc(F)cc1)=C1/Nc2ccccc2N=C1N1CCNCC1]

(Z)-4-fluorobenzyl 2-cyano-2-(3-(piperazin-1-yl)quinoxalin-2(1H)-ylidene)acetate 4-fluorobenzyl 2-cyanoacetate was prepared following general procedure A. (Z)-4-fluorobenzyl 2-(3-chloroquinoxalin-2(1H)-ylidene)-2-cyanoacetate was prepared following general procedure B. (Z)-4-fluorobenzyl 2-cyano-2-(3-(piperazin-1-yl)quinoxalin-2(1H)-ylidene)acetate was prepared following general procedure C. TFA salt isolated. LCMS (m/z): 404 [M−H]⁻. 1H NMR (400 MHz, DMSO-d6) δ 13.84 (s, 1H), 8.91 (s, 2H), 7.82 (d, J=7.9 Hz, 1H), 7.69 (d, J=7.8 Hz, 1H), 7.50 (m, 4H), 7.26 (t, J=8.2 Hz, 2H), 5.32 (s, 2H).

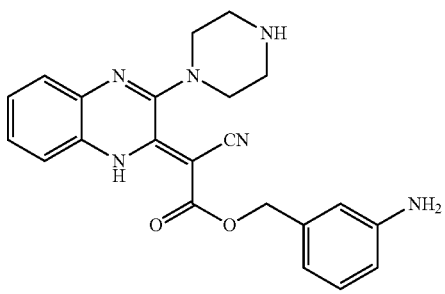 [SMILES: N#C/C(C(=O)OCc1cccc(N)c1)=C1/Nc2ccccc2N=C1N1CCNCC1]

(Z)-3-aminobenzyl 2-cyano-2-(3-(piperazin-1-yl)quinoxalin-2(1H)-ylidene)acetate 3-((tert-butoxycarbonyl)amino)benzyl 2-cyanoacetate was prepared following general procedure A. (Z)-3-((tert-butoxycarbonyl)amino)benzyl 2-(3-chloroquinoxalin-2(1H)-ylidene)-2-cyanoacetate was prepared following general procedure B. (Z)-3-aminobenzyl 2-(3-chloroquinoxalin-2(1H)-ylidene)-2-cyanoacetate was prepared following general procedure C. TFA salt isolated. LCMS (m/z): 401 [M−H]⁻. 1H NMR (400 MHz, DMSO-d6) δ 13.85 (s, 1H), 8.85 (brs, 2H), 7.81 (d, J=7.8 Hz, 1H), 7.69 (d, J=8.0 Hz, 1H), 7.53 (t, J=7.6 Hz, 1H), 7.46 (t, J=7.4 Hz, 1H), 7.07 (t, J=7.4 Hz, 1H), 6.72-6.47 (m, 3H), 5.19 (s, 2H), 3.68 (brs, 2H).

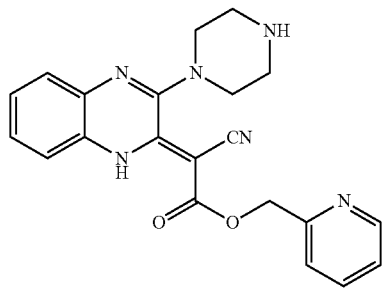 [SMILES: N#C/C(C(=O)OCc1ccccn1)=C1/Nc2ccccc2N=C1N1CCNCC1]

(Z)-pyridin-2-ylmethyl 2-cyano-2-(3-(piperazin-1-yl)quinoxalin-2(1H)-ylidene)acetate pyridin-2-ylmethyl 2-cyanoacetate was prepared following general procedure A. (Z)-pyridin-2-ylmethyl 2-(3-chloroquinoxalin-2(1H)-ylidene)-2-cyanoacetate was prepared following general procedure B. (Z)-pyridin-2-ylmethyl 2-cyano-2-(3-(piperazin-1-yl)quinoxalin-2(1H)-ylidene)acetate was prepared following general procedure C. TFA salt isolated. LCMS (m/z): 387 [M−H]⁻. 1H NMR (400 MHz, DMSO-d6) δ 13.77 (brs, 1H), 8.86 (br, 2H), 8.59 (br, 1H), 7.95-7.76 (m, 2H), 7.70 (d, J=7.7 Hz, 1H), 7.51 (t, J=7.6 Hz, 3H), 7.44-7.26 (m, 1H), 5.40 (s, 2H), 4.01-3.41 (m, 8H).

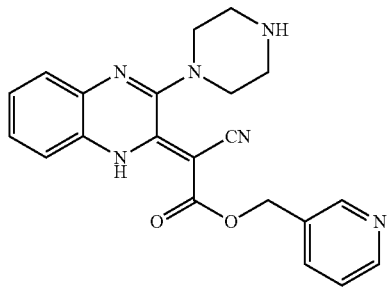 [SMILES: N#C/C(C(=O)OCc1cccnc1)=C1/Nc2ccccc2N=C1N1CCNCC1]

(Z)-pyridin-3-ylmethyl 2-cyano-2-(3-(piperazin-1-yl)quinoxalin-2(1H)-ylidene)acetate pyridin-3-ylmethyl 2-cyanoacetate was prepared following general procedure A. (Z)-pyridin-3-ylmethyl 2-(3-chloroquinoxalin-2(1H)-ylidene)-2-cyanoacetate was prepared following general procedure B. (Z)-pyridin-3-ylmethyl 2-cyano-2-(3-(piperazin-1-yl)quinoxalin-2(1H)-ylidene)acetate was prepared following general procedure C. TFA salt isolated. LCMS (m/z): 387 [M−H]⁻. 1H NMR (400 MHz, DMSO-d6) δ 13.76 (s, 1H), 8.91 (brs, 2H), 8.74 (s, 1H), 8.63 (d, J=4.8 Hz, 1H), 7.98 (d, J=7.7 Hz, 1H), 7.83 (d, J=8.0 Hz, 1H), 7.70 (d, J=8.0 Hz, 1H), 7.55 (m, 2H), 7.48 (t, J=7.6 Hz, 1H), 5.41 (s, 2H), 3.80-3.30 (m, 8H).

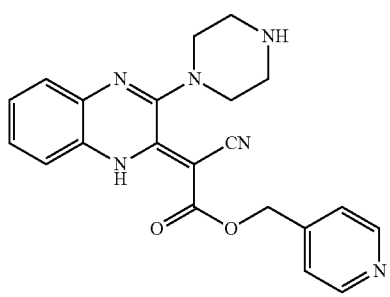 [SMILES: N#C/C(C(=O)OCc1ccncc1)=C1/Nc2ccccc2N=C1N1CCNCC1]

(Z)-pyridin-4-ylmethyl 2-cyano-2-(3-(piperazin-1-yl)quinoxalin-2(1H)-ylidene)acetate pyridin-4-ylmethyl 2-cyanoacetate was prepared following general procedure A. (Z)-pyridin-4-ylmethyl 2-(3-chloroquinoxalin-2(1H)-ylidene)-2-cyanoacetate was prepared following general procedure B. (Z)-pyridin-4-ylmethyl 2-cyano-2-(3-(piperazin-1-yl)quinoxalin-2(1H)-ylidene)acetate was prepared following general procedure C. TFA salt isolated. LCMS (m/z): 387 [M−H]⁻. 1H NMR (400 MHz, DMSO-d6) δ 13.71 (s, 1H), 8.93 (brs, 2H), 8.71 (d, J=6.0 Hz, 2H), 7.83 (d, J=7.5 Hz, 1H), 7.71 (d, J=8.7 Hz, 1H), 7.62-7.41 (m, 4H), 5.46 (s, 2H), 3.76-3.34 (m, 8H).

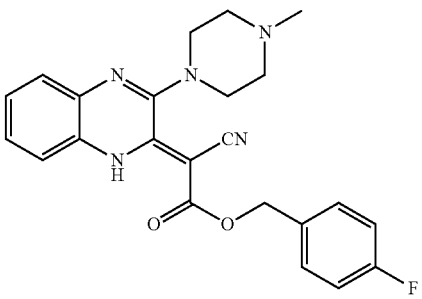 [SMILES: CN1CCN(C2=Nc3ccccc3N/C2=C(/C#N)C(=O)OCc2ccc(F)cc2)CC1]

(Z)-4-fluorobenzyl 2-cyano-2-(3-(4-methylpiperazin-1-yl)quinoxalin-2(1H)-ylidene)acetate 4-fluorobenzyl 2-cyanoacetate was prepared following general procedure A. (Z)-4-fluorobenzyl 2-(3-chloroquinoxalin-2(1H)-ylidene)-2-cyanoacetate was prepared following general procedure B. (Z)-4-fluorobenzyl 2-cyano-2-(3-(4-methylpiperazin-1-yl)quinoxalin-2(1H)-ylidene)acetate was prepared following general procedure C. TFA salt isolated. LCMS (m/z): 420 [M+H]⁺.

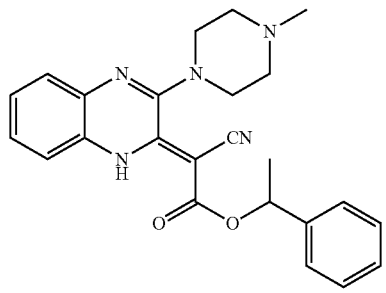 [SMILES: CC(OC(=O)/C(C#N)=C1\Nc2ccccc2N=C1N1CCN(C)CC1)c1ccccc1]

(Z)-1-phenylethyl 2-cyano-2-(3-(4-methylpiperazin-1-yl)quinoxalin-2(1H)-ylidene)acetate 1-phenylethyl 2-cyanoacetate was prepared following general procedure A. (Z)-1-phenylethyl 2-(3-chloroquinoxalin-2(1H)-ylidene)-2-cyanoacetate was prepared following general procedure B. (Z)-1-phenylethyl 2-cyano-2-(3-(4-methylpiperazin-1-yl)quinoxalin-2(1H)-ylidene)acetate was prepared following general procedure C and purified by chromatography on silica gel. LCMS (m/z): 416 [M+H]⁺.

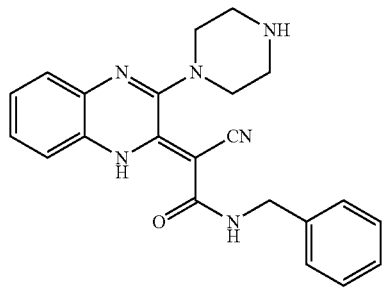 [SMILES: N#C/C(C(=O)NCc1ccccc1)=C1/Nc2ccccc2N=C1N1CCNCC1]

(Z)—N-benzyl-2-cyano-2-(3-(piperazin-1-yl)quinoxalin-2(1H)-ylidene)acetamide 2-cyano-N-(cyclohexylmethyl)acetamide was prepared following general procedure A using 2-cyanoacetic acid (1.3 eq), cyclohexylmethanamine (1.0 eq), EDCI (1.3 eq), HOBt (1.3 eq), Et₃N (2.0 eq) in DMF.

Preparation of (Z)—N-benzyl-2-(3-chloroquinoxalin-2(1H)-ylidene)-2-cyanoacetamide: A mixture of 2-cyano-N-(cyclohexylmethyl)acetamide (220 mg, 0.001220 mol, 1.0 eq), potassium tert-butoxide (342 mg, 0.00305 mol, 2.5 eq) and 2,3-dichloroquinoxaline (291 mg, 0.001463 mol, 1.2 eq) in dry THF (15 ml) was stirred at reflux for 3 h. The solution was cooled to room temperature, diluted in sat. NH₄Cl and extracted with DCM. The combined organic layers were dried over MgSO₄, filtered, concentrated and purified by column chromatography on silica gel (0 to 20% MeOH in DCM) to afford (Z)—N-benzyl-2-(3-chloroquinoxalin-2(1H)-ylidene)-2-cyanoacetamide (345 mg). ¹H NMR (400 MHz, Chloroform-d) δ 15.90 (brs, 1H), 7.76 (d, J=8.2 Hz, 1H), 7.59 (t, J=7.8 Hz, 1H), 7.48-7.33 (m, 2H), 6.61 (t, J=4.3 Hz, 1H), 3.24 (t, J=6.4 Hz, 2H), 1.92-1.63 (m, 5H), 1.60 (m, 1H), 1.24 (m, 3H), 1.00 (m, 2H).

Preparation of (Z)-A-benzyl-2-cyano-2-(3-(piperazin-1-yl)quinoxalin-2(1H)-ylidene)acetamide: Followed general procedure C. TFA salt isolated. LCMS (m/z): 391 [M–H]⁻.

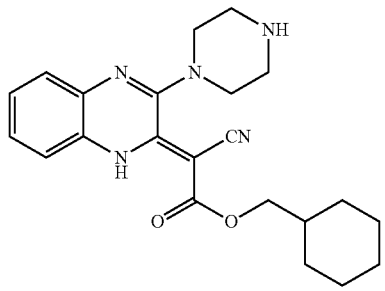 [SMILES: N#C/C(C(=O)OCC1CCCCC1)=C1/Nc2ccccc2N=C1N1CCNCC1]

(Z)-cyclohexylmethyl 2-cyano-2-(3-(piperazin-1-yl)quinolin-2(1H)-ylidene)acetate (Z)-cyclohexylmethyl 2-(3-bromoquinolin-2(1H)-ylidene)-2-cyanoacetate was prepared following general procedure B. Preparation of (Z)-cyclohexylmethyl 2-cyano-2-(3-(piperazin-1-yl)quinolin-2(1H)-ylidene)acetate To a solution of (Z)-cyclohexylmethyl 2-(3-bromoquinolin-2(1H)-ylidene)-2-cyanoacetate (35 mg, 0.00009037 mol, 1 eq) and piperazine (11.6 mg, 0.0001355 mol, 1.5 eq) in dry THF (3 ml) was added LiHMDS (0.32 ml, 0.0003162 mol, 3.5 eq) at room temperature. The reacting mixture was stirred at 60° C. for 2 h. The solution was cooled down, diluted in sat. NH₄Cl and extracted with DCM. The combined organic layers were dried over MgSO₄, filtered, concentrated and purified by reverse phase C18 (0 to 100% CH₃CN 0.1% TFA in water 0.1% TFA) affording (Z)-cyclohexylmethyl 2-cyano-2-(3-(piperazin-1-yl)quinolin-2(1H)-ylidene)acetate. TFA salt isolated. LCMS (m/z): 391 [M–H]⁻. ¹H NMR (400 MHz, DMSO-d₆) δ 12.96 (s, 1H), 9.02 (brs, 2H), 7.91 (d, J=8.3 Hz, 1H), 7.84 (d, J=8.3 Hz, 1H), 7.71 (t, J=7.8 Hz, 1H), 7.44 (t, J=7.7 Hz, 1H), 6.52 (s, 1H), 3.52-3.29 (br, 8H), 1.79-1.61 (m, 6H), 1.37-0.92 (m, 6H).

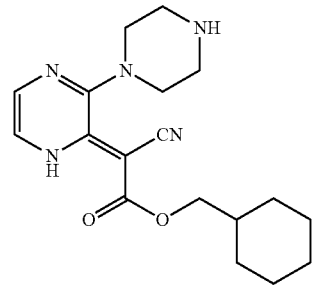 [SMILES: N#C/C(C(=O)OCC1CCCCC1)=C1/NC=CN=C1N1CCNCC1]

(Z)-cyclohexylmethyl 2-cyano-2-(3-(piperazin-1-yl)pyrazin-2(1H)-ylidene)acetate (Z)-cyclohexylmethyl 2-(3-chloropyrazin-2(1H)-ylidene)-2-cyanoacetate was prepared following general procedure B using 2,3-dichloropyrazine. (Z)-cyclohexylmethyl 2-cyano-2-(3-(piperazin-1-yl)pyrazin-2(1H)-ylidene)acetate was prepared following general procedure C. TFA salt isolated. LCMS (m/z): 342 [M–H]⁻. 1H NMR (400 MHz, Chloroform-d) δ 14.67 (brs, 1H), 9.81 (brs, 2H), 7.55 (br, 1H), 7.20 (br, 1H), 4.06 (d, J=6.3 Hz, 2H), 3.77-3.22 (brm, 8H), 1.76 (m, 6H), 1.27 (m, 3H), 1.05 (m, 2H).

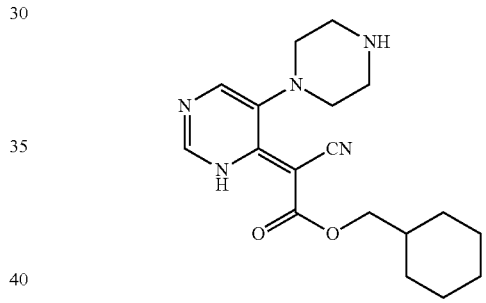

(Z)-cyclohexylmethyl 2-cyano-2-(5-(piperazin-1-yl)pyrimidin-4(3H)-ylidene)acetate (Z)-cyclohexylmethyl 2-(5-bromopyrimidin-4(3H)-ylidene)-2-cyanoacetate was prepared following general procedure B using 5-bromo-4-chloropyrimidine.

Preparation of (Z)-cyclohexylmethyl 2-cyano-2-(5-(piperazin-1-yl)pyrimidin-4(3H)-ylidene)acetate: A vial was loaded with (Z)-cyclohexylmethyl 2-(5-bromopyrimidin-4(3H)-ylidene)-2-cyanoacetate (150 mg, 0.0004435 mol, 1 eq), piperazine (49.6 mg, 0.0005765 mol, 1.3 eq), K₂CO₃ (122 mg, 0.000887 mol, 2.0 eq), L-Proline (15.3 mg, 0.0001330 mol, 0.3 eq), copper(I) iodide (16.8 mg, 0.0000887 mol, 0.2 eq) and DMSO (2 ml). The vial was flushed with argon and stirred for 3 h at 100° C. The reacting mixture was cooled down and diluted in water/AcOEt followed by extraction with AcOEt. The combined organic layers were washed with brine (2×), dried over MgSO₄, filtered and concentrated. The residue was purified by reverse phase (0 to 40% CH₃CN 0.1% TFA in water 0.1% TFA) to afford (Z)-cyclohexylmethyl 2-cyano-2-(5-(piperazin-1-yl)pyrimidin-4(3H)-ylidene)acetate. TFA salt isolated. LCMS (m/z): 342 [M–H]⁻.

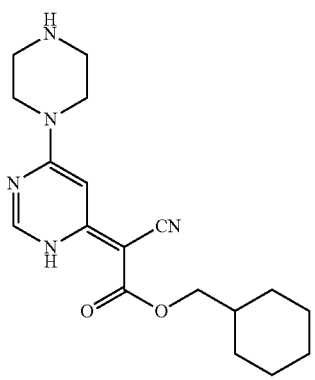 [SMILES: N#C/C(C(=O)OCC1CCCCC1)=C1\C=C(N2CCNCC2)N=CN1]

(Z)-cyclohexylmethyl 2-cyano-2-(6-(piperazin-1-yl)pyrimidin-4(3H)-ylidene)acetate (Z)-cyclohexylmethyl 2-(6-chloropyrimidin-4(3H)-ylidene)-2-cyanoacetate was prepared following general procedure B using 4,6-dichloropyrimidine. (Z)-cyclohexylmethyl 2-cyano-2-(6-(piperazin-1-yl)pyrimidin-4(3H)-ylidene)acetate was prepared following general procedure C. (Z)-cyclohexylmethyl 2-cyano-2-(6-(piperazin-1-yl)pyrimidin-4(3H)-ylidene)acetate was purified by column chromatography on silica gel (0 to 15% MeOH 3N $NH_3$ in DCM). LCMS (m/z): 342 [M–H]⁻. 1H NMR (400 MHz, Chloroform-d) δ 13.46 (s, 1H), 7.97 (s, 1H), 6.00 (s, 1H), 3.97 (d, J=6.5 Hz, 2H), 3.69 (br, 4H), 2.96 (m, 4H), 1.89-1.64 (m, 7H), 1.34-1.15 (m, 3H), 1.01 (q, J=11.8 Hz, 2H)

General Procedure F:

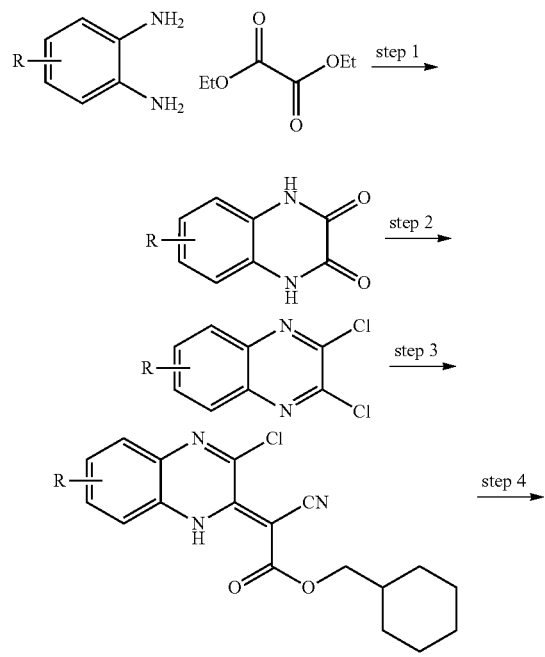

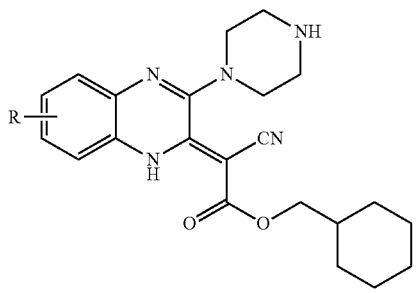

Step 1: A solution of substituted benzene-1,2-diamine in diethyl oxalate (solvent) was stirred at 130° C. until completion (3-20 h). The solution was cooled down and diluted in diethyl ether. The resulting precipitate was filtered, washed with ether and dried to afford the corresponding substituted 1,4-dihydroquinoxaline-2,3-dione.

Step 2: A solution of the substituted 1,4-dihydroquinoxaline-2,3-dione in $POCl_3$ (solvent) was stirred at 100° C. until completion (pyrido[2,3-b]pyrazine-2,3(1H,4H)-dione was stirred at 95° C. in $POCl_3$ for 4 days to prevent decomposition). The solution was poured on ice, basified to pH7 with 1M NaOH and extracted with DCM (3×) and 20% MeOH/DCM. The combined organic layers were washed with brine, dried over $MgSO_4$, filtered and concentrated. The residue was purified by column chromatography on silica gel.

For 5-nitroquinoxaline-2,3(1H,4H)-dione and 6-nitroquinoxaline-2,3(1H,4H)-dione: 6-nitroquinoxaline-2,3(1H,4H)-dione was diluted in $SOCl_2$ (solvent) followed by addition of DMF (1 ml). The reacting mixture was stirred at reflux until completion. The volatiles ware removed and the residue was diluted in DCM/sat. $NaHCO_3$ followed by extraction with DCM. The combined organic layers were dried over $MgSO_4$, filtered and concentrated. The residue was purified by column chromatography on silica gel.

Step 3: followed general procedure B. In most cases, a mixture of regioisomer was obtained and separated by column chromatography on silica gel.

Step 4: followed general procedure C.

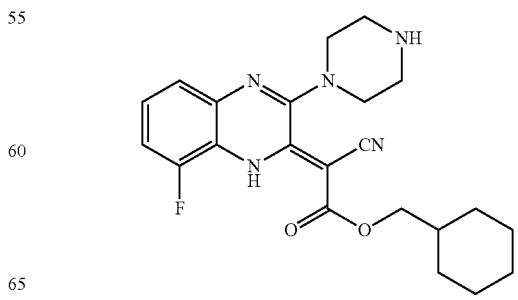

133

(Z)-cyclohexylmethyl 2-cyano-2-(8-fluoro-3-(piperazin-1-yl)quinoxalin-2(1H)-ylidene)acetate Prepared following general procedure F. LCMS (m/z): 410 [M–H]⁻.

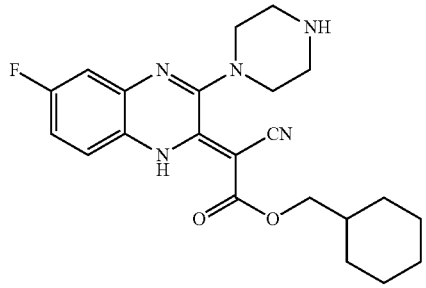 [SMILES: N#C/C(C(=O)OCC1CCCCC1)=C1/Nc2ccc(F)cc2N=C1N1CCNCC1]

(Z)-cyclohexylmethyl 2-cyano-2-(6-fluoro-3-(piperazin-1-yl)quinoxalin-2(1H)-ylidene)acetate Prepared following general procedure F. LCMS (m/z): 410 [M–H]⁻.

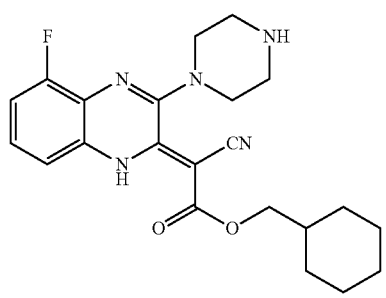 [SMILES: N#C/C(C(=O)OCC1CCCCC1)=C1/Nc2cccc(F)c2N=C1N1CCNCC1]

(Z)-cyclohexylmethyl 2-cyano-2-(5-fluoro-3-(piperazin-1-yl)quinoxalin-2(1H)-ylidene)acetate Prepared following general procedure F. LCMS (m/z): 410 [M–H]⁻.

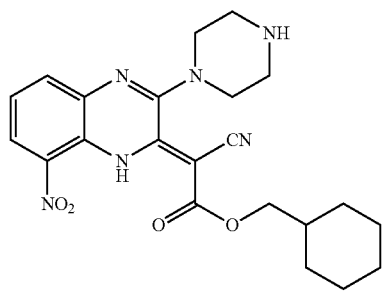 [SMILES: N#C/C(C(=O)OCC1CCCCC1)=C1/Nc2c(cccc2[N+](=O)[O-])N=C1N1CCNCC1]

134

(Z)-cyclohexylmethyl 2-cyano-2-(8-nitro-3-(piperazin-1-yl)quinoxalin-2(1H)-ylidene)acetate Prepared following general procedure F. LCMS (m/z): 437 [M–H]⁻.

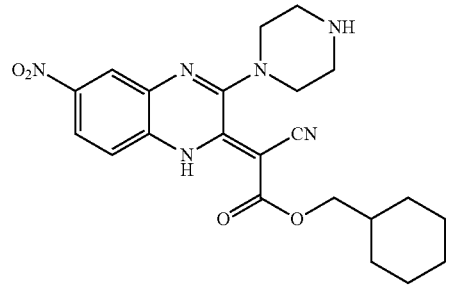 [SMILES: N#C/C(C(=O)OCC1CCCCC1)=C1/Nc2ccc([N+](=O)[O-])cc2N=C1N1CCNCC1]

(Z)-cyclohexylmethyl 2-cyano-2-(6-nitro-3-(piperazin-1-yl)quinoxalin-2(1H)-ylidene)acetate Prepared following general procedure F. LCMS (m/z): 437 [M–H]⁻.

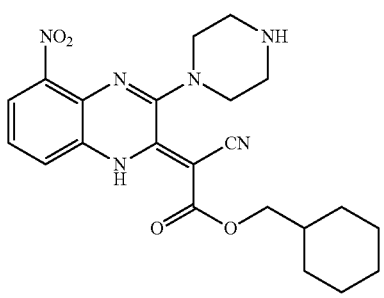 [SMILES: N#C/C(C(=O)OCC1CCCCC1)=C1/Nc2cccc([N+](=O)[O-])c2N=C1N1CCNCC1]

(Z)-cyclohexylmethyl 2-cyano-2-(5-nitro-3-(piperazin-1-yl)quinoxalin-2(1H)-ylidene)acetate Prepared following general procedure F. LCMS (m/z): 437 [M–H]⁻.

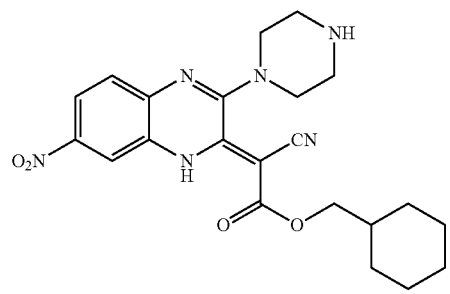 [SMILES: N#C/C(C(=O)OCC1CCCCC1)=C1/Nc2cc([N+](=O)[O-])ccc2N=C1N1CCNCC1]

(Z)-cyclohexylmethyl 2-cyano-2-(7-nitro-3-(piperazin-1-yl)quinoxalin-2(1H)-ylidene)acetate Prepared following general procedure F. LCMS (m/z): 437 [M−H]⁻.

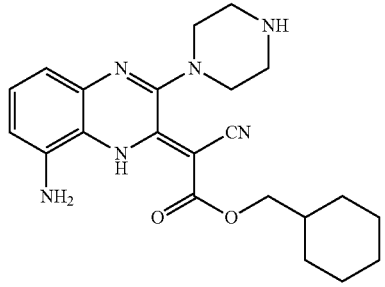

(Z)-cyclohexylmethyl 2-(8-amino-3-(piperazin-1-yl)quinoxalin-2(1H)-ylidene)-2-cyanoacetate To a solution of (Z)-cyclohexylmethyl 2-cyano-2-(8-nitro-3-(piperazin-1-yl)quinoxalin-2(1H)-ylidene)acetate (60 mg, 0.0001368 mol, 1 eq) in AcOH (4 ml) was added iron (53.4 mg, 0.0009576 mol, 7 eq). The solution was stirred at 110° C. until completion. The solution was cooled down, diluted in DCM and filtered over celite. The filtrates were concentrated, then diluted in sat. NaHCO₃ and extracted with AcOEt. The combined organic layers were washed with brined, dried over MgSO₄, filtered and concentrated. The residue was purified by column chromatography on silica gel (0 to 15% MeOH 3N NEE in DCM) then by reverse phase (10 to 50% CH₃CN 0.1% TFA in water 0.1% TFA). TFA salt isolated. LCMS (m/z): 409 [M+H]⁺.

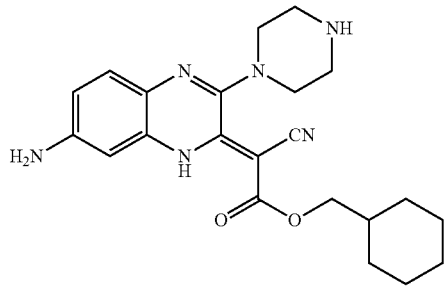

(Z)-cyclohexylmethyl 2-(7-amino-3-(piperazin-1-yl)quinoxalin-2(1H)-ylidene)-2-cyanoacetate The preparation was carried out analogously to the preparation of (Z)-cyclohexylmethyl 2-(8-amino-3-(piperazin-1-yl)quinoxalin-2(1H)-ylidene)-2-cyanoacetate. LCMS (m/z): 409 [M+H]⁺.

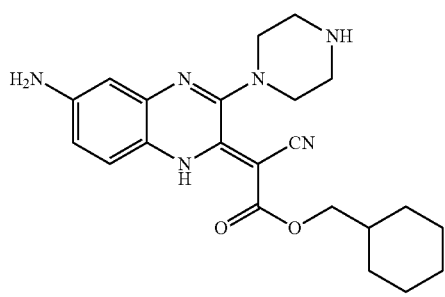

(Z)-cyclohexylmethyl 2-(6-amino-3-(piperazin-1-yl)quinoxalin-2(1H)-ylidene)-2-cyanoacetate The preparation was carried out analogously to the preparation of (Z)-cyclohexylmethyl 2-(8-amino-3-(piperazin-1-yl)quinoxalin-2(1H)-ylidene)-2-cyanoacetate. LCMS (m/z): 409 [M+H]⁺.

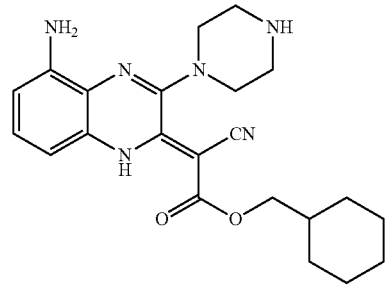 [SMILES: N#C/C(C(=O)OCC1CCCCC1)=C1/Nc2cccc(N)c2N=C1N1CCNCC1]

(Z)-cyclohexylmethyl 2-(5-amino-3-(piperazin-1-yl)quinoxalin-2(1H)-ylidene)-2-cyanoacetate The preparation was carried out analogously to the preparation of (Z)-cyclohexylmethyl 2-(8-amino-3-(piperazin-1-yl)quinoxalin-2(1H)-ylidene)-2-cyanoacetate. LCMS (m/z): 409 [M+H]⁺.

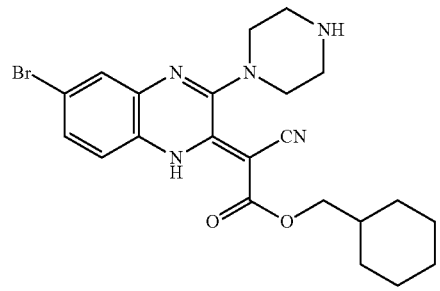 [SMILES: N#C/C(C(=O)OCC1CCCCC1)=C1/Nc2ccc(Br)cc2N=C1N1CCNCC1]

(Z)-cyclohexylmethyl 2-(6-bromo-3-(piperazin-1-yl)quinoxalin-2(1H)-ylidene)-2-cyanoacetate Prepared following general procedure F starting from 4-bromobenzene-1,2-diamine. A mixture of (Z)-cyclohexylmethyl 2-(7-bromo-3-(piperazin-1-yl)quinoxalin-2(1H)-ylidene)-2-cyanoacetate and (Z)-cyclohexylmethyl 2-(6-bromo-3-(piperazin-1-yl)quinoxalin-2(1H)-ylidene)-2-cyanoacetate was isolated. LCMS (m/z): 474 [M+H]⁺.

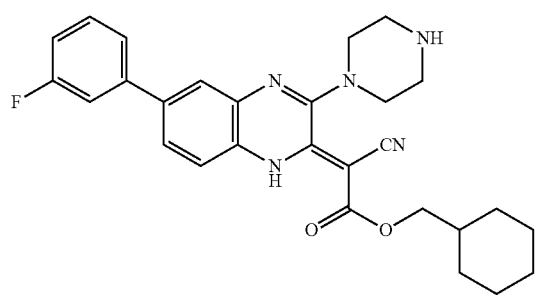 [SMILES: N#C/C(C(=O)OCC1CCCCC1)=C1/Nc2ccc(-c3cccc(F)c3)cc2N=C1N1CCNCC1]

(Z)-cyclohexylmethyl 2-cyano-2-(6-(3-fluorophenyl)-3-(piperazin-1-yl)quinoxalin-2(1H)-ylidene)acetate A solution of (Z)-cyclohexylmethyl 2-(6-bromo-3-(piperazin-1-yl)quinoxalin-2(1H)-ylidene)-2-cyanoacetate (25 mg, 0.05292 mmol, 1 eq), Cesium carbonate (43.1 mg, 0.1323 mmol, 2.5 eq), PdCl₃dppf (1.93 mg, 0.002646 mmol, 0.05 eq), and 3-(fluorophenyl)boronic acid (14.8 mg, 0.1058 mmol, 2 eq) in dioxane:water (4:1, 2 ml) was stirred at 100° C. overnight. The solution was cooled down, diluted in water and extracted with DCM. The combined organic layers were washed with brine, dried over MgSO₄, filtered and concentrated. The residue was purified by column chromatography on silica gel (0 to 15% MeOH 3N NH₃ in DCM) affording (Z)-cyclohexylmethyl 2-cyano-2-(6-(2-fluorophenyl)-3-(piperazin-1-yl)quinoxalin-2(1H)-ylidene)acetate (14 mg). LCMS (m/z): 486 [M−H]⁻.

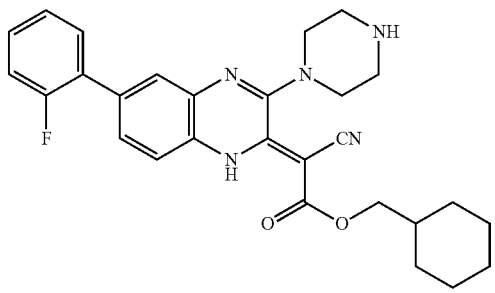 [SMILES: N#C/C(C(=O)OCC1CCCCC1)=C1/Nc2ccc(-c3ccccc3F)cc2N=C1N1CCNCC1]

(Z)-cyclohexylmethyl 2-cyano-2-(6-(2-fluorophenyl)-3-(piperazin-1-yl)quinoxalin-2(1H)-ylidene)acetate A solution of (Z)-cyclohexylmethyl 2-(6-bromo-3-(piperazin-1-yl)quinoxalin-2(1H)-ylidene)-2-cyanoacetate (25 mg, 0.05292 mmol, 1 eq), K₃PO₄ (22.4 mg, 0.1058 mmol, 2 eq), Pd XPhos G3 (2.23 mg, 0.002646 mmol, 0.05 eq), and (2-fluorophenyl)boronic acid (14.8 mg, 0.1058 mmol, 2 eq) in dioxane:water (4:1, 2 mL) was stirred at 100° C. overnight. The solution was cooled down, diluted in water and extracted with DCM. The combined organic layers were washed with brine, dried over MgSO₄, filtered and concentrated. The residue was purified by column chromatography on silica gel (0 to 15% MeOH 3N NH₃ in DCM) affording (Z)-cyclohexylmethyl 2-cyano-2-(6-(2-fluorophenyl)-3-(piperazin-1-yl)quinoxalin-2(1H)-ylidene)acetate (10 mg). LCMS (m/z): 488 [M+H]⁺.

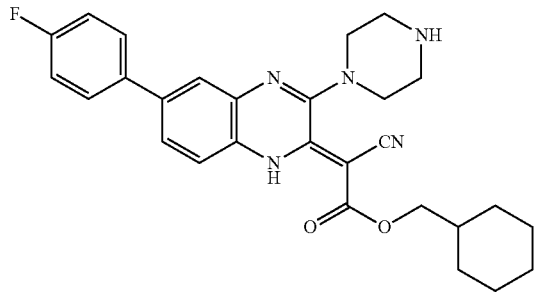 [SMILES: N#C/C(C(=O)OCC1CCCCC1)=C1/Nc2ccc(-c3ccc(F)cc3)cc2N=C1N1CCNCC1]

(Z)-cyclohexylmethyl 2-cyano-2-(6-(4-fluorophenyl)-3-(piperazin-1-yl)quinoxalin-2(1H)-ylidene)acetate The reaction was carried out analogously to the preparation of (Z)-cyclohexylmethyl 2-cyano-2-(6-(2-fluorophenyl)-3-(piperazin-1-yl)quinoxalin-2(1H)-ylidene)acetate. LCMS (m/z): 486 [M−H]⁻.

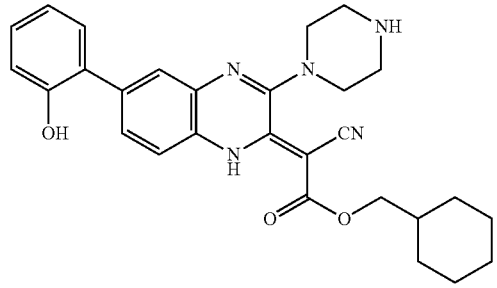 [SMILES: N#C/C(C(=O)OCC1CCCCC1)=C1/Nc2ccc(-c3ccccc3O)cc2N=C1N1CCNCC1]

(Z)-cyclohexylmethyl 2-cyano-2-(6-(2-hydroxyphenyl)-3-(piperazin-1-yl)quinoxalin-2(1H)-ylidene)acetate The reaction was carried out analogously to the preparation of (Z)-cyclohexylmethyl 2-cyano-2-(6-(2-fluorophenyl)-3-(piperazin-1-yl)quinoxalin-2(1H)-ylidene)acetate. LCMS (m/z): 486 [M+H]⁺.

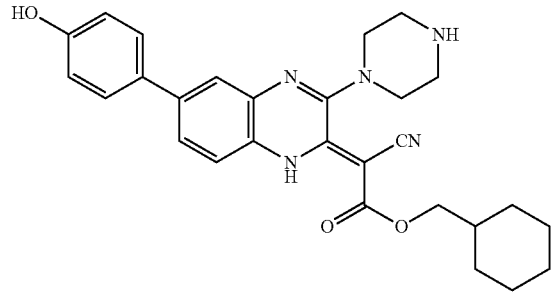 [SMILES: N#C/C(C(=O)OCC1CCCCC1)=C1/Nc2ccc(-c3ccc(O)cc3)cc2N=C1N1CCNCC1]

(Z)-cyclohexylmethyl 2-cyano-2-(6-(4-hydroxyphenyl)-3-(piperazin-1-yl)quinoxalin-2(1H)-ylidene)acetate The reaction was carried out analogously to the preparation of (Z)-cyclohexylmethyl 2-cyano-2-(6-(2-fluorophenyl)-3-(piperazin-1-yl)quinoxalin-2(1H)-ylidene)acetate. LCMS (m/z): 486 [M+H]⁺.

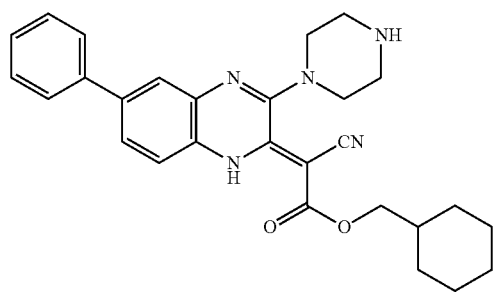 [SMILES: N#C/C(C(=O)OCC1CCCCC1)=C1/Nc2ccc(-c3ccccc3)cc2N=C1N1CCNCC1]

(Z)-cyclohexylmethyl 2-cyano-2-(6-phenyl-3-(piperazin-1-yl)quinoxalin-2(1H)-ylidene)acetate The reaction was carried out analogously to the preparation of (Z)-cyclohexylmethyl 2-cyano-2-(6-(3-fluorophenyl)-3-(piperazin-1-yl)quinoxalin-2(1H)-ylidene)acetate. LCMS (m/z): 468 [M−H]⁻.

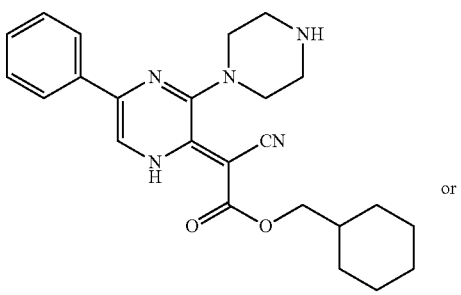

or ylmethyl 2-(3-chloro-5-phenylpyrazin-2(1H)-ylidene)-2-cyanoacetate or (Z)-cyclohexylmethyl 2-(3-chloro-6-phenylpyrazin-2(1H)-ylidene)-2-cyanoacetate: prepared following general procedure B leading to the formation of regioisomer 10:1 mixture. (Z)-cyclohexylmethyl 2-cyano-2-(5-phenyl-3-(piperazin-1-yl)pyrazin-2(1H)-ylidene)acetate or (Z)-cyclohexylmethyl 2-cyano-2-(6-phenyl-3-(piperazin-1-yl)pyrazin-2(1H)-ylidene)acetate: prepared according to general procedure C. LCMS (m/z): 418 [M−H]⁻.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term 5-FAM
<220> FEATURE:
<221> NAME/KEY: MOD_RES
<222> LOCATION: (7)..(7)
<223> OTHER INFORMATION: Phospho-Ser
<220> FEATURE:
<223> OTHER INFORMATION: C-term CONH2

<400> SEQUENCE: 1

Lys Arg Arg Arg Ala Leu Ser Val Ala Ser Leu Pro Gly Leu
1               5                   10
```

-continued

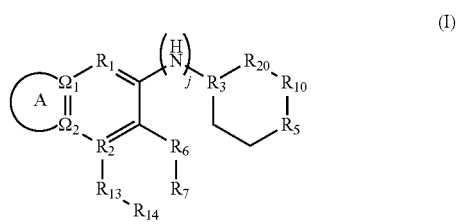

(Z)-cyclohexylmethyl 2-cyano-2-(5-phenyl-3-(piperazin-1-yl)pyrazin-2(1H)-ylidene)acetate or (Z)-cyclohexylmethyl 2-cyano-2-(6-phenyl-3-(piperazin-1-yl)pyrazin-2(1H)-ylidene)acetate 2,3-dichloro-5-phenylpyrazine was prepared according to PCT Int Appl., 2005035532. Preparation of (Z)-cyclohex-

What is claimed is:

1. A method of treating a cancer in a subject in need thereof, the method comprising administering to the subject a therapeutically effective amount of at least one compound of formula (I), or a salt or N-oxide thereof:

(I)

wherein:
"j" is 0;
$R_1$ is selected from the group consisting of N, C—H, C—F and C—OH, where at least one of $R_1$ and $R_2$ is N;

$R_2$ is selected from the group consisting of N, C—F, C—OH, and C;

$R_3$ is selected from the group consisting of N, CH, CF and COH;

$R_5$ is selected from the group consisting of N(H), N($C_1$-$C_6$ alkyl), C(H)—$NH_2$, C(H)—NH($C_1$-$C_6$ alkyl), C(H)—($C_1$-$C_6$ alkyl)-$NH_2$, C(H)—C(=O)—$NH_2$, and C(H)—N($C_1$-$C_6$ alkyl)($C_1$-$C_6$ alkyl);

one of $R_6$ or $R_{13}$ is absent and the other of $R_6$ or $R_{13}$ is selected from the group consisting of —C(H)(CN)—, —C(H)(C≡CH)—, —$CH_2$—, —C(H)($CH_3$)—, —C($CH_3$)(CN)—, —N(CN)—, and —NH—;

where $R_7$ is hydrogen when $R_6$ is absent, and where $R_{14}$ is hydrogen when $R_{13}$ is absent;

$R_7$ and $R_{14}$ are is independently selected from the group consisting of —C(=O)$OR_8$, —C(=O)N($R_9$)$R_8$, —C(=O)N(H)$R_8$, —NHC(=O)$R_8$, —C(=O)C($R_9$)=C($R_9$)($R_9$), $N^1$—$R_8$-1H-imidazol-2-yl, —$CH_2OR_8$, and 2-$R_8$-1,3,5-oxadiazol-5-yl;

$R_{10}$ and $R_{20}$ are independently selected from the group consisting of C(H)($R_{12}$), C($R_{12}$)($R_{12}$), and C(=O);

each occurrence of $R_8$ is independently selected from the group consisting of H, $C_1$-$C_6$ alkyl, aryl, $C_3$-$C_8$ cycloalkyl, $C_3$-$C_8$ cycloalkyl-($C_1$-$C_3$)alkyl, $C_3$-$C_8$ heterocycloalkyl-($C_1$-$C_3$)alkyl, aryl-($C_1$-$C_3$)alkyl, ($C_1$-$C_6$) hydroxyalkyl, imidazol-2-yl optionally substituted with methyl, and oxadiazol-5-yl optionally substituted with methyl or benzyl;

each occurrence of $R_9$ is independently selected from the group consisting of H, $C_1$-$C_6$ alkyl, aryl, and halogen;

each occurrence of $R_{12}$ is independently selected from the group consisting of H, $C_1$-$C_6$ alkyl, aryl, ($C_1$-$C_6$) hydroxyalkyl, $C_3$-$C_8$ cycloalkyl-($C_1$-$C_3$)alkyl, —C(=O)O—($C_1$-$C_6$)alkyl;

moiety "A" is selected from the group consisting of:

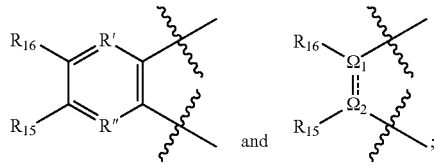
and wherein R' and R" are independently selected from the group consisting of N, C—H, C—F, and C—$R_{17}$;

$\Omega_1$ and $\Omega_2$ are independently selected at each occurrence from C, CH, and N and the dashed ("=") bond" is a double bond or single bond;

$R_{15}$, $R_{16}$, and $R_{17}$ are independently selected at each occurrence from hydrogen, aryl, halo, amino, and nitro; and each alkyl, aryl, arylalkyl, heterocycloalkylalkyl, cycloalkylalkyl, and/or cycloalkyl group is independently optionally substituted with at least one selected from the group consisting of $C_1$-$C_6$ alkyl, halo, hydroxy, alkoxy, amino, monoalkylamino, dialkylamino, aminocarbonyl, acylamino, carboxy, alkoxycarbonyl, sulfanyl, sulfinyl, sulfonyl, and sulfonamide; and, each aryl and/or aryl($C_1$-$C_3$)alkyl group is independently optionally substituted with at least one selected from the group consisting of $C_1$-$C_6$ alkyl, $C_2$-$C_6$ alkenyl, $C_2$-$C_6$ alkynyl, aryl, heterocyclyl, heteroaryl, halo, haloalkyl (including trifluoromethyl), —SR, —S(=O)($C_1$-$C_6$ alkyl), —S(=O)$_2$($C_1$-$C_6$ alkyl), —S(=O)$_2$NRR, —OH, —OR, —C(=O)R, —O—C(=O)R, —C(=O)OR, —OC(=O)O($C_1$-$C_6$ alkyl), —NRR, —C(=O)NRR, —N(R)C(=O)R, —C(=NR)NRR, —P(=O)(OR)$_2$, cyano and nitro; wherein each R is independently selected from the group consisting of H, alkyl, heteroalkyl, cycloalkyl, aryl, heterocyclyl, and heteroaryl;

wherein said cancer is characterized by overexpression, hyperactivation and/or uncontrolled activation of casein kinase 1 and selected from hematological cancer and colorectal cancer.

2. The method of claim 1, wherein the cancer comprises a hematological cancer.

3. The method of claim 1, wherein the compound has the structure of formula (Ia), or a salt or N-oxide thereof:

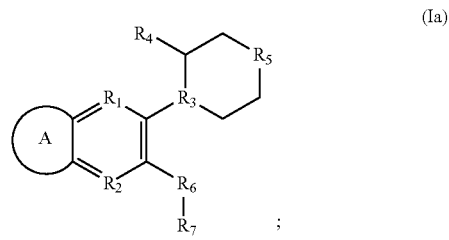

wherein $R_4$ is selected from the group consisting of H, CN and $CH_3$.

4. The method of claim 1, wherein the compound has the structure of formula (Ib), or a salt or N-oxide thereof:

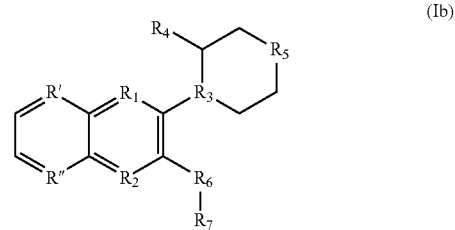

wherein $R_4$ is selected from the group consisting of H, CN and $CH_3$.

5. The method of claim 1, wherein the compound has the structure of formula (Ic), or a salt or N-oxide thereof:

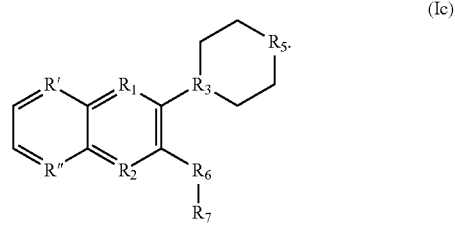

6. The method of claim 1, wherein the compound has the structure of formula (Id), or a salt or N-oxide thereof:

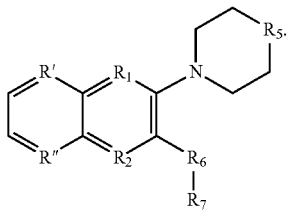

(Id)

7. The method of claim 1, wherein the compound has the structure of formula (Ie), or a salt or N-oxide thereof:

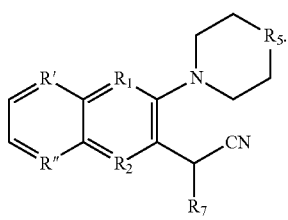

(Ie)

8. The method of claim 1, wherein the compound has the structure of formula (Ih), or a salt or N-oxide thereof:

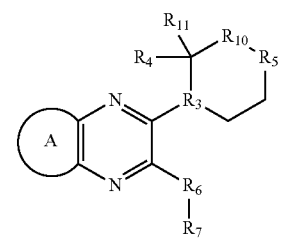

(Ih)

wherein $R_4$ and $R_{11}$ are independently selected from the group consisting of H, CN and $CH_3$.

9. The method of claim 2, wherein the hematological cancer comprises AML or MDS.

10. The method of claim 1, wherein the cancer comprises colorectal cancer.

11. The method of claim 6, wherein $R_5$ is NH or $N(C_1$-$C_6)$ alkyl.

12. The method of claim 1, wherein $R_7$ is selected from the group consisting of —C(=O)$OR_8$, —C(=O)N($R_9$)$R_8$, and —C(=O)C($R_9$)=C($R_9$)$_2$.

13. The method of claim 1, wherein
"j" is 0;
one of $R_6$ or $R_{13}$ is absent and the other of $R_6$ or $R_{13}$ is selected from the group consisting of —C(H)(CN)—, —C(CH$_3$)(CN)—, and —N(CN)—; and
$R_7$ and $R_{14}$ are independently selected from the group consisting of —C(=O)$OR_8$, $N^1$—$R_8$-1H-imidazol-2-yl, —CH$_2$OR$_8$, and 2-$R_8$-1,3,5-oxadiazol-5-yl.

14. The method of claim 1, wherein the compound is:
cyclohexyl 2-cyano-2-(3-(4-ethylpiperazin-1-yl)quinolin-2-yl)acetate
benzyl 2-cyano-2-(3-(4-methylpiperazin-1-yl)quinoxalin-2-yl)acetate
2-ethylbutyl 2-cyano-2-(3-(4-ethylpiperazin-1-yl)quinoxalin-2-yl)acetate
cyclohexyl 2-cyano-2-(3-(4-methylpiperazin-1-yl)quinoxalin-2-yl)acetate
isopropyl 2-cyano-2-(3-(4-methylpiperazin-1-yl)quinoxalin-2-yl)acetate
benzyl 2-cyano-2-(3-(4-methylpiperazin-1-yl)quinoxalin-2-yl)propanoate
1-phenylethyl 2-cyano-2-(3-(4-methylpiperazin-1-yl)quinoxalin-2-yl)acetate
2-phenylpropan-2-yl 2-cyano-2-(3-(4-methylpiperazin-1-yl)quinoxalin-2-yl)acetate
benzyl 2-cyano-2-(3-(2,4-dimethylpiperazin-1-yl)quinoxalin-2-yl)acetate
benzyl 2-cyano-2-(3-(1-methylpiperidin-4-yl)quinoxalin-2-yl)acetate
2-(1-benzyl-1H-imidazol-2-yl)-2-(3-(4-methylpiperazin-1-yl)quinoxalin-2-yl)acetonitrile
2-(1-methyl-1H-imidazol-2-yl)-2-(3-(4-methylpiperazin-1-yl)quinoxalin-2-yl)acetonitrile
2-(5-benzyl-1,3,4-oxadiazol-2-yl)-2-(3-(4-methylpiperazin-1-yl)quinoxalin-2-yl)acetonitrile
2-(5-methyl-1,3,4-oxadiazol-2-yl)-2-(3-(4-methylpiperazin-1-yl)quinoxalin-2-yl)acetonitrile
benzyl 2-cyano-2-(3-(4-methylpiperazin-1-yl)quinolin-2-yl)acetate
benzyl 2-cyano-2-(2-(4-methylpiperazin-1-yl)-1,5-naphthyridin-3-yl)acetate
benzyl 2-cyano-2-(3-(4-methylpiperazin-1-yl)-4-oxo-1,4-dihydroquinolin-2-yl)acetate
benzyl 2-cyano-2-(3-(4-methylpiperazin-1-yl)pyrazin-2-yl)acetate
benzyl 2-cyano-2-(4-fluoro-3-(4-methylpiperazin-1-yl)quinolin-2-yl)acetate
4-fluorobenzyl 2-cyano-2-(3-(4-methylpiperazin-1-yl)quinoxalin-2-yl)acetate
2-ethylbutyl 2-cyano-2-(3-(4-methylpiperazin-1-yl)quinoxalin-2-yl)acetate
2-ethylbutyl 2-cyano-2-(3-(piperazin-1-yl)quinoxalin-2-yl)acetate
2,2 dimethyl propyl 2-cyano-2-(3-(piperazin-1-yl)quinoxalin-2-yl)acetate
2,2 dimethyl propyl 2-cyano-2-(3-(methylpiperazin-1-yl)quinoxalin-2-yl)acetate
2-fluorobenzyl 2-cyano-2-(3-(piperazin-1-yl)quinoxalin-2-yl)acetate
3-fluorobenzyl 2-cyano-2-(3-(piperazin-1-yl)quinoxalin-2-yl)acetate
4-fluorobenzyl 2-cyano-2-(3-(piperazin-1-yl)quinoxalin-2-yl)acetate
3-aminobenzyl 2-cyano-2-(3-(piperazin-1-yl)quinoxalin-2-yl)acetate
cyclohexyl 2-cyano-2-(3-(4-methylpiperazin-1-yl)quinoxalin-2-yl)acetate
cycloheptylmethyl 2-cyano-2-(3-(piperazin-1-yl)quinoxalin-2-yl)acetate
cyclohexylmethyl 2-cyano-2-(3-(4-methylpiperazin-1-yl)quinoxalin-2-yl)acetate
cyclohexylmethyl 2-cyano-2-(3-(4-methylpiperazin-1-yl)quinoxalin-2-yl)acetate
cyclopentylmethyl 2-cyano-2-(3-(piperazin-1-yl)quinoxalin-2-yl)acetate
2-ethylbutyl 2-cyano-2-(3-(3-phenylpiperazin-1-yl)quinoxalin-2-yl)acetate
2-ethylbutyl 2-cyano-2-(3-((S)-3-methylpiperazin-1-yl)quinoxalin-2-yl)acetate 4-fluorobenzyl 2-cyano-2-(3-(piperazin-1-yl)quinoxalin-2-yl)acetate 2-ethylbutyl 2-cyano-2-(3-(3-ethylpiperazin-1-yl)quinoxalin-2-yl)acetate 2-ethylbutyl 2-cyano-2-(3-(3-(hydroxymethyl)piperazin-1-yl)quinoxalin-2-yl)acetate cyclohexylmethyl 2-cyano-2-(3-(3-methylpiperazin-1-yl)quinoxalin-2-yl)acetate methyl 4-(3-(1-cyano-2-(2-ethylbutoxy)-2-oxoethyl)quinoxalin-2-yl)piperazine-2-carboxylate 2-ethylbutyl 2-cyano-2-(3-(3-oxopiperazin-1-yl)quinoxalin-2-yl)acetate 2-cyano-N-(cyclohexylmethyl)-2-(3-(piperazin-1-yl)quinoxalin-2-yl)acetamide pyridin-3-ylmethyl 2-cyano-2-(3-(piperazin-1-yl)quinoxalin-2-yl)acetate 3-aminobenzyl 2-cyano-2-(3-(piperazin-1-yl)quinoxalin-2-yl)acetate cyclohexylmethyl 2-cyano-2-(3-(piperazin-1-yl)quinoxalin-2-yl)acetate 2-ethylbutyl 2-cyano-2-(3-(3-methylpiperazin-1-yl)quinoxalin-2-yl)acetate naphthalen-2-ylmethyl 2-cyano-2-(3-(piperazin-1-yl)quinoxalin-2-yl)acetate 4-fluorobenzyl 2-cyano-2-(3-(4-methylpiperazin-1-yl)quinoxalin-2-yl)acetate 2-ethylbutyl 2-cyano-2-(3-((R)-3-methylpiperazin-1-yl)quinoxalin-2-yl)acetate cyclohexylmethyl 2-cyano-2-(8-fluoro-3-(piperazin-1-yl)quinoxalin-2-yl)acetate cyclohexylmethyl 2-cyano-2-(6-fluoro-3-(piperazin-1-yl)quinoxalin-2-yl)acetate cyclohexylmethyl 2-cyano-2-(6-(2-fluorophenyl)-3-(piperazin-1-yl)quinoxalin-2-yl)acetate cyclohexylmethyl 2-cyano-2-(6-(2-hydroxyphenyl)-3-(piperazin-1-yl)quinoxalin-2-yl)acetate N-benzyl-2-cyano-2-(3-(piperazin-1-yl)quinoxalin-2-yl)acetamide cyclohexylmethyl 2-cyano-2-(5-fluoro-3-(piperazin-1-yl)quinoxalin-2-yl)acetate cyclohexylmethyl 2-cyano-2-(6-nitro-3-(piperazin-1-yl)quinoxalin-2-yl)acetate cyclohexylmethyl 2-cyano-2-(6-phenyl-3-(piperazin-1-yl)quinoxalin-2-yl)acetate cyclohexylmethyl 2-cyano-2-(6-phenyl-3-(piperazin-1-yl)pyrazin-2-yl)acetate cyclohexylmethyl 2-cyano-2-(6-(4-hydroxyphenyl)-3-(piperazin-1-yl)quinoxalin-2-yl)acetate cyclohexylmethyl 2-cyano-2-(6-(3-fluorophenyl)-3-(piperazin-1-yl)quinoxalin-2-yl)acetate cyclohexylmethyl 2-cyano-2-(3-(piperazin-1-yl)quinolin-2-yl)acetate cyclohexylmethyl 2-cyano-2-(6-(4-fluorophenyl)-3-(piperazin-1-yl)quinoxalin-2-yl)acetate 5-cyclohexyl-3-oxo-2-(3-(piperazin-1-yl)pyrazin-2-yl)pentanenitrile 5-cyclohexyl-3-oxo-2-(3-(piperazin-1-yl)quinoxalin-2-yl)pentanenitrile cyclohexyl 2-(7-amino-3-(piperazin-1-yl)quinoxalin-2-yl)-2-cyanoacetate or a salt or N-oxide thereof.

15. The method according to claim 1, wherein the compound is 2-ethylbutyl 2-cyano-2-(3-(4-ethylpiperazin-1-yl)quinoxalin-2-yl)acetate; or a salt or an N-oxide thereof.

* * * * *